(12) United States Patent
Duke et al.

(10) Patent No.: US 7,439,042 B2
(45) Date of Patent: Oct. 21, 2008

(54) YEAST-BASED THERAPEUTIC FOR CHRONIC HEPATITIS C INFECTION

(75) Inventors: Richard C. Duke, Denver, CO (US); Alex Franzusoff, Denver, CO (US); Aurelia Haller, Boulder, CO (US); Thomas H. King, Denver, CO (US)

(73) Assignee: GlobeImmune, Inc., Louisville, CO (US)

( * ) Notice: Subject to any disclaimer, the term of this patent is extended or adjusted under 35 U.S.C. 154(b) by 0 days.

(21) Appl. No.: 11/254,252

(22) Filed: Oct. 18, 2005

(65) Prior Publication Data

US 2006/0110755 A1    May 25, 2006

Related U.S. Application Data

(63) Continuation-in-part of application No. 10/738,646, filed on Dec. 16, 2003.

(60) Provisional application No. 60/620,158, filed on Oct. 18, 2004, provisional application No. 60/434,163, filed on Dec. 16, 2002.

(51) Int. Cl.
*C12N 15/33* (2006.01)

(52) U.S. Cl. .................. 435/69.7; 530/350; 530/402

(58) Field of Classification Search .................. None
See application file for complete search history.

(56) References Cited

U.S. PATENT DOCUMENTS

| | | | |
|---|---|---|---|
| 4,775,622 A | 10/1988 | Hitzeman et al. | 435/68 |
| 5,413,914 A | 5/1995 | Franzusoff | 435/23 |
| 5,641,654 A | 6/1997 | Maki et al. | |
| 5,683,864 A | 11/1997 | Houghton et al. | |
| 5,830,463 A * | 11/1998 | Duke et al. | 424/93.51 |
| 5,858,378 A | 1/1999 | Bostwick | 424/274.1 |
| 5,871,903 A | 2/1999 | Miyamura et al. | |
| 5,919,651 A | 7/1999 | Hitzeman et al. | 435/69.1 |
| 5,961,978 A | 10/1999 | Gaudernack et al. | 424/185.1 |
| 6,027,729 A | 2/2000 | Houghton et al. | |
| 6,071,693 A | 6/2000 | Cha et al. | |
| 6,074,816 A | 6/2000 | Houghton et al. | |
| 6,090,546 A | 7/2000 | Breivik et al. | 435/6 |
| 6,121,020 A * | 9/2000 | Selby et al. | 435/69.3 |
| 6,187,307 B1 | 2/2001 | Cohen | 424/93.21 |
| 6,194,140 B1 | 2/2001 | Houghton et al. | 435/4 |
| 6,284,249 B1 * | 9/2001 | Barban | 424/192.1 |
| 6,326,171 B1 | 12/2001 | Selby et al. | 435/69.3 |
| 6,361,969 B1 | 3/2002 | Galeotti | 435/69.1 |
| 6,521,423 B1 | 2/2003 | Houghton et al. | 435/69.1 |
| 6,558,951 B1 | 5/2003 | Tomai et al. | 435/377 |
| 6,562,346 B1 | 5/2003 | Paliard et al. | |
| 6,759,046 B1 | 7/2004 | Gaudernack et al. | 424/184.1 |
| 6,861,057 B2 | 3/2005 | Gaudernack et al. | 424/184.1 |
| 6,890,737 B1 | 5/2005 | Maertens et al. | 435/69.3 |
| 6,986,892 B1 * | 1/2006 | Coit et al. | 424/228.1 |
| 7,048,930 B2 | 5/2006 | Bosman et al. | 424/189.1 |
| 7,083,787 B2 * | 8/2006 | Duke et al. | 424/184.1 |
| 2002/0004048 A1 | 1/2002 | Ralston et al. | 424/189.1 |
| 2003/0035810 A1 | 2/2003 | Caplan | 424/199.1 |
| 2003/0064499 A1 | 4/2003 | Houghton et al. | 435/219 |
| 2003/0108561 A1 | 6/2003 | Bosman et al. | 424/186.1 |
| 2003/0129586 A1 | 7/2003 | Houghton et al. | 435/5 |
| 2003/0152940 A1 | 8/2003 | Sablon et al. | 435/6 |
| 2004/0009937 A1 | 1/2004 | Chen et al. | 514/44 |
| 2004/0072759 A1 | 4/2004 | Gaudemack et al. | 514/15 |
| 2004/0151735 A1 | 8/2004 | Maertens et al. | 424/189.1 |
| 2004/0156858 A1 | 8/2004 | Franzusoff et al. | |
| 2005/0013828 A1 | 1/2005 | George et al. | 424/189.1 |
| 2005/0074465 A1 * | 4/2005 | Houghton | 424/189.1 |
| 2005/0074849 A1 | 4/2005 | Gaudemack et al. | 435/69.1 |

FOREIGN PATENT DOCUMENTS

| | | |
|---|---|---|
| FR | 2486400 | 1/1980 |
| WO | WO 9222571 | 12/1992 |
| WO | WO 02/39951 | 5/2002 |
| WO | WO 2004/005473 | 1/2004 |
| WO | WO 2004/046175 | 6/2004 |
| WO | WO 2004/046176 | 6/2004 |
| WO | WO 2004/058157 | 7/2004 |

OTHER PUBLICATIONS

Matsui et al (2002) Vaccine. 21: 211-220.*
O'Brien et al (2000) Protein Sci. 9: 570-579.*
Lechmann and Liang (2000) Semin Liver Dis. 20(2): 211-26.*
Acosta-Rivero et al., 2002, *Biochemical and Biophysical Research Com.*, 295: 81-84.
Adams et al., 1994, *International Reviews of Immunology*, 11(2): 133-141.
Allsopp et al., 1996, *European Journal of Immunology*, 26(8): 1951-1959.
Bachmann et al., 1994, *Curr. Op. Immunol.*, 6:320-326.
Baker et al., 1988, *Cell*, 54:335-344.
Bizzini et al., 1990, *FEMS Microbiol. Immunol.*, 64:155-168.
Bourdette et al., 1994, *J. Immunol.*, 152:2510-2519.
Brake et al., 1984, *Proc. Natl. Acad. Sci. USA*, 81:4642-4646.
Brossier et al., 1999, *Infection and Immunity*, 67(2): 964-967.
Brown, D., 1995, *The Washington Post*, "Gene Therapy 'Oversold' by Researchers, Journalists".

(Continued)

*Primary Examiner*—Bruce Campell
*Assistant Examiner*—Michelle Horning
(74) *Attorney, Agent, or Firm*—Sheridan Ross P.C.; Angela Dallas Sebor

(57) ABSTRACT

Disclosed are compositions, including vaccines, and methods for vaccinating an animal against hepatitis C virus (HCV) and for treating or preventing hepatitis C viral infection in an animal. The invention includes a variety of novel HCV fusion proteins that can be used directly as a vaccine or in conjunction with a yeast-based vaccine vehicle to elicit an immune response against HCV in an animal. The invention also includes the use of the HCV fusion gene and protein described herein in any diagnostic or therapeutic protocol for the detection and/or treatment or prevention of HCV infection.

42 Claims, 14 Drawing Sheets

OTHER PUBLICATIONS

Chien et al., 1992, *Proc. Natl. Acad Sci. USA.*, 89:10011-10015.
Chou et al., 1994, *J. Immunol.*, 152:2520-2529.
Coghlan, 1995, *New Scientists*, 145:14-15.
Cohen, 1994, *Science*, 264:1660.
Cohen, 1994, *Science*, 264:1839.
Davies et al., 1992, *Nucleic Acids Res.*, 20(11):2693-2698.
Demmer et al., 1993, *J. Immunol.*, 150(12):5371-5378.
Engelhardt et al., 1994, *Hum. Gene Ther*, 5:1217-1229.
Fattal-German et al., 1992, *Develop. Biol. Standard.*, 77:115-120.
Franzusoff et al., 1995, *J. Biol. Chem.*, 270(7):3154-3159.
Fujita et al., 1987, *Bulletin of the World Health Organization*, 65(3):303-308.
Garber et al., 2003, *AIDS Reviews*, 5(3):131-139.
Gnirke et al., 1991, *EMBO J.*, 10(7):1629-1634.
Gobin et al., 1995, *Gene*, 163:27-33.
Hatsuyama et al., 1994, *Plant Cell Physiol.*, 35(1):93-98.
Kaur et al., 2003, *Topics in HIV Medicine*, 11(3): 76-85.
Ketner et al., 1994, *Proc. Natl. Acad. Sci. USA*, 91:6186-6190.
Khu et al., 2004, *Biochem. J.*, 384:401-409.
Layton et al., 1996, *Immunology*, 87(2):171-178.
Markie et al., 1993, *Somat. Cell Mol. Genet.*, 19(2):161-169.
Markland et al., 1997, *Journal of General Virology.*, 78:39-43.
Marshall, 1995, *Science* 269:1050-1055.
Martinez-Donato et al., 2006, *Biochemical and Biophysical Research Comm.*, 342:625-631.
Moore, et al., 1996, *FASEB J.*, 10(6) Abstract 2725.
Moulard et al., 1994, *Eur. J. Biochem.* 225:565-572.
Mullen et al., 1994, *Plant Physiol.*, 105:113 (Abstr. 606).
Mulligan, 1993, *Science*, 260:926-931.
Mustilli et al., 1999, *Res. Microbiol.*, 150:179-187.
Pachnis et al., 1990, *Proc. Natl. Acad. Sci. USA*, 87:5109-5113.
Paglia et al., 1996, *Journal of Experimental Medicine*, 183(1):317-322.
Parolin et al., 2005, *Journal of Biotechnology*, 120:45-58.
Peterson et al., 1993, *Proc. Natl. Acad. Sci. USA*, 90:11207-11211.
Rabinovich et al., 1994, *Science*, 265:1401-1404.
Rosa et al., 1996, *Proc. Natl. Acad. Sci. USA*, 93:1759-1763.
Sanchez-Pescador et al., 1985, *Science*, 227:484-492.
Schreuder et al., 1996 *Vaccine*, 14(5):383-388.
Schupper et al., 1993, *Hepatology*, 18(5):1055-1060.
Sousa et al., 1993, *Journal of Experimental Medicine*, 178(2):509-519.
Stern et al., 1992, *Cell*, 68:465-477.
Suda et al., 1993, *Cell*, 75:1169-1178.
Valenzuela et al., 1985, *Biol Technology*, 3:323-326.
Genpept AAB67036, "polyprotein [Hepatitis C virus strain H77]", Aug. 16, 1997.
Park et al., "Monitoring antibody titers to recombinant Core-NS3 fusion polypeptide is useful for evaluating hepatitis C virus infection and responses to interferon-alpha therapy." Journal of Korean medical science, Apr. 1999, vol. 14, No. 2, pp. 165-170.
Seong et al., "Overexpression and simple purification of a truncated immunologically reative GST-HCV core (1-123) fusion protein", Journal of Virological Methods, May 1996, vol. 59, Nos. 1-2, pp. 13-21.
International Search Report for International (PCT) Patent Application No. PCT/US05/37499, mailed Jan. 11, 2008.
Written Opinion for International (PCT) Patent Application No. PCT/US05/37499, mailed Jan. 11, 2008.

* cited by examiner

E1-E2 Tarmogen

NS4B Tarmogen

FIG. 2
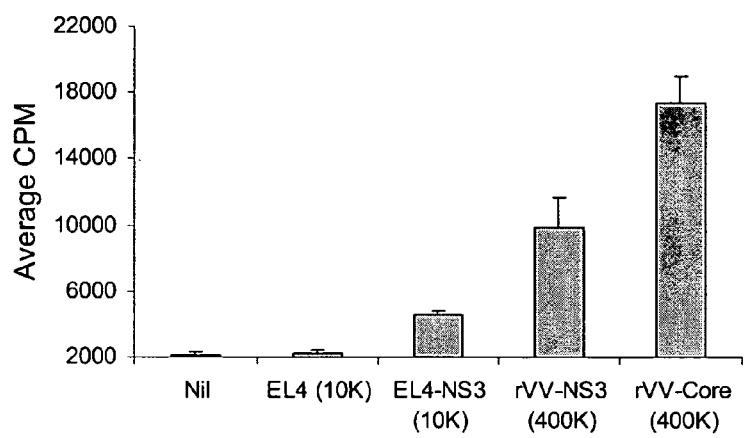
FIG. 3A  FIG. 3B  FIG. 3C
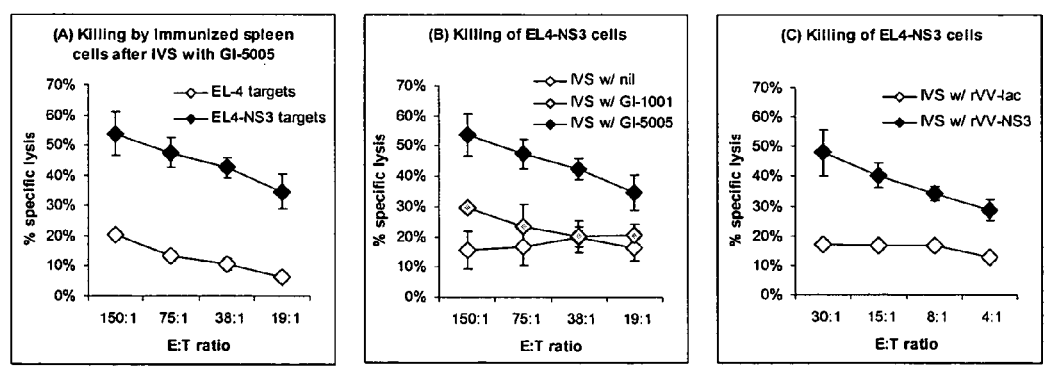

FIG. 4A
FIG. 4B
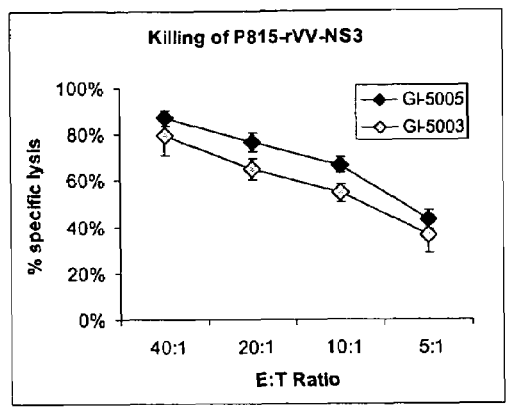
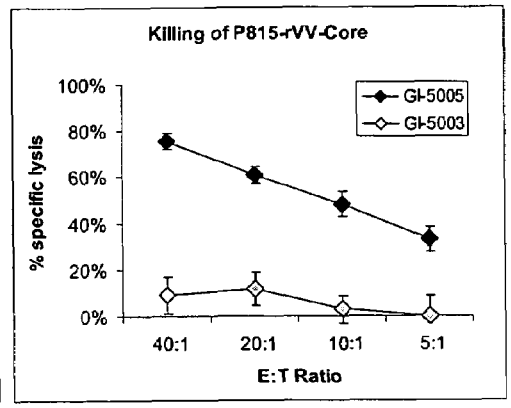
FIG. 5
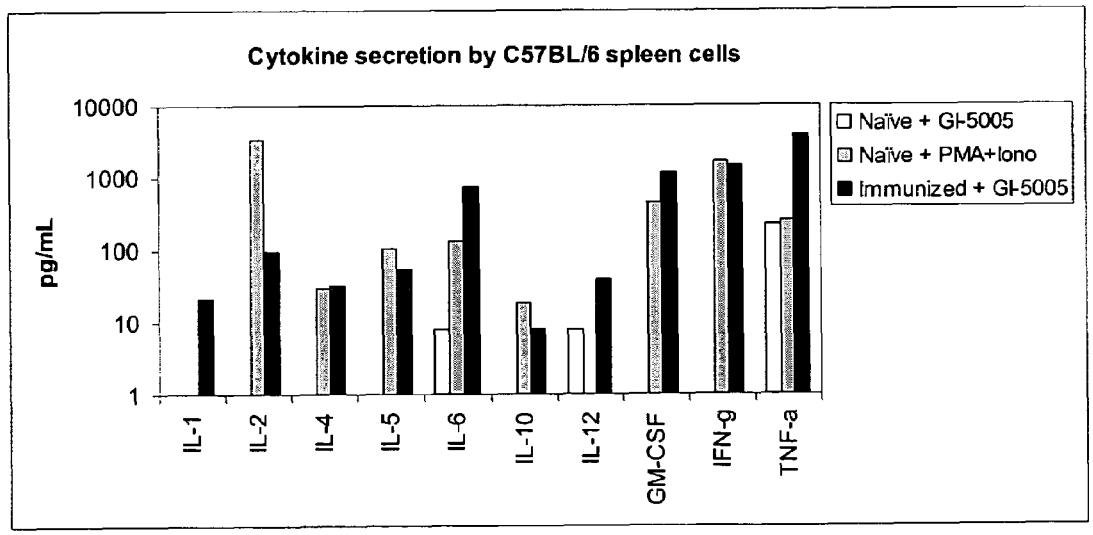

FIG. 6
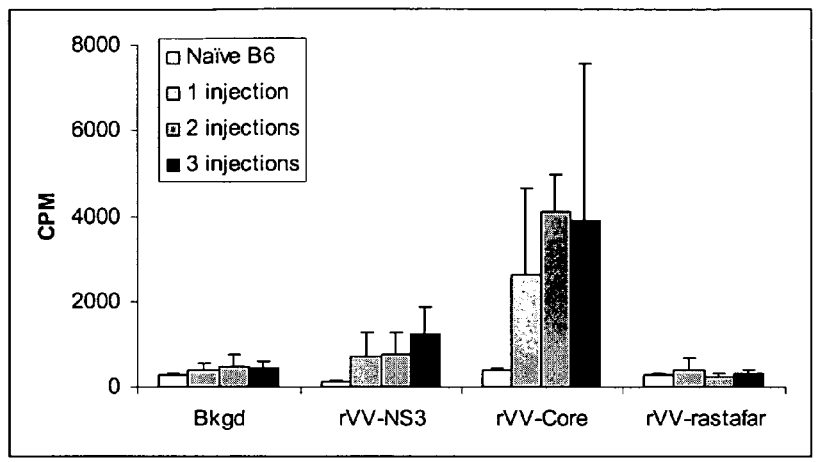
FIG. 7A          FIG. 7B
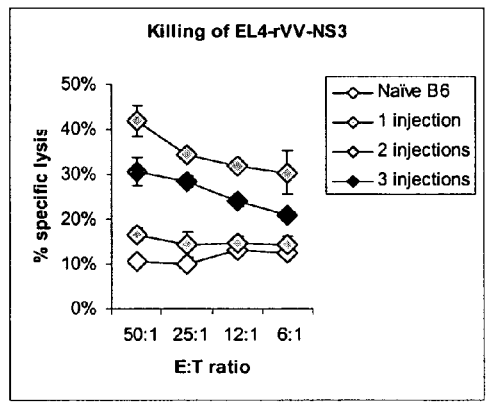 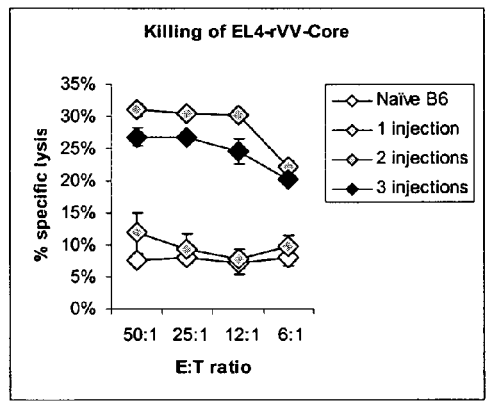
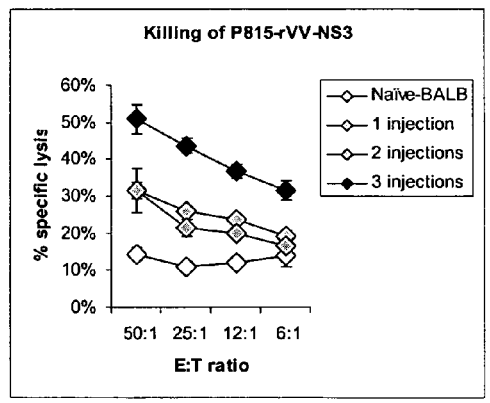 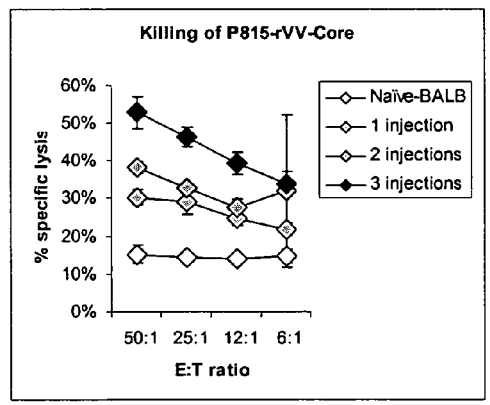
FIG. 7C          FIG. 7D

FIG. 10
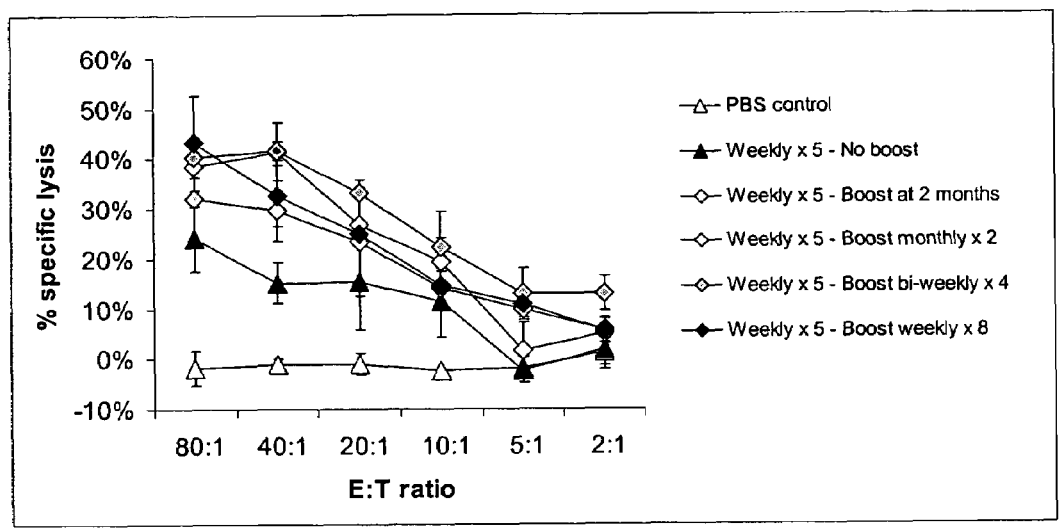
FIG. 11A     FIG. 11B
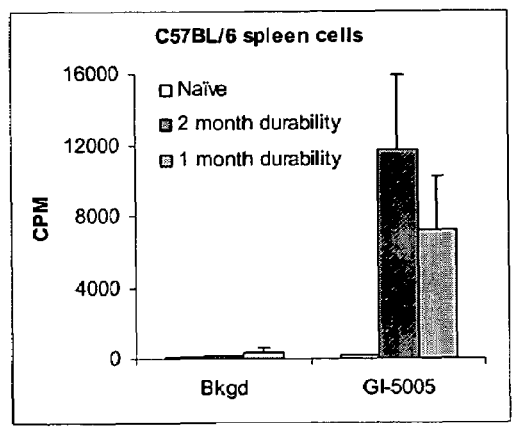 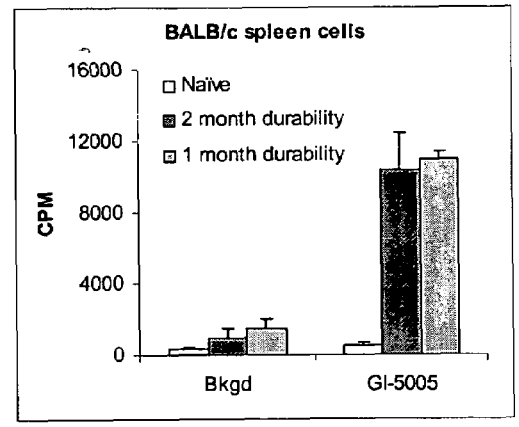

FIG. 12A
FIG. 12B
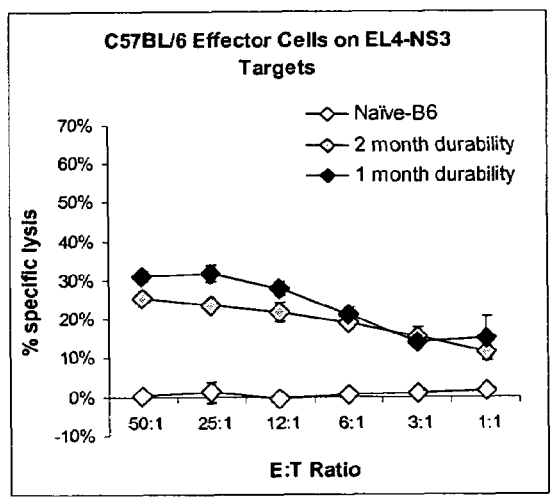
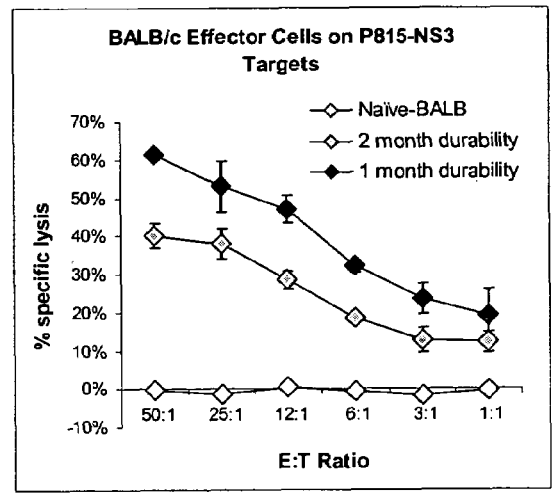

FIG. 15A  FIG. 15B  FIG. 15C
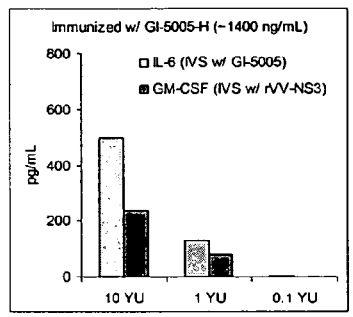 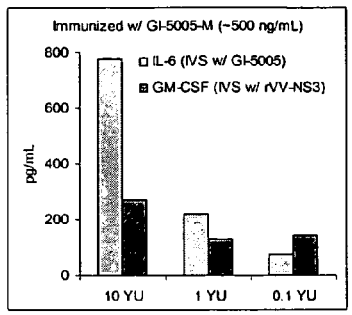 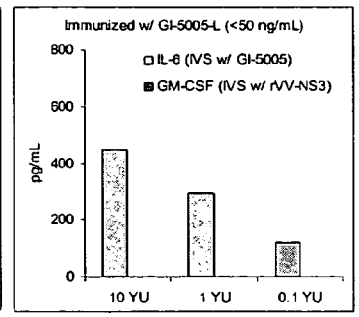
FIG. 16
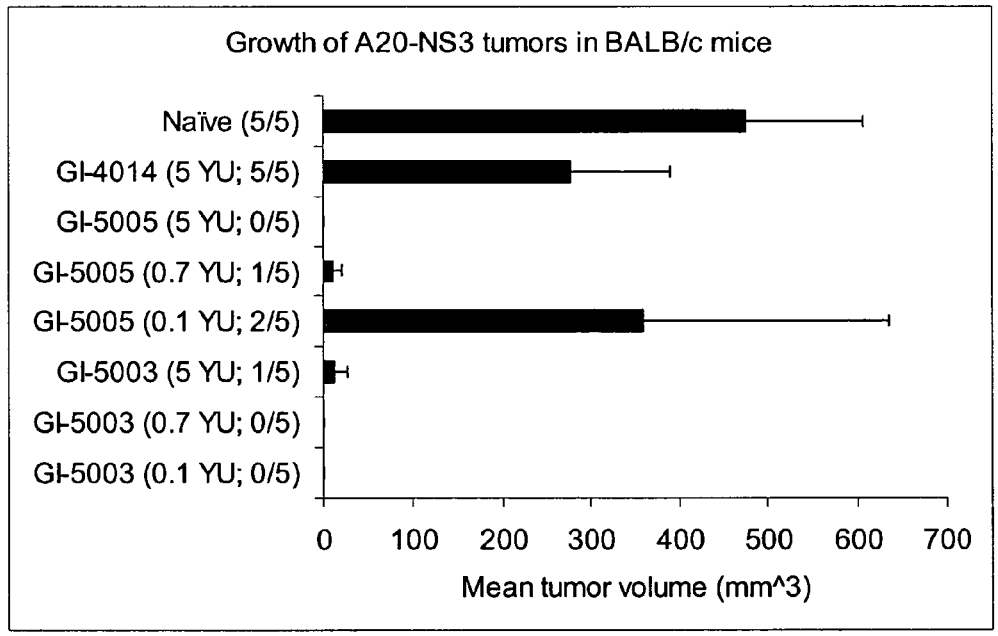

US 7,439,042 B2

YEAST-BASED THERAPEUTIC FOR CHRONIC HEPATITIS C INFECTION

CROSS-REFERENCE TO RELATED APPLICATIONS

This application claims the benefit of priority under 35 U.S.C. § 119(e) from U.S. Provisional Application Ser. No. 60/620,158, filed Oct. 18, 2004. This application also claims priority under 35 U.S.C. § 120 as a continuation-in-part of U.S. patent application Ser. No. 10/738,646, filed Dec. 16, 2003, which claims the benefit of priority under 35 U.S.C. § 119(e) from U.S. Provisional Application Ser. No. 60/434, 163, filed Dec. 16, 2002. The entire disclosure of each of U.S. Provisional Application No. 60/620,158, U.S. patent application Ser. No. 10/738,646 and U.S. Provisional Application Ser. No. 60/434,163 is incorporated herein by reference.

REFERENCE TO SEQUENCE LISTING

This application contains a Sequence Listing submitted on a compact disc, in duplicate. Each of the two compact discs, which are identical to each other pursuant to 37 CFR § 1.52 (e)(4), contains the following file: "Sequence Listing", having a size in bytes of 101 KB, recorded on Oct. 18, 2005. The information contained on the compact disc is hereby incorporated by reference in its entirety pursuant to 37 CFR § 1.77(b)(4).

FIELD OF THE INVENTION

This invention generally relates to compositions and methods for vaccinating an animal against hepatitis C virus (HCV) and for treating or preventing hepatitis C viral infection in an animal.

BACKGROUND OF THE INVENTION

Hepatitis C virus (HCV) is a major causative agent of acute and chronic hepatitis worldwide. It is estimated that there are 200 million chronically HCV-infected individuals worldwide, 4 million of whom reside in the United States. The foremost source of infection is through parenteral routes including blood transfusions or IV drug use. Despite the high degree of safety associated with current blood banking procedures, the rate of infection continues to increase, presumably due to IV drug use and other forms of exposure.

According to data from the Third National Health and Nutrition Examination Survey (NHANES III), approximately 70% of the patients with HCV infections in the United States will become chronically infected. A significant proportion of chronically infected individuals will suffer a serious sequelae of chronic HCV infection including progression to cirrhosis, hepatic decompensation, liver transplant, hepatocellular carcinoma, and death. Retrospective long term follow-up studies on patients chronically infected with HCV estimate the proportion who will progress to cirrhosis at approximately 20% to 50% with follow-up times ranging from 10 to 29 years (1-4). Prospective long term follow-up studies on patients chronically infected with HCV after post-transfusion exposure estimate the proportion who will progress to cirrhosis at approximately 10% to 15% with relatively short follow-up times ranging from 8 to 16 years (5-8). Of those patients who develop cirrhosis secondary to viral infection it is predicted that approximately 1% to 3%, will develop hepatocellular carcinoma annually with an approximate annual mortality rate of 2% to 6% (9-10). An epidemiologic model utilizing NHANES III seroprevalance data and age-specific incidence rates estimates a peak in U.S. population risk for progression to cirrhosis and related complications by 2015, foretelling of a worsening unmet medical need in the near future (11). Interruption of the chronic viral infection using interferon based regimens has been shown in several large series to favorably alter the rates of progression to cirrhosis, hepatocellular, and death (12-14). However, sustained virologic response rates for the treatment of genotype 1 chronic hepatitis C, the predominant genotype found in the U.S., are only approximately 50% with pegylated interferon-α regimens containing ribavirin. Additionally, interferon plus ribavirin based regimens also have significant safety problems including depression, suicidal ideation, flu-like symptoms, and neutropenia. Treatment options are currently limited for partial responders, relapsers, and non-responders to interferon based therapy.

HCV is a member of the Flaviviridae family of enveloped, positive-sense RNA viruses. It has a genome of approximately 9600 nucleotides that is translated upon cell entry into a polyprotein of roughly 3000 amino acids. Three structural and seven non-structural proteins are generated co- and post-translationally by cellular and HCV-derived proteases (Table 1). While the roles of some of the viral proteins have yet to be clearly defined, a number of them, such as the HCV structural Core protein, the E1 and E2 surface glycoproteins, the non-structural NS2 and NS3 proteases, and the NS5B RNA-dependent RNA polymerase are known to perform essential functions in the HCV life cycle. Based on genetic heterogeneity of the viral genomes isolated so far, HCV has 6 major genotypes and more than 100 subtypes.

Genotypes 1a, 1b and 2 are found predominantly in North America and Europe, while in South America, HCV genotypes 1a, 1b, and 3 are prevalent. Genotypes 4, 5 and 6 are observed throughout the rest of the world (19). Despite the geographic predominance of certain HCV genotypes, most genotypes have been identified all over the world due to increased population movement. The different HCV genotypes vary in terms of their response to the currently recommended interferon/ribavirin therapy. In particular, ~50% of patients infected with HCV genotype 1 remain refractory to the current treatment regimen (19). Further, response rates to interferon alpha among African-American patients are lower than those of Caucasian descent. These data suggest the need for alternative treatments that ideally augment the individual's pre-existing cellular immune response.

TABLE 1

HCV genes and gene products

| Gene | Function | % homology between HCV genotypes 1a and 1b |
|------|----------|---------------------------------------------|
| Core | Nucleocapsid core protein | 98.4 |
| E1 | Envelope glycoprotein | 81.8 |

TABLE 1-continued

HCV genes and gene products

| Gene | Function | % homology between HCV genotypes 1a and 1b |
|---|---|---|
| E2 | Envelope glycoprotein | 79.9 |
| P7 | Ion channel | 81.0 |
| NS2 | metalloprotease | 80.1 |
| NS3 | protease/helicase | 92.1 |
| NS4a | NS3 protease co-factor | 91.1 |
| NS4b | Unknown | 82.4 |
| NS5a | Unknown | 77.7 |
| NS5b | RNA-dependent RNA polymerase | 87.5 |

The HCV protein sequences were obtained from the National Center for Biotechnology Information under Accession No. AF011753 (gi: 2327074). The Align program from the Genestream Bioinformatics website (Institut de Génétique Humaine, 141 rue de la Cardonille, Montpellier France) was used to compare the amino acid sequences of the HCV proteins derived from strain 1a and 1b.

Numerous studies suggest that viral replication, the level of viremia and progression to the chronic state in HCV-infected individuals are influenced directly and indirectly by HCV-specific cellular immunity mediated by CD4+ helper ($T_H$) and CD8+ cytotoxic T lymphocytes (CTLs), and directed against both structural and non-structural viral proteins including Core and NS3 (15). The lack of effective immunity in persons with chronic HCV infection is further implied by the occurrence of superinfection with other genotypes of HCV. As the robustness and breadth of cellular immune responses have been suggested to influence the natural course of HCV infection, the development of immunotherapeutic products that stimulate T cell immune responses in virally exposed individuals is of major importance.

Studies of humans and chimpanzees have revealed that HCV can replicate for weeks before the onset of CD4+ and CD8+ T cell responses in blood and liver. Moreover, there may be a delay in the acquisition of function by CD8+ (and perhaps CD4+) T cells even after their expansion in blood (15). The appearance of functional CD8+ T cells is kinetically associated with control of viremia and, at least in some cases, with an elevation in serum transaminases, suggesting that liver damage during acute hepatitis C is immunopathological. At highest risk of persistent HCV infection are those individuals who fail to generate a detectable virus-specific T lymphocyte response in the blood, liver, or both. Perhaps most importantly, generation of a cellular immune response does not necessarily ensure that the infection will be permanently controlled. CD4+ and CD8+ T cell responses must be sustained for weeks or months beyond the point of apparent control of virus replication to prevent relapse and establishment of a persistent infection.

CD4+ T cells play an essential role in anti-HCV immunity by providing help for activating and sustaining CD8+ T cell responses. Protective CD4+ T cells appear to predominantly recognize epitopes in Core, NS3, NS4 and NS5 proteins although responses against the other HCV gene products have also been reported (20-21). In addition to the help that CD4+ T cells provide to CD8+ T cells, it also appears critical that they produce gamma interferon and other pro-inflammatory $T_H1$-, as opposed to, $T_H2$-type cytokines. Equally important for control of chronic infection is the establishment of HCV-specific memory CD4+ T cells (20 & 22).

The finding that CD4+ and CD8+ T cell responses are common to self-limited HCV infections suggests that they cooperate to bring about control of viremia. Memory CD4+ and CD8+ T cells primed during acute resolving hepatitis C infection provide long-term protection from virus persistence in chimpanzees and probably humans. Through antibody-mediated depletion of each memory T cell subset, the chimpanzee model has provided direct proof of the importance of CD8+ T cells in the control of acute hepatitis C and their dependence on CD4+ T cell help (24). In contrast to CD4+ T cells, both acute and memory CD8+ T cells appear to recognize all of the HCV proteins equally and, as with CD4+ T cells, it may be critical that they be capable of producing pro-inflammatory cytokines including gamma interferon (15).

The transition from acute to chronic HCV infection is associated with substantial loss of HCV-specific CD4+ T cells that do not appear to recover during the life of the host. CD8+ T cell activity is also impaired, as it is insufficient for resolution of infection.

A number of experimental approaches to immunotherapy in general have been investigated, including the use of DNA-, recombinant viral-, and autologous dendritic cell-based vaccine strategies. DNA vaccines are good at priming immune responses in humans but are poor at boosting. In contrast, recombinant viruses are good at boosting but suffer from the limitation of vector neutralization. Finally, dendritic cell-based vaccines are patient-specific and labor intensive. Therefore, there remains a need in the art for an effective immunotherapeutic approach against HCV.

SUMMARY OF THE INVENTION

One embodiment of the present invention relates to an isolated fusion protein comprising: (a) at least one hepatitis C virus (HCV) antigen; and (b) a peptide linked to the N-terminus of the HCV antigen. The peptide consists of at least two amino acid residues that are heterologous to the HCV antigen, wherein the peptide stabilizes the expression of the fusion protein in a yeast or prevents posttranslational modification of the expressed fusion protein; wherein the amino acid residue at position one of the fusion protein is a methionine; wherein the amino acid residue at position two of the fusion protein is not a glycine or a proline; wherein none of the amino acid residues at positions 2-6 of the fusion protein is a methionine; and, wherein none of the amino acid residues at positions 2-6 of the fusion protein is a lysine or an arginine. In one aspect, the peptide consists of at least 2-6 amino acid residues that are heterologous to the HCV antigen. In another aspect, the peptide comprises an amino acid sequence of M-$X_2$-$X_3$-$X_4$-$X_5$-$X_6$; wherein $X_2$ is any amino acid except glycine, proline, lysine or arginine; wherein $X_3$ is any amino acid except methionine, lysine or arginine; wherein $X_4$ is any amino acid except methionine, lysine or arginine; wherein $X_5$ is any amino acid except methionine, lysine or arginine; and wherein $X_6$ is any amino acid except methionine, lysine or arginine. In one aspect, $X_6$ is a proline. In one aspect, the peptide comprises an amino acid sequence of M-A-D-E-A-P (SEQ ID NO:9).

In one aspect of this embodiment of the invention, the HCV antigen further comprises a peptide linked to the C-terminus and comprising at least two amino acid residues that are heterologous to the HCV antigen, wherein the peptide stabilizes the expression of the fusion protein in a yeast or prevents posttranslational modification of the expressed fusion protein. In one aspect, the peptide linked to the C-terminus comprises the amino acid sequence of E-D.

In yet another aspect of this embodiment of the invention, the HCV antigen further comprises a peptide linked to the C-terminus of the HCV antigen, wherein the peptide allows for recognition of the fusion protein by an antibody directed against the peptide. In one aspect, the peptide linked to the C-terminus comprises an amino acid sequence of G-G-G-H-H-H-H-H-H (SEQ ID NO:10).

In another aspect of this embodiment of the invention, the HCV fusion protein is encoded by a nucleic acid molecule comprising the nucleic acid sequence A-C-C-A-T-G-G (SEQ ID NO:21) at the 5' end, wherein the A-T-G within this nucleic acid sequence is the translational start codon for the synthetic peptide.

Another embodiment of the present invention relates to an isolated fusion protein comprising: (a) at least one HCV antigen; and (b) a yeast protein linked to the N-terminus of the HCV antigen, wherein the yeast protein consists of between about two and about 200 amino acids of an endogenous yeast protein, wherein the yeast protein stabilizes the expression of the fusion protein in a yeast or prevents posttranslational modification of the expressed fusion protein. In one aspect, the yeast protein comprises an antibody epitope for identification and purification of the fusion protein, including, but not limited to, the amino acid sequence of G-G-G-H-H-H-H-H-H (SEQ ID NO:10).

In any of the above-identified embodiments of the invention, the fusion protein can comprise at least a portion of an HCV protein selected from: HCV E1 envelope glycoprotein, HCV E2 envelope glycoprotein, HCV P7 ion channel, HCV NS2 metalloprotease, HCV NS3 protease/helicase, HCV NS4a NS3 protease cofactor, HCV NS4b, HCV NS5a, and HCV NS5b RNA-dependent RNA polymerase, wherein said portion of an HCV protein is linked to at least a portion of an HCV Core sequence. In any of the above-identified embodiments of the invention, the fusion protein can comprise at least two or more HCV antigens. In any of the above-identified embodiments of the invention, the fusion protein can comprise at least one or more immunogenic domain of one or more HCV antigens.

Another embodiment of the present invention relates to an isolated nucleic acid molecule comprising a nucleic acid sequence encoding any of the above-described fusion proteins. In one embodiment, the expression of the fusion protein is under the control of an inducible promoter, such as CUP1.

Another embodiment of the present invention relates to a recombinant nucleic acid molecule comprising any of such isolated nucleic acid molecules. In one embodiment, the recombinant nucleic acid molecule is a viral vector.

Yet another embodiment of the invention relates to a recombinant cell that has been transfected with any of the recombinant nucleic acid molecules described herein. Such a cell can include, but is not limited to, a tumor cell.

Another embodiment of the present invention relates to a vaccine comprising: (a) a yeast vehicle; and (b) an HCV fusion protein as described above.

Another embodiment of the present invention relates to a vaccine comprising: (a) an HCV fusion protein as described above; and (b) a pharmaceutically acceptable carrier.

Yet another embodiment of the present invention relates to a vaccine comprising: (a) a dendritic cell; and (b) an HCV fusion protein as described above. Such a vaccine can further comprise a yeast vehicle, wherein the dendritic cell also contains the yeast vehicle.

Yet another embodiment of the present invention relates to a vaccine comprising an isolated nucleic acid molecule encoding an HCV fusion protein as described above.

Any of the above-described vaccines of the invention can also include at least one biological response modifier. Such biological response modifiers can include, but are not limited to: a cytokine, a hormone, a lipidic derivative, and a small molecule drug. Such biological response modifiers can include, but are not limited to: anti-CTLA-4, anti-CD137, anti-CD28, anti-CD40, alemtuzumab, denileukin diftitox, anti-CD4, anti-CD25, anti-PD1, anti-PD-L1, anti-PD-L2, FOXP3-blocking agents, Flt-3 ligand, imiquimod, granulocyte-macrophage colony-stimulating factor (GM-CSF), sargramostim, Toll-like receptor (TLR)-7 agonists, and TLR-9 agonists.

Another embodiment of the present invention, relates to a method to protect an animal against hepatitis C virus (HCV) infection, comprising administering to an animal that has been infected with HCV or is at risk of being infected with HCV, any of the vaccines of the present invention as described herein, wherein administration of the vaccine to the animal reduces or prevents HCV infection or at least one symptom resulting from HCV infection in the animal.

Yet another embodiment of the present invention relates to a method to elicit an antigen-specific, cell-mediated immune response against an HCV antigen, comprising administering to an animal any of the vaccines of the present invention as described herein.

In either of the above methods, the vaccine can be administered as a booster to a vaccine comprising a viral vector encoding an HCV antigen. In either of the above-methods, the vaccine can be administered to prime the immune system prior to boosting with a different HCV vaccine.

BRIEF DESCRIPTION OF THE DRAWINGS OF THE INVENTION

FIG. 2 is a graph illustrating that a vaccine of the invention expressing a truncated NS3-Core fusion protein induces NS3- and Core-specific lymphocyte proliferation.

FIGS. 3A-3C are graphs illustrating that a vaccine of the invention expressing a truncated NS3-Core fusion protein induces NS3-specific cytotoxic effector cells.

FIGS. 4A and 4B are graphs demonstrating that a vaccine of the invention expressing a truncated NS3-Core fusion protein induces cytotoxic effector cells that kill tumor cells infected with recombinant vaccinia virus encoding HCV NS3 or Core.

FIG. 5 is a graph illustrating that a vaccine of the invention expressing a truncated NS3-Core fusion protein induces secretion of pro-inflammatory cytokines by mouse splenocytes.

FIG. 6 is a graph showing proliferating lymphocytes induced by one, two or three weekly immunizations with a vaccine of the invention expressing a truncated NS3-Core fusion protein.

FIGS. 7A-7D are graphs showing the cytotoxic effector cell activity induced by one, two or three weekly immunizations with a vaccine of the invention expressing a truncated NS3-Core fusion protein.

FIG. 10 is a graph illustrating cytotoxic effector cell activity in spleen effector cells derived from the BALB/c mice that were immunized and boosted with a vaccine of the invention expressing a truncated NS3-Core fusion protein under different immunization protocols.

FIGS. 11A and 11B are graphs demonstrating the durability of lymphocyte proliferative responses induced with a vaccine of the invention expressing a truncated NS3-Core fusion protein.

FIGS. 12A and 12B are graphs showing the durability of cytotoxic effector cell responses induced with a vaccine of the invention expressing a truncated NS3-Core fusion protein.

FIGS. 15A-15C are graphs showing pro-inflammatory cytokine secreting cells induced with a vaccine of the invention expressing different amounts of a truncated NS3-Core fusion protein.

FIG. 16 is a graph showing that vaccines of the invention expressing a truncated NS3-Core fusion protein or an inactivated HCV NS3 protease fusion protein induces protective immunity in BALB/c mice against challenge with syngeneic tumor cells expressing HCV NS3.

DETAILED DESCRIPTION OF THE INVENTION

Figure 1A:
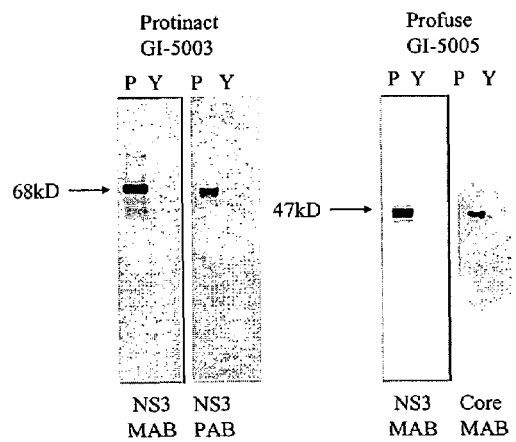
FIGS. 1A and 1B are digital images of a Western blot (FIG. 1A) and Coomassie stain (FIG. 1B) showing expression of a truncated NS3-Core fusion protein and an inactivated HCV NS3 fusion protein in yeast vehicles according to the present invention.

This invention generally relates to compositions and methods for vaccinating an animal against hepatitis C virus (HCV) and for treating or preventing hepatitis C viral infection in an animal. The invention includes the use of a particular yeast-based vaccine comprising a yeast vehicle and an HCV antigen fusion protein that is selected to elicit an immune response against HCV infection in an animal. The invention also includes the use of the HCV fusion gene and protein described herein in any vaccine and vaccine protocol for HCV.

Clinical evidence suggests that clearance and control of hepatitis C virus (HCV) infection is facilitated by cell-mediated immunity and that enhancement of immunity in chronically-infected individuals may have therapeutic benefits. Previous studies reported by the present inventors and others have shown the potential for using whole, recombinant $S.$ $cerevisiae$ yeast as a vaccine and immunotherapy vector (e.g., see U.S. Pat. No. 5,830,463, issued Nov. 3, 1998, U.S. patent application Ser. No. 09/991,363, filed Nov. 15, 2001, each of which is incorporated herein by reference in its entirety). The present inventors' yeast-based immunotherapeutic products have been shown to elicit immune responses that are capable of killing target cells expressing a variety of viral and cancer antigens in vivo, in a variety of animal species, and to do so in an antigen-specific, $CD8^+$ CTL-mediated fashion (16-17).

The present invention is directed to an improvement on the platform technology related to yeast-based immunotherapeutic products as described in U.S. Pat. No. 5,830,463, issued Nov. 3, 1998; U.S. patent application Ser. No. 09/991,363, filed Nov. 15, 2001. The present inventors have previously shown that $S.$ $cerevisiae$ are avidly phagocytosed by and directly activate dendritic cells which then present yeast-associated proteins to CD4 and CD8 T cells in a highly efficient manner (Stubbs et al. $Nature$ $Med.$ 5:625-629, 2001; and U.S. patent application Ser. No. 09/991,363, supra). $S.$ $cerevisiae$ that express mutant Ras oncoproteins were shown to specifically eliminate established tumors bearing the homologous mutations in a mouse model of spontaneous lung cancer (Lu et al., $Cancer$ $Research$ 64:5084-5088, 2004) and this approach is currently being tested in a phase 1 human clinical trial in patients with pancreatic, lung and colorectal cancer. Immunotherapeutic products based on this platform technology are straightforward to produce, are not neutralized by host immune responses, can be administered repeatedly to boost antigen-specific immune responses, and do not require a patient-specific approach for manufacturing.

More particularly, and by way of example, the present inventors have developed a yeast-based vaccine that comprises a recombinant heat-inactivated $S.$ $cerevisiae$ yeast expressing a novel HCV fusion protein, which in one embodiment, contains at least a portion of both NS3 and Core protein sequences. Other embodiments include a novel full-length inactivated NS3 HCV protein, a novel truncated E1-E2 fusion protein, and a novel TM domain-deleted HCV NS4b fusion protein. Other embodiments of the invention will be apparent in view of the disclosure provided herein.

The HCV Core protein and NS3 protease are abundantly expressed in HCV-infected cells and are essential for virus replication; these characteristics combined with the high degree of sequence conservation make them excellent targets for immunotherapy. The vaccine of the present invention has been shown in animals to generate both antigen specific proliferative T cell responses as well as cytotoxic T cell (CTL) responses against virally infected cells expressing both NS3 and Core antigens and to protect animals against tumors expressing HCV antigens (see Examples and 18). Administration of the vaccine is expected to augment the HCV-specific $CD4^+$ and $CD8^+$ T cell response targeted to the HCV NS3 and Core proteins, result in a reduction of viral load, and ultimately lead to viral clearance in HCV-infected individuals.

The novel HCV fusion protein that is used as a component of the yeast-based vaccine of the present invention is produced using a novel construct for expression of heterologous antigens in yeast, wherein the desired antigenic protein(s) or peptide(s) are fused at their amino-terminal end to: (a) a specific synthetic peptide described herein; or (b) at least a portion of an endogenous yeast protein, wherein either fusion partner provides significantly enhanced stability of expression of the protein in the yeast and/or a prevents post-translational modification of the proteins by the yeast cells. Also, the fusion peptides provide an epitope that can be designed to be recognized by a selection agent, such as an antibody, and do not appear to negatively impact the immune response against the vaccinating antigen in the construct. Such agents are useful for the identification, selection and purification of proteins useful in the invention.

In addition, the present invention contemplates the use of peptides that are fused to the C-terminus of the antigen construct, particularly for use in the selection and identification of the protein. Such peptides include, but are not limited to, any synthetic or natural peptide, such as a peptide tag (e.g., 6× His) or any other short epitope tag. Peptides attached to the C-terminus of an antigen according to the invention can be used with or without the addition of the N-terminal peptides discussed above.

Finally, the present inventors describe herein several different novel fusion protein HCV antigens for use in a yeast-based vaccine that provide multiple (two or more) immunogenic domains from one or more antigens within the same construct. An exemplary fusion protein comprising multiple immunogenic domains is the fusion protein comprising the HCV NS3 and Core proteins, or immunogenic portions thereof, that is described herein. Others are also described below.

As described above, NS3 and Core are abundantly expressed in infected cells, are required for viral replication and contain epitopes that are recognized by both $CD4^+$ and $CD8^+$ T cells in acute and chronic infection. An additional advantage of targeting these proteins, and particularly both proteins in a single vaccine, is the high degree of conservation at the amino acid level. Both the Core and NS3 proteins are highly conserved among HCV genotypes 1a and 1b, the HCV strains most prevalent in the U.S. (Table 1). The Core protein displays a 98% amino acid identity among strains 1a and 1b, and identities ranging from 86-95% for the other five HCV genotypes are observed compared to the HCV 1a protein sequence. The NS3 protein is also highly conserved among the different HCV strains—a 92% amino acid identity exists between strains 1a and 1b and identities range from 81-86% for the other HCV genotypes compared to the HCV 1a protein sequence. The high degree of conservation of the Core and NS3 proteins among the various HCV genotypes signals the essential nature of specific overall protein domains for viral function. One vaccine of the present invention, despite being a single product, was designed to target two viral antigens, NS3 protease and Core protein. This approach can readily be expanded to incorporate the protein sequences of other essential and conserved HCV viral proteins to result in an even broader cellular immune response. Such additional fusion proteins and vaccines are exemplified herein.

The nucleic acid and amino acid sequence for HCV polyprotein genes and the polyproteins encoded thereby are known in the art. For example, the nucleic acid sequence of the polyprotein gene for Hepatitis C Virus strain H77 is described in Database Accession No. AF011753 (gi: 2327074) and is represented hereinby SEQ ID NO:19. SEQ ID NO:19 encodes the HCV strain H77 polyprotein, which has an amino acid sequence represented herein by SEQ ID NO:20. Within SEQ ID NO:20, the HCV proteins comprise the following positions: HCV Core (positions 1 to 191 of SEQ ID NO:20); HCV E1 envelope glycoprotein (positions 192 to 383 of SEQ ID NO:20); HCV E2 envelope glycoprotein (positions 384 to 746 of SEQ ID NO:20); HCV P7 ion channel (positions 747 to 809 of SEQ ID NO:20); HCV NS2 metalloprotease (positions 810 to 1026 of SEQ ID NO:20); HCV NS3 protease/helicase (positions 1027 to 1657 of SEQ ID NO:20); HCV NS4a NS3 protease cofactor (positions 1658 to 1711 of SEQ ID NO:20); HCV NS4b (positions 1712 to 1972 of SEQ ID NO:20); HCV NS5a (positions 1973 to 2420 of SEQ ID NO:20); and HCV NS5b RNA-dependent RNA polymerase (positions 2421 to 3011 of SEQ ID NO:20). As discussed above, strains of HCV display high amino acid identity (e.g., see Table 1). Therefore, using the guidance provided herein and the reference to the exemplary HCV strain, one of skill in the art will readily be able to a variety of HCV-based fusion proteins from any HCV strain for use in the compositions and vaccines of the present invention.

It is clear that control and clearance of HCV requires both $CD4^+$ and $CD8^+$ T cells and that the lack of adequate cellular immunity is associated with development of chronic infection. It is appealing therefore, to propose that stimulation of existing but insufficient HCV-specific $CD4^+$ and $CD8^+$ T cells in chronically HCV infected individuals will have a therapeutic benefit. Without being bound by theory, the present inventors believe that the ideal HCV immunotherapy consists of a non-pathogenic vector that can deliver antigens into the MHC class I and class II antigen presentation pathways to stimulate potent $CD4^+$ and $CD8^+$ T cell responses. This vector should also be capable of repeated administration, similar to other therapeutic products. The vaccine and compositions of the present invention are ideally suited to these goals.

Some immunotherapeutic vaccine preparations known prior to the present invention consisted of purified viral proteins that are endocytosed by dendritic cells and macrophages (also referred to generally herein as antigen presenting cells or APCs). The proteins in the engulfed material are digested into polypeptides (10-20 amino acids) which are bound to class II MHC molecules in specialized endosomes in APCs. The peptide+class II MHC molecule complex is then expressed on the surface of the APC. An antigen-specific $CD4^+$ helper T cell ($T_H$) binds to the combination of class II MHC+peptide, becomes activated and produces lymphokines.

Soluble antigens that are administered extracellularly without adjuvants tend to stimulate type 2 helper T cells ($T_H2$), which produce lymphokines that act on B cells leading to a humoral immune response. $T_H2$ responses tend to inhibit type 1 helper T cell ($T_H1$) responses that are important for induction of cell-mediated immunity. If the viral antigen being targeted is on the membrane of the infected cell, approaches that generate antibodies could have a therapeutic effect. However, if the viral antigen being targeted is found inside the infected cell, antibody generally has little effect. In addition, and because of the bias towards a $T_H2$ response, $CD8^+$ CTL are not normally activated in response to exogenously introduced protein antigens. If $CD8^+$ CTL are required for protection against chronic viral infection, it seems reasonable to postulate that approaches employing recombinant proteins may prove to be unsuccessful.

In contrast to extracellular antigens, $CD8^+$ CTL are induced in response to any antigen that is being synthesized by the cell to be targeted. These antigens are referred to as endogenous antigens. Viral proteins being synthesized by infected cells are digested into peptides (8-10 amino acids) by cytosolic proteasomes coupled with peptide delivery into the endoplasmic reticulum. Proper folding of class I MHC molecules in the endoplasmic reticulum is dependent on binding of proteasome-generated peptides, prior to trafficking to the surface of the infected or tumor cell. CD8+ T cells respond to the combination of MHC I receptor-peptide complexes and produce lymphokines including IFN-γ which, in general, lead to a cell-mediated immune response, including killing of the infected cell.

CTL appear to require IL-2 and IL-12 in order to be effectively activated. While CD8+ CTL can produce some IL-2, it is generally accepted that CD4+ $T_H1$ cells are the major sources of IL-2 for CTL-mediated responses. IL-12 is produced by dendritic cells and macrophages. In addition, it is also clear that in order to obtain maximal CTL activation, presentation of antigens by dendritic cells is required. Thus, as for CD4+ $T_H1$ cells, CTL require interaction with an antigen presenting cell (APC) in order to become maximally activated and then respond to virally-infected cells.

It was initially unclear how antigens being synthesized by a virally-infected cell could find their way into the class I MHC pathway in dendritic cells, unless the dendritic cell itself became infected. However, recent data indicates that dendritic cells can recognize infected cells that become apoptotic as a result of infection and that "cross-priming" (delivery of exogenous antigens into the endogenous antigen presentation pathway) can occur such that some of the proteins associated with cells/particles engulfed by dendritic cells and macrophages find their way into the class I MHC pathway (23). In addition, certain "danger" signals (described below) can enhance this process (25).

Immune responses are initiated primarily by dendritic cells and macrophages that take up foreign material from extracellular fluids. A method to increase the ability of these cells to adequately present antigens should lead to an improved T cell-mediated cellular immune response. In this regard, recombinant *S. cerevisiae* yeast exhibit the particulate features of immunostimulatory complexes (ISCOMs) (26) with the added advantage that richly glycosylated yeast possess natural adjuvant-like properties and can be readily engineered to express multiple antigens (16, 27-29). *S. cerevisiae* yeast cells are avidly taken up by professional antigen-presenting cells including macrophages and dendritic cells. Yeast-associated proteins are efficiently presented via both class I and class II MHC leading to protective antigen-specific CTL-mediated immunity to tumor cells (16-17).

Dendritic cells and macrophages have a variety of receptors on their surface that act as microbial pattern recognition molecules; i.e., they recognize pathogens on the basis of differences in glycosylation patterns, lipoproteins and nucleic acid composition. Hence, such antigen presenting cells (APCs) have receptors for microbial mannoproteins, peptidoglycans, glucans, lipoproteins, double-stranded RNA and CpG island-containing DNA (30-32). Engagement of these receptors results in what has been termed a "danger" signal leading to dendritic cell maturation, activation, enhanced phagocytosis, and efficient presentation of antigens that were associated with the engaging material (33).

In fact, dendritic cells and macrophages may have more receptors that recognize yeast than any other microbe. These receptors include TLR-2, TLR-4, TLR-6, CD14, Dectin-1, Dectin-2, DEC-205 and the mannose receptor family (30, 34). Uptake of zymosan, a crude *Saccharomyces cerevisiae* yeast cell wall preparation, results in up-regulation of a multitude of pro-inflammatory genes (35). The present inventors' data indicate that uptake of whole yeast by mouse and human dendritic cells and macrophages results in upregulation of a variety of cell surface molecules including adhesion molecules (ICAM-1, CD54), co-stimulatory molecules (B7-1, B7-2, CD80, CD86), and class I and class II MHC molecules, as well as promoting the secretion of pro-inflammatory $T_H1$-type cytokines, such as TNF-α, GM-CSF, interferon-γ, IL-2 and IL-12.

In addition to being able to interact directly with dendritic cells, yeast have a variety of other characteristics that make them an ideal platform for immunotherapy. First, multiple antigens may be engineered for expression within a single yeast strain (29), and these formulations share many advantages with DNA vaccines, including ease of construction and the ability to target multiple antigens. Unlike DNA vaccines, yeast-based immunotherapeutic formulations do not require extensive purification to remove potentially toxic contaminants. As will be described in further detail below, the heterologous proteins expressed in recombinant yeast serve as antigens for potent CD8+ CTL-mediated immune responses in vitro and in vivo (16-17). In animal trials as preventative, as well as therapeutic treatments, the yeast formulation was successful at protecting and treating immunized animals from tumor growth (16-17). These results suggest that the vaccines of the present invention could be effective for eliciting broad-spectrum immune responses as an HCV immunotherapeutic.

In the present invention, the present inventors have generated a novel recombinant yeast immunotherapeutic, also referred to herein as GI-5005, that expresses an HCVNS3-Core fusion protein under the control of an inducible promoter. Immunoblot analysis of GI-5005 cell lysates using NS3—or Core-specific antibodies reveal a 47 kD protein. The GI-5005 yeast produce greater than 5 μg of the HCV fusion protein per 10 million cells. Injection of GI-5005 yeast in C57BL/6 and BALB/c mice resulted in induction of potent NS3 and Core antigen-specific helper and cytotoxic T cell immune responses as shown by lymphocyte proliferation, cytotoxicity and cytokine release assays. Mice that were vaccinated with GI-5000 series yeast were protected from challenge with HCV antigen-expressing syngeneic tumor cells. Immunogenicity and tumor protection results, as well as results in a surrogate model of therapy are also presented herein. Finally, a phase 1 trial in chronically HCV infected patients will be described.

Vaccines and Compositions of the Invention

One embodiment of the present invention relates to a composition (vaccine) which can be used in a method to protect an animal against a HCV infection or disease resulting therefrom or to alleviate at least one symptom resulting from the HCV infection. The composition or vaccine. The vaccine comprises: (a) a yeast vehicle; and (b) a heterologous fusion protein expressed by the yeast vehicle. As discussed above, the invention includes several improved HCV fusion proteins for use as antigens in the vaccines of the invention, wherein such vaccines may include yeast vehicles, although other vaccines that do not include yeast vehicles are also contemplated by the present invention (see below). Specifically, the present invention provides new fusion protein constructs that stabilize the expression of the heterologous protein in the yeast vehicle, prevent posttranslational modification of the expressed heterologous protein, and/or that can be used as vaccinating antigens in the absence of the yeast vehicle described herein (i.e., in conventional or other non-yeast-based vaccine compositions). The novel fusion proteins, in some embodiments, also provide a broad cellular immune response by the use of multiple selected antigens in a single vaccine. In conjunction with the yeast vehicle, these fusion proteins are most typically expressed as recombinant proteins by the yeast vehicle (e.g., by an intact yeast or yeast spheroplast, which can optionally be further processed to a yeast cytoplast, yeast ghost, or yeast membrane extract or fraction thereof), although it is an embodiment of the invention that one or much such fusion proteins could be loaded into a yeast vehicle or otherwise complexed or mixed with a yeast vehicle as described above to form a vaccine of the present invention.

One such fusion construct useful in the present invention is a fusion protein that includes: (a) at least one HCV antigen (including immunogenic domains and epitopes of a full-length antigen, as well as various fusion proteins and multiple antigen constructs as described elsewhere herein); and (b) a synthetic peptide.

In one embodiment, the synthetic peptide linked to the N-terminus of the HCV antigen, the peptide consisting of at least two amino acid residues that are heterologous to the HCV antigen, wherein the peptide stabilizes the expression of the fusion protein in the yeast vehicle or prevents posttranslational modification of the expressed fusion protein. The synthetic peptide and N-terminal portion of the antigen together form a fusion protein that has the following requirements: (1) the amino acid residue at position one of the fusion protein is a methionine (i.e., the first amino acid in the synthetic peptide is a methionine); (2) the amino acid residue at position two of the fusion protein is not a glycine or a proline (i.e., the second amino acid in the synthetic peptide is not a glycine or a proline); (3) none of the amino acid residues at positions 2-6 of the fusion protein is a methionine (i.e., the amino acids at positions 2-6, whether part of the synthetic peptide or the protein, if the synthetic peptide is shorter than 6 amino acids, do not include a methionine); and (4) none of the amino acids at positions 2-6 of the fusion protein is a lysine or an arginine (i.e., the amino acids at positions 2-6, whether part of the synthetic peptide or the protein, if the synthetic peptide is shorter than 5 amino acids, do not include a lysine or an arginine). The synthetic peptide can be as short as two amino acids, but is more preferably at least 2-6 amino acids (including 3, 4, 5 amino acids), and can be longer than 6 amino acids, in whole integers, up to about 200 amino acids.

In one embodiment, the peptide comprises an amino acid sequence of M-$X_2$-$X_3$-$X_4$-$X_5$-$X_6$, wherein M is methionine; wherein $X_2$ is any amino acid except glycine, proline, lysine or arginine; wherein $X_3$ is any amino acid except methionine, lysine or arginine; wherein $X_4$ is any amino acid except methionine, lysine or arginine; wherein $X_5$ is any amino acid except methionine, lysine or arginine; and wherein $X_6$ is any amino acid except methionine, lysine or arginine. In one embodiment, the $X_6$ residue is a proline. An exemplary synthetic sequence that enhances the stability of expression of an HCV antigen in a yeast cell and/or prevents post-translational modification of the protein in the yeast includes the sequence M-A-D-E-A-P (SEQ ID NO:9). In addition to the enhanced stability of the expression product, the present inventors believe that this fusion partner does not appear to negatively impact the immune response against the vaccinating antigen in the construct. In addition, the synthetic fusion peptides can be designed to provide an epitope that can be recognized by a selection agent, such as an antibody.

In another embodiment of the invention, the nucleic acids that encode the translation start site of a synthetic peptide used in the invention are A-C-C-A-T-G-G, (SEQ ID NO:21) in accordance with Kozak translation sequence rules, where the ATG in this sequence is the initial translation start site and encodes the methionine of M-A-D-E-A-P (SEQ ID NO:9).

It is to be understood that various embodiments of the invention as described herein may also be combined. For example, in one aspect of the invention, when the synthetic peptide is M-A-D-E-A-P (SEQ ID NO:9), the nucleic acids encoding the start site for this peptide can be A-C-C-A-T-G-G (SEQ ID NO:10) as described above. Various other combinations of embodiments of the invention will be apparent to those of skill in the art.

Another specific embodiment of the present invention that is similar to the embodiment above and that can include the limitations of the embodiment above (although this is not required) includes a vaccine comprising: (iii) a peptide linked to the C-terminus of the HCV antigen, the peptide consisting of at least two amino acid residues that are heterologous to the HCV antigen, wherein the peptide stabilizes the expression of the fusion protein in the yeast vehicle or prevents posttranslational modification of the expressed fusion protein. In one exemplary aspect of the invention, the peptide comprises an amino acid sequence of E-D (Glu-Asp). Such a sequence works to counteract hydrophobicity.

According to the present invention, "heterologous amino acids" are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Therefore, at least two amino acid residues that are heterologous to the HCV antigen are any two amino acid residues that are not naturally found flanking the HCV antigen.

Another embodiment of the present invention relates to a composition (vaccine) that can be used for protecting an animal against HCV infection or a symptom resulting from such infection comprising: (a) a yeast vehicle; and (b) a heterologous fusion protein expressed by the yeast vehicle. In one embodiment, the fusion protein comprises: (i) at least one HCV antigen (including immunogenic domains and epitopes of a full-length antigen, as well as various fusion proteins and multiple antigen constructs as described elsewhere herein) that is fused to (ii) a yeast protein linked to the N-terminus of the HCV antigen, wherein the yeast protein consists of between about two and about 200 amino acids of an endogenous yeast protein, wherein the yeast protein provides significantly enhanced stability of the expression of the fusion protein in the yeast vehicle or prevents posttranslational modification of the expressed fusion protein by the yeast cells. In addition, the endogenous yeast antigen, as with the synthetic peptide, this fusion partner does not appear to negatively impact the immune response against the vaccinating antigen in the construct. This aspect of the invention may be used in connection with other embodiments of the invention described above.

The endogenous yeast protein consists of between about two and about 200 amino acids (or 22 kDa maximum) of an endogenous yeast protein, wherein the yeast protein stabilizes the expression of the fusion protein in the yeast vehicle or prevents posttranslational modification of the expressed fusion protein. Any suitable endogenous yeast protein can be used in this embodiment, and particularly preferred proteins include, but are not limited to, SUC2 (yeast invertase; which is a good candidate for being able to express a protein both cytosolically and directing it into the secretory pathway from the same promoter, but is dependent on the carbon source in the medium); alpha factor signal leader sequence; SEC7; CPY; phosphoenolpyruvate carboxykinase PCK1, phosphoglycerokinase PGK and triose phosphate isomerase TPI gene products for their repressible expression in glucose and cytosolic localization; Cwp2p for its localization and retention in the cell wall; the heat shock proteins SSA1, SSA3, SSA4, SSC1 and KAR2, whose expression is induced and whose proteins are more thermostable upon exposure of cells to heat treatment; the mitochondrial protein CYC1 for import into mitochondria; BUD genes for localization at the yeast cell bud during the initial phase of daughter cell formation; ACT1 for anchoring onto actin bundles.

In one embodiment, the endogenous yeast protein/peptide or the synthetic peptide used in fusion proteins herein comprise an antibody epitope for identification and purification of the fusion protein. Antibodies may already be available that selectively bind to an endogenous antigen or can be readily generated. Finally, if it is desired to direct a protein to a particular cellular location (e.g., into the secretory pathway, into mitochondria, into the nucleus), then the construct can use the endogenous signals for the yeast protein to be sure that the cellular machinery is optimized for that delivery system. Preferably, an antibody is available or produced that selectively binds to the fusion partner. According to the present invention, the phrase "selectively binds to" refers to the ability of an antibody, antigen binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.).

In one embodiment, a vaccine of the present invention can comprise a peptide linked to the C-terminus of the HCV antigen, wherein the peptide allows for recognition of the fusion protein by an antibody directed against the peptide. In one aspect, the peptide comprises an amino acid sequence of G-G-G-H-H-H-H-H-H (SEQ ID NO:10). This embodiment can be used alone or in conjunction with other aspects of the fusion proteins described above.

As discussed above, the fusion proteins used in the vaccines and compositions of the invention include at least one HCV antigen for vaccinating an animal. The composition or vaccine can include, one, two, a few, several or a plurality of HCV antigens, including one or more immunogenic domains of one or more HCV antigens, as desired. For example, any fusion protein described herein can include at least a portion of any one or more HCV proteins selected from: HCV E1 envelope glycoprotein, HCV E2 envelope glycoprotein, HCV P7 ion channel, HCV NS2 metalloprotease, HCV NS3 protease/helicase, HCV NS4a NS3 protease cofactor, HCV NS4b, HCV NS5a, HCV NS5b RNA-dependent RNA polymerase, and HCV Core sequence. In a preferred embodiment, a portion of an HCV protein other than the HCV Core sequence is linked to at least a portion of an HCV Core sequence. In another aspect, the fusion protein comprises at least one or more immunogenic domains of one or more HCV antigens.

According to the present invention, the general use herein of the term "antigen" refers: to any portion of a protein (peptide, partial protein, full-length protein), wherein the protein is naturally occurring or synthetically derived, to a cellular composition (whole cell, cell lysate or disrupted cells), to an organism (whole organism, lysate or disrupted cells) or to a carbohydrate or other molecule, or a portion thereof, wherein the antigen elicits an antigen-specific immune response (humoral and/or cellular immune response), or alternatively acts as a toleragen, against the same or similar antigens that are encountered within the cells and tissues of the animal to which the antigen is administered.

In one embodiment of the present invention, when it is desirable to stimulate an immune response, the term "antigen" can be used interchangeably with the term "immunogen", and is used herein to describe a protein, peptide, cellular composition, organism or other molecule which elicits a humoral and/or cellular immune response (i.e., is antigenic), such that administration of the immunogen to an animal (e.g., via a vaccine of the present invention) mounts an antigen-specific immune response against the same or similar antigens that are encountered within the tissues of the animal. Therefore, to vaccinate an animal against a particular antigen means, in one embodiment, that an immune response is elicited against the antigen or immunogenic or toleragenic portion thereof, as a result of administration of the antigen. Vaccination preferably results in a protective or therapeutic effect, wherein subsequent exposure to the antigen (or a source of the antigen) elicits an immune response against the antigen (or source) that reduces or prevents a disease or condition in the animal. The concept of vaccination is well known in the art. The immune response that is elicited by administration of a therapeutic composition of the present invention can be any detectable change in any facet of the immune response (e.g., cellular response, humoral response, cytokine production), as compared to in the absence of the administration of the vaccine.

A "vaccinating antigen" can be an immunogen or a toleragen, but is an antigen used in a vaccine, where a biological response (elicitation of an immune response, tolerance) is to be elicited against the vaccinating antigen.

An immunogenic domain (portion, fragment, epitope) of a given antigen can be any portion of the antigen (i.e., a peptide fragment or subunit or an antibody epitope or other conformational epitope) that contains at least one epitope that acts as an immunogen when administered to an animal. For example, a single protein can contain multiple different immunogenic domains. Immunogenic domains need not be linear sequences within a protein, in the case of a humoral response.

An epitope is defined herein as a single immunogenic site within a given antigen that is sufficient to elicit an immune response, or a single toleragenic site within a given antigen that is sufficient to suppress, delete or render inactive an immune response. Those of skill in the art will recognize that T cell epitopes are different in size and composition from B cell epitopes, and that epitopes presented through the Class I MHC pathway differ from epitopes presented through the Class II MHC pathway. Epitopes can be linear sequence or conformational epitopes (conserved binding regions). depending on the type of immune response. An antigen can be as small as a single epitope, or larger, and can include multiple epitopes. As such, the size of an antigen can be as small as about 5-12 amino acids (e.g., a peptide) and as large as: a full length protein, including a multimer and fusion proteins, chimeric proteins, whole cells, whole microorganisms, or portions thereof (e.g., lysates of whole cells or extracts of microorganisms). In addition, antigens can include carbohydrates, which can be loaded into a yeast vehicle or into a composition of the invention. It will be appreciated that in some embodiments (i.e., when the antigen is expressed by the yeast vehicle from a recombinant nucleic acid molecule), the antigen is a protein, fusion protein, chimeric protein, or fragment thereof, rather than an entire cell or microorganism. Preferred HCV fusion proteins of the invention are described herein.

In yet another embodiment of the invention, the HCV antigen portion of the vaccine is produced as a fusion protein comprising two or more antigens. In one aspect, the fusion protein can include two or more immunogenic domains or two or more epitopes of one or more antigens (e.g., the HCV NS3 sequence and the HCV Core sequence described herein). Such a vaccine may provide antigen-specific immunization in a broad range of patients. For example, a multiple domain fusion protein useful in the present invention may have multiple domains, wherein each domain consists of a peptide from a particular protein, the peptide consisting of at least 4 amino acid residues flanking either side of and including a mutated amino acid that is found in the protein, wherein the mutation is associated with a particular disease or condition (e.g., HCV infection).

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. As discussed above, according to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

In one preferred aspect of the invention, the HCV antigen is an HCV protein consisting of HCV NS3 protease and Core sequence. In another aspect, the HCV antigen consists of an HCV NS3 protein lacking the catalytic domain of the natural NS3 protein which is linked to HCV Core sequence. In another aspect, the HCV antigen consists of the 262 amino acids of HCV NS3 following the initial N-terminal 88 amino acids of the natural NS3 protein (i.e., positions 89-350 of HCV NS3; SEQ ID NO:20) linked to HCV Core sequence. In one aspect, the HCV Core sequence lacks the hydrophobic C-terminal sequence. In another aspect, the HCV Core sequence lacks the C-terminal two amino acids, glutamate and aspartate. In a preferred aspect, the HCV Core sequence consists of amino acid positions 2 through 140 of the natural HCV Core sequence.

An example of such a vaccine is described in Example 1. In this embodiment, a yeast (e.g., *Saccharomyces cerevisiae*) was engineered to express a HCV NS3-Core fusion protein under the control of the copper-inducible promoter, CUP1. The fusion protein is a single polypeptide with the following sequence elements fused in frame from N- to C-terminus (HCV polyprotein (SEQ ID NO:20) numbering in parentheses, with the amino acid sequence of the fusion protein being represented herein by SEQ ID NO:2): 1) the sequence MADEAP (SEQ ID NO:9) to impart resistance to proteasomal degradation (positions 1 to 6 of SEQ ID NO:2); 2) amino acids 89 to 350 of (1115 to 1376 of SEQ ID NO:20) of the HCV NS3 protease protein (positions 6 to 268 of SEQ ID NO:2); 3) a single threonine amino acid residue introduced in cloning (position 269 of SEQ ID NO:2); 4) amino acids 2 to 140 (2 to 140 of SEQ ID NO:20) of the HCV Core protein (positions 270 to 408 of SEQ ID NO:2); and 5) the sequence E-D to increase the hydrophilicity of the Core variant (positions 409 to 410 of SEQ ID NO:2). A nucleic acid sequence encoding the fusion protein of SEQ ID NO:2 is represented herein by SEQ ID NO: 1.

In another preferred aspect of the invention, the HCV antigen is an inactivated full-length HCV NS3 that is part of a fusion protein according to the invention. An example of such a vaccine is described in Example 2. In this embodiment, a yeast (e.g., *Saccharomyces cerevisiae*) was engineered to express an inactivated full-length HCV NS3 fusion protein under the control of the copper-inducible promoter, CUP1. The fusion protein comprising the full-length HCV NS3 is a single polypeptide with the following sequence elements fused in frame from N- to C-terminus (HCV polyprotein numbering in parentheses, with the amino acid sequence of the fusion protein being represented herein by SEQ ID NO:4): 1) the sequence MADEAP (SEQ ID NO:9) to impart resistance to proteasomal degradation (positions 1 to 6 of SEQ ID NO:4); and 2) amino acids 1 to 631 (1027 to 1657 of SEQ ID NO:20) of the HCV NS3 protease protein (positions 7 to 637 of SEQ ID NO:4) (note that the amino acid at HCV polypeptide residue 1165 has been changed from a serine to an alanine in order to inactivate the proteolytic activity). A nucleic acid sequence encoding the fusion protein of SEQ ID NO:4 is represented herein by SEQ ID NO:3.

In another preferred aspect of the invention, the yeast vaccine comprises a truncated HCV E1-E2 fusion protein. An example of such a vaccine is described in Example 3. In this embodiment, a yeast (e.g., *Saccharomyces cerevisiae*) is engineered to express an E1-E2 fusion protein as a single polypeptide having the following sequence elements fused in frame from N- to C-terminus (HCV polyprotein numbering in parentheses, where the amino acid sequence of the fusion protein is represented herein by SEQ ID NO:6): 1) The sequence MADEAP (SEQ ID NO:9) to impart resistance to proteasomal degradation (positions 1 to 6 of SEQ ID NO:6); 2) amino acids 1 to 156 (192 to 347 of SEQ ID NO:20) of HCV protein E1 (positions 7 to 162 of SEQ ID NO:6); and 3) amino acids 1 to 334 (384 to 717 of SEQ ID NO:20) of HCV protein E2 (positions 163 to 446 of SEQ ID NO:6). It is noted that in this particular fusion protein, 36 C-terminal hydrophobic amino acids of E1 and 29 C-terminal hydrophobic amino acids of E2 were omitted from the fusion protein to promote cytoplasmic accumulation in yeast. A nucleic acid sequence encoding the fusion protein of SEQ ID NO:6 is represented herein by SEQ ID NO:5.

In yet another preferred aspect of the invention, the yeast vaccine comprises a transmembrane (TM) domain-deleted HCV NS4b fusion protein. An example of such vaccine is described in Example 4. The fusion protein is a single polypeptide with the following sequence elements arranged in tandem, in frame, from N- to C-terminus (polyprotein numbering in parentheses, with the amino acid sequence of the fusion protein being represented herein by SEQ ID NO:8): 1) The sequence MADEAP (SEQ ID NO:9) to impart resistance to proteosomal degradation (positions 1 to 6 of SEQ ID NO:8); 2) amino acids 1 to 69 (1712 to 1780 of SEQ ID NO:20) of HCV protein NS4b (positions 7 to 75 of SEQ ID NO:8); and 3) amino acids 177 to 261 (1888 to 1972 of SEQ ID NO:20) of HCV protein NS4b (positions 76 to 160 of SEQ ID NO:8). A 107 amino acid region corresponding to NS4b amino acids 70 to 176 (1781 to 1887 of SEQ ID NO:20) that contains multiple membrane spanning domains was omitted to promote cytoplasmic accumulation in yeast. A nucleic acid sequence encoding the fusion protein of SEQ ID NO:8 is represented herein by SEQ ID NO:7.

In yet another preferred aspect of the invention, the yeast vaccine comprises a Core-E1-E2 fusion protein. The fusion protein is a single polypeptide with the following sequence elements arranged in tandem, in frame, from N- to C-terminus (polyprotein numbering in parentheses, with the amino acid sequence of the fusion protein being represented herein by SEQ ID NO:12): 1) The sequence MADEAP (SEQ ID NO:9) to impart resistance to proteosomal degradation (positions 1-6 of SEQ ID NO:12); and 2) amino acids 1 to 746 (2 to 746 of SEQ ID NO:20) of unmodified HCV polyprotein encoding full-length Core, E1, and E2 proteins (positions 7 to 751 of SEQ ID NO:12: Core spanning from position 7 to 196; E1 spanning from positions 197 to 387; and E2 spanning from positions 388 to 751). A nucleic acid sequence encoding the fusion protein of SEQ ID NO: 12 is represented herein by SEQ ID NO: 11.

In another preferred aspect of the invention, the yeast vaccine comprises a Core-E1-E2 fusion protein with transmembrane domains deleted. The fusion protein is a single polypeptide with the following sequence elements fused in frame from N- to C-terminus (polyprotein numbering in parentheses, with the amino acid sequence of the fusion protein being represented herein by SEQ ID NO:14): 1) The sequence MADEAP (SEQ ID NO:9) to impart resistance to proteasomal degradation, 2) amino acids 2 to 140 (2 to 140 of SEQ ID NO:20) of HCV Core protein (positions 7 to 145 of SEQ ID NO:14), 3) amino acids 1 to 156 (192 to 347 of SEQ ID NO:20) of HCV protein E1 (positions 146 to 301 of SEQ ID NO:14), and 4) amino acids 1 to 334 (384 to 717 of SEQ ID NO:20) of HCV protein E2 (positions 302 to 635 of SEQ ID NO:14). The 51 C-terminal hydrophobic amino acids of Core protein, the 36 C-terminal hydrophobic amino acids of E1 and the 29 C-terminal hydrophobic amino acids of E2 were omitted from the fusion protein to promote cytoplasmic accumulation in yeast. A nucleic acid sequence encoding the fusion protein of SEQ ID NO:14 is represented herein by SEQ ID NO:13.

In yet another preferred aspect of the invention, the yeast vaccine comprises an NS3-NS4a-NS4b fusion protein wherein the NS3 protease is inactivated and the NS4b lacks a transmembrane domain. The NS3-NS4a-NS4b fusion protein is a single polypeptide with the following sequence elements fused in frame from N- to C-terminus (polyprotein numbering in parentheses, with the amino acid sequence of the fusion protein being represented herein by SEQ ID NO:16): 1) The sequence MADEAP (SEQ ID NO:9) to impart resistance to proteasomal degradation (positions 1 to 6 of SEQ ID NO:16); 2) amino acids 1 to 631 (1027 to 1657 of SEQ ID NO:20) corresponding to full-length HCV NS3 protein (note: Serine 139 (position 1165, with respect to SEQ ID NO:20) is changed to alanine to inactivate the proteolytic potential of NS3) (positions 7 to 634 of SEQ ID NO:16); 3) amino acids 1 to 54 (1658 to 1711 of SEQ ID NO:20) of NS4a protein (positions 635 to 691 of SEQ ID NO:16); 4) amino acids 1 to 69 (1712 to 1780 of SEQ ID NO:20) of HCV protein NS4b (positions 692 to 776 of SEQ ID NO: 16); and 5) amino acids 177 to 261 (1888 to 1972 of SEQ ID NO:20) of HCV protein NS4b (positions 777 to 845 of SEQ ID NO:16). A 107 amino acid region corresponding to NS4b amino acids 70 to 176 (1781 to 1887 of SEQ ID NO:20) that contains multiple membrane spanning domains was omitted to promote cytoplasmic accumulation in yeast. A nucleic acid sequence encoding the fusion protein of SEQ ID NO:16 is represented herein by SEQ ID NO:15.

In another preferred aspect of the invention, the yeast vaccine comprises a NS5a-NS5b fusion protein with an inactivating deletion of NS5b C-terminus. This NS5a-NS5b fusion protein is a single polypeptide with the following sequence elements fused in frame from N- to C-terminus (polyprotein numbering in parentheses, with the amino acid sequence of the fusion protein being represented herein by SEQ ID NO:18): 1) The sequence MADEAP (SEQ ID NO:9) to impart resistance to proteasomal degradation (positions 1 to 6 of SEQ ID NO:18); 2) the entirety of NS5a protein corresponding to amino acids 1 to 448 (1973 to 2420 of SEQ ID NO:20) (positions 7 to 454 of SEQ ID NO:18); and 3) amino acids 1 to 539 (2421 to 2959 of SEQ ID NO:20) of NS5b (positions 455 to 993 of SEQ ID NO:18). The 52 C-terminal residues that are required for the activity of NS5b in HCV replication were deleted to inactivate the protein. A nucleic acid sequence encoding the fusion protein of SEQ ID NO:18 is represented herein by SEQ ID NO:17.

According to the present invention, any of the fusion proteins described herein can comprise a peptide linked to the N-terminus of the fusion protein that consists of at least 2-6 amino acid residues that are heterologous to the HCV antigen. In one aspect, the peptide comprises an amino acid sequence of M-$X_2$-$X_3$-$X_4$-$X_5$-$X_6$, wherein $X_2$ is any amino acid except glycine, proline, lysine or arginine; wherein $X_3$ is any amino acid except methionine, lysine or arginine; wherein $X_4$ is any amino acid except methionine, lysine or arginine; wherein $X_5$ is any amino acid except methionine, lysine or arginine; and wherein $X_6$ is any amino acid except methionine. In one aspect, $X_6$ is a proline. In another aspect, the peptide comprises an amino acid sequence of M-A-D-E-A-P (SEQ ID NO:9).

In a particular aspect of the invention, the above-described fusion protein contains a heterologous linker sequence between two HCV proteins (e.g. the HCV NS3 sequence and the HCV Core sequence). In a preferred embodiment, the heterologous linker sequence consists of a single heterologous amino acid residue. In a more preferred embodiment, the heterologous linker sequence consists of a single threonine residue.

In any of the above-described compositions (e.g., vaccines) of the present invention, the following aspects related to the yeast vehicle are included in the invention. In one embodiment, yeast vehicle is selected from the group consisting of a whole yeast, a yeast spheroplast, a yeast cytoplast, a yeast ghost, and a subcellular yeast membrane extract or fraction thereof. In one aspect, a yeast cell or yeast spheroplast used to prepare the yeast vehicle was transformed with a recombinant nucleic acid molecule encoding the antigen(s) such that the antigen is recombinantly expressed by the yeast cell or yeast spheroplast. In this aspect, the yeast cell or yeast spheroplast that recombinantly expresses the antigen(s) is used to produce a yeast vehicle comprising a yeast cytoplast, a yeast ghost, or a subcellular yeast membrane extract or fraction thereof. In one aspect, the yeast vehicle is from a non-pathogenic yeast. In another aspect, the yeast vehicle is from a yeast selected from the group consisting of: *Saccharomyces, Schizosaccharomyces, Kluveromyces, Hansenula, Candida* and *Pichia*. In one aspect, the *Saccharomyces* is *S. cerevisiae*.

In general, the yeast vehicle and antigen can be associated by any technique described herein. In one aspect, the yeast vehicle was loaded intracellularly with the HCV antigen. In another aspect, the HCV antigen was covalently or non-covalently attached to the yeast vehicle. In yet another aspect, the yeast vehicle and the HCV antigen were associated by mixing. In another aspect, the antigen is expressed recombinantly by the yeast vehicle or by the yeast cell or yeast spheroplast from which the yeast vehicle was derived.

More specifically, according to the present invention, a yeast vehicle is any yeast cell (e.g., a whole or intact cell) or a derivative thereof (see below) that can be used in conjunction with an antigen in a vaccine or therapeutic composition of the invention, or as an adjuvant. The yeast vehicle can therefore include, but is not limited to, a live intact yeast microorganism (i.e., a yeast cell having all its components including a cell wall), a killed (dead) intact yeast microorganism, or derivatives thereof including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), or a subcellular yeast membrane extract or fraction thereof (also referred to previously as a subcellular yeast particle).

Yeast spheroplasts are typically produced by enzymatic digestion of the yeast cell wall. Such a method is described, for example, in Franzusoff et al., 1991, *Meth. Enzymol.* 194, 662-674., incorporated herein by reference in its entirety. Yeast cytoplasts are typically produced by enucleation of yeast cells. Such a method is described, for example, in Coon, 1978, *Natl. Cancer Inst. Monogr.* 48, 45-55 incorporated herein by reference in its entirety. Yeast ghosts are typically produced by resealing a permeabilized or lysed cell and can, but need not, contain at least some of the organelles of that cell. Such a method is described, for example, in Franzusoff et al., 1983, *J. Biol. Chem.* 258, 3608-3614 and Bussey et al., 1979, *Biochim. Biophys. Acta* 553, 185-196, each of which is incorporated herein by reference in its entirety. A subcellular yeast membrane extract or fraction thereof refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., 1991, *Meth. Enzymol.* 194, 662-674. One may also use fractions of yeast membrane extracts that contain yeast membrane portions and, when the antigen was expressed recombinantly by the yeast prior to preparation of the yeast membrane extract, the antigen of interest.

Any yeast strain can be used to produce a yeast vehicle of the present invention. Yeast are unicellular microorganisms that belong to one of three classes: Ascomycetes, Basidiomycetes and Fungi Imperfecti. While pathogenic yeast strains, or nonpathogenic mutants thereof can be used in accordance with the present invention, nonpathogenic yeast strains are preferred. Preferred genera of yeast strains include *Saccharomyces, Candida* (which can be pathogenic), *Cryptococcus, Hansenula, Kluyveromyces, Pichia, Rhodotorula, Schizosaccharomyces* and *Yarrowia*, with *Saccharomyces, Candida, Hansenula, Pichia* and *Schizosaccharomyces* being more preferred, and with *Saccharomyces* being particularly preferred. Preferred species of yeast strains include *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe,* and *Yarrowia lipolytica*. It is to be appreciated that a number of these species include a variety of subspecies, types, subtypes, etc. that are meant to be included within the aforementioned species. More preferred yeast species include *S. cerevisiae, C. albicans, H. polymorpha, P. pastoris* and *S. pombe. S. cerevisiae* is particularly preferred due to it being relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir$^\circ$ strain.

In one embodiment, a preferred yeast vehicle of the present invention is capable of fusing with the cell type to which the yeast vehicle and antigen is being delivered, such as a dendritic cell or macrophage, thereby effecting particularly efficient delivery of the yeast vehicle, and in many embodiments, the antigen(s), to the cell type. As used herein, fusion of a yeast vehicle with a targeted cell type refers to the ability of the yeast cell membrane, or particle thereof, to fuse with the membrane of the targeted cell type (e.g., dendritic cell or macrophage), leading to syncytia formation. As used herein, a syncytium is a multinucleate mass of protoplasm produced by the merging of cells. A number of viral surface proteins (including those of immunodeficiency viruses such as HIV, influenza virus, poliovirus and adenovirus) and other fusogens (such as those involved in fusions between eggs and sperm) have been shown to be able to effect fusion between two membranes (i.e., between viral and mammalian cell membranes or between mammalian cell membranes). For example, a yeast vehicle that produces an HIV gp120/gp41 heterologous antigen on its surface is capable of fusing with a CD4+ T-lymphocyte. It is noted, however, that incorporation of a targeting moiety into the yeast vehicle, while it may be desirable under some circumstances, is not necessary. The present inventors have previously shown that yeast vehicles of the present invention are readily taken up by dendritic cells (as well as other cells, such as macrophages).

Yeast vehicles can be formulated into compositions of the present invention, including preparations to be administered to a patient directly or first loaded into a carrier such as a dendritic cell, using a number of techniques known to those skilled in the art. For example, yeast vehicles can be dried by lyophilization. Formulations comprising yeast vehicles can also be prepared by packing yeast in a cake or a tablet, such as is done for yeast used in baking or brewing operations. In addition, prior to loading into a dendritic cell, or other type of administration with an antigen, yeast vehicles can also be mixed with a pharmaceutically acceptable excipient, such as an isotonic buffer that is tolerated by the host cell. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, glycerol or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

According to the present invention, the term "yeast vehicle-antigen complex" or "yeast-antigen complex" is used generically to describe any association of a yeast vehicle with an antigen. Such association includes expression of the antigen by the yeast (a recombinant yeast), introduction of an antigen into a yeast, physical attachment of the antigen to the yeast, and mixing of the yeast and antigen together, such as in a buffer or other solution or formulation. These types of complexes are described in detail below.

In one embodiment, a yeast cell used to prepare the yeast vehicle is transformed with a heterologous nucleic acid molecule encoding the antigen such that the antigen is expressed by the yeast cell. Such a yeast is also referred to herein as a recombinant yeast or a recombinant yeast vehicle. The yeast cell can then be loaded into the dendritic cell as an intact cell, or the yeast cell can be killed, or it can be derivatized such as by formation of yeast spheroplasts, cytoplasts, ghosts, or subcellular particles, any of which is followed by loading of the derivative into the dendritic cell. Yeast spheroplasts can also be directly transfected with a recombinant nucleic acid molecule (e.g., the spheroplast is produced from a whole yeast, and then transfected) in order to produce a recombinant spheroplast that expresses an antigen.

According to the present invention, an isolated nucleic acid molecule or nucleic acid sequence, is a nucleic acid molecule or sequence that has been removed from its natural milieu. As such, "isolated" does not necessarily reflect the extent to which the nucleic acid molecule has been purified. An isolated nucleic acid molecule useful for transfecting yeast vehicles include DNA, RNA, or derivatives of either DNA or RNA. An isolated nucleic acid molecule can be double stranded or single stranded. An isolated nucleic acid molecule useful in the present invention includes nucleic acid molecules that encode a protein or a fragment thereof, as long as the fragment contains at least one epitope useful in a composition of the present invention.

Nucleic acid molecules transformed into yeast vehicles of the present invention can include nucleic acid sequences encoding one or more proteins, or portions (fragments, domains, conformational epitopes) thereof. Such nucleic acid molecules can comprise partial or entire coding regions, regulatory regions, or combinations thereof. One advantage of yeast strains is their ability to carry a number of nucleic acid molecules and of being capable of producing a number of heterologous proteins. A preferred number of antigens to be produced by a yeast vehicle of the present invention is any number of antigens that can be reasonably produced by a yeast vehicle, and typically ranges from at least one to at least about 5 or more, with from about 2 to about 5 heterologous antigens being more preferred.

A peptide or protein encoded by a nucleic acid molecule within a yeast vehicle can be a full-length protein, or can be a functionally equivalent protein in which amino acids have been deleted (e.g., a truncated version of the protein), inserted, inverted, substituted and/or derivatized (e.g., acetylated, glycosylated, phosphorylated, tethered by a glycerophosphatidyl inositol (GPI) anchor such that the modified protein has a biological function substantially similar to that of the natural protein (or which has enhanced or inhibited function as compared to the natural protein, if desired). Modifications can be accomplished by techniques known in the art including, but not limited to, direct modifications to the protein or modifications to the nucleic acid sequence encoding the protein using, for example, classic or recombinant DNA techniques to effect random or targeted mutagenesis. Functionally equivalent proteins can be selected using assays that measure the biological activity of the protein. Preferred HCV antigens are discussed above.

Expression of an antigen in a yeast vehicle of the present invention is accomplished using techniques known to those skilled in the art. Briefly, a nucleic acid molecule encoding at least one desired antigen is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens can be on one or more expression vectors operatively linked to one or more transcription control sequences.

In a recombinant molecule of the present invention, nucleic acid molecules are operatively linked to expression vectors containing regulatory sequences such as transcription control sequences, translation control sequences, origins of replication, and other regulatory sequences that are compatible with the yeast cell and that control the expression of nucleic acid molecules. In particular, recombinant molecules of the present invention include nucleic acid molecules that are operatively linked to one or more transcription control sequences. The phrase "operatively linked" refers to linking a nucleic acid molecule to a transcription control sequence in a manner such that the molecule is able to be expressed when transfected (i.e., transformed, transduced or transfected) into a host cell.

Transcription control sequences, which can control the amount of protein produced, include sequences which control the initiation, elongation, and termination of transcription. Particularly important transcription control sequences are those which control transcription initiation, such as promoter and upstream activation sequences. Any suitable yeast promoter can be used in the present invention and a variety of such promoters are known to those skilled in the art. Preferred promoters for expression in *Saccharomyces cerevisiae* include, but are not limited to, promoters of genes encoding the following yeast proteins: alcohol dehydrogenase I (ADH1) or II (ADH2), CUP1, phosphoglycerate kinase (PGK), triose phosphate isomerase (TPI), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome $c_1$ (CYC1), Sec7 protein (SEC7) and acid phosphatase (PHO5), with hybrid promoters such as ADH2/GAPDH and CYC1/GAL10 promoters being more preferred, and the ADH2/GAPDH promoter, which is induced when glucose concentrations in the cell are low (e.g., about 0.1 to about 0.2 percent), being even more preferred. Likewise, a number of upstream activation sequences (UASs), also referred to as enhancers, are known. Preferred upstream activation sequences for expression in *Saccharomyces cerevisiae* include, but are not limited to, the UASs of genes encoding the following proteins: PCK1, TPI, TDH3, CYC1, ADH1, ADH2, SUC2, GAL1, GAL7 and GAL10, as well as other UASs activated by the GAL4 gene product, with the ADH2 UAS being particularly preferred. Since the ADH2 UAS is activated by the ADR1 gene product, it is preferable to overexpress the ADR1 gene when a heterologous gene is operatively linked to the ADH2 UAS. Preferred transcription termination sequences for expression in *Saccharomyces cerevisiae* include the termination sequences of the α-factor, GAPDH, and CYC1 genes.

Preferred transcription control sequences to express genes in methyltrophic yeast include the transcription control regions of the genes encoding alcohol oxidase and formate dehydrogenase.

Transfection of a nucleic acid molecule into a yeast cell according to the present invention can be accomplished by any method by which a nucleic acid molecule administered into the cell and includes, but is not limited to, diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. Examples of yeast vehicles carrying such nucleic acid molecules are disclosed in detail herein. As discussed above, yeast cytoplast, yeast ghost, and subcellular yeast membrane extract or fractions thereof can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens.

Effective conditions for the production of recombinant yeast vehicles and expression of the antigen by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, Erlenmeyer flasks, test tubes, microtiter dishes, and petri plates. Culturing is carried out at a temperature, pH and oxygen content appropriate for the yeast strain. Such culturing conditions are well within the expertise of one of ordinary skill in the art (see, for example, Guthrie et al. (eds.), 1991, *Methods in Enzymology*, vol. 194, Academic Press, San Diego).

In one embodiment of the present invention, as an alternative to expression of an antigen recombinantly in the yeast vehicle, a yeast vehicle is loaded intracellularly with the protein or peptide antigen, or with carbohydrates or other molecules that serve as an antigen. Subsequently, the yeast vehicle, which now contains the antigen intracellularly, can be administered to the patient or loaded into a carrier such as a dendritic cell (described below). As used herein, a peptide comprises an amino acid sequence of less than or equal to about 30-50 amino acids, while a protein comprises an amino acid sequence of more than about 30-50 amino acids; proteins can be multimeric. A protein or peptide useful as an antigen can be as small as a T cell epitope (i.e., greater than 5 amino acids in length) and any suitable size greater than that which comprises multiple epitopes, protein fragments, full-length proteins, chimeric proteins or fusion proteins. Peptides and proteins can be derivatized either naturally or synthetically; such modifications can include, but are not limited to, glycosylation, phosphorylation, acetylation, myristylation, prenylation, palmitoylation, amidation and/or addition of glycerophosphatidyl inositol. Peptides and proteins can be inserted directly into yeast vehicles of the present invention by techniques known to those skilled in the art, such as by diffusion, active transport, liposome fusion, electroporation, phagocytosis, freeze-thaw cycles and bath sonication. Yeast vehicles that can be directly loaded with peptides, proteins, carbohydrates, or other molecules include intact yeast, as well as spheroplasts, ghosts or cytoplasts, which can be loaded with antigens after production, but before loading into dendritic cells. Alternatively, intact yeast can be loaded with the antigen, and then spheroplasts, ghosts, cytoplasts, or subcellular particles can be prepared therefrom. Any number of antigens can be loaded into a yeast vehicle in this embodiment, from at least 1, 2, 3, 4 or any whole integer up to hundreds or thousands of antigens, such as would be provided by the loading of a microorganism, by the loading of a mammalian tumor cell, or portions thereof, for example.

In another embodiment of the present invention, an antigen is physically attached to the yeast vehicle. Physical attachment of the antigen to the yeast vehicle can be accomplished by any method suitable in the art, including covalent and non-covalent association methods which include, but are not limited to, chemically crosslinking the antigen to the outer surface of the yeast vehicle or biologically linking the antigen to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

In yet another embodiment, the yeast vehicle and the antigen are associated with each other by a more passive, non-specific or non-covalent binding mechanism, such as by gently mixing the yeast vehicle and the antigen together in a buffer or other suitable formulation. In one embodiment of the invention, the yeast vehicle and the antigen are both loaded intracellularly into a carrier such as a dendritic cell or macrophage to form the therapeutic composition or vaccine of the present invention. Alternatively, an antigen of the invention (i.e., a novel HCV fusion protein of the invention) can be loaded into a dendritic cell in the absence of the yeast vehicle. Various forms in which the loading of both components can be accomplished are discussed in detail below. As used herein, the term "loaded" and derivatives thereof refer to the insertion, introduction, or entry of a component (e.g., the yeast vehicle and/or antigen) into a cell (e.g., a dendritic cell). To load a component intracellularly refers to the insertion or introduction of the component to an intracellular compartment of the cell (e.g., through the plasma membrane and at a minimum, into the cytoplasm, a phagosome, a lysosome, or some intracellular space of the cell). To load a component into a cell references any technique by which the component is either forced to enter the cell (e.g., by electroporation) or is placed in an environment (e.g., in contact with or near to a cell) where the component will be substantially likely to enter the cell by some process (e.g., phagocytosis). Loading techniques include, but are not limited to: diffusion, active transport, liposome fusion, electroporation, phagocytosis, and bath sonication. In a preferred embodiment, passive mechanisms for loading a dendritic cell with the yeast vehicle and/or antigen are used, such passive mechanisms including phagocytosis of the yeast vehicle and/or antigen by the dendritic cell.

It is noted that any of the above-described HCV fusion proteins can be provided in a vaccine without one or more of the N-terminal and/or C-terminal modifications that are particularly advantageous for expression of such proteins in yeast. Such HCV fusion proteins are useful in other non-yeast based vaccines, such as by combining the fusion proteins with a conventional adjuvant, pulsing dendritic cells with such fusion proteins, providing DNA or nucleic acid or viral vector vaccines including nucleic acid molecules encoding such fusion proteins, or constructing pseudovirions compose of particular HCV fusion proteins of the invention (e.g., E1-E2 fusions of the invention).

Accordingly, yet another embodiment of the present invention relates to a composition to protect an animal against HCV infection or a symptom resulting from such infection, the composition (which can be a vaccine) comprising: (a) any one or more of the HCV fusion proteins as described above (with or without the various N- and C-terminal modifications described herein); and (b) a pharmaceutically acceptable delivery vehicle (which can include a pharmaceutically acceptable excipient or adjuvant).

Yet another embodiment of the present invention relates to a nucleic acid-based vaccine, such as a DNA vaccine or viral vector vaccine, comprising a nucleic acid construct (e.g., a viral vector or other recombinant nucleic acid molecule) encoding an HCV fusion protein as described herein (with or without the various N- and C-terminal modifications described herein). The vaccine can further include any pharmaceutically acceptable delivery vehicle (which can include a pharmaceutically acceptable excipient or adjuvant).

Another embodiment of the present invention relates to a pseudovirion which is composed of various HCV fusion proteins of the invention, and particularly, an E1-E2 fusion as described herein. Again, the N- or C-terminal modifications that are particularly useful in connection with a yeast-based vaccine of the invention may be included or not included.

In one embodiment of the present invention, a composition or vaccine can also include biological response modifier compounds, or the ability to produce such modifiers (i.e., by transfection with nucleic acid molecules encoding such modifiers), although such modifiers are not necessary to achieve a robust immune response according to the invention. For example, a yeast vehicle can be transfected with or loaded with at least one antigen and at least one biological response modifier compound, or a vaccine or composition of the invention can be administered in conjunction with at least one biological response modifier. Biological response modifiers include compounds that can modulate immune responses, which may be referred to as immunomodulatory compounds. Certain biological response modifiers can stimulate a protective immune response whereas others can suppress a harmful immune response. Certain biological response modifiers preferentially enhance a cell-mediated immune response whereas others preferentially enhance a humoral immune response (i.e., can stimulate an immune response in which there is an increased level of cellular compared to humoral immunity, or vice versa.). There are a number of techniques known to those skilled in the art to measure stimulation or suppression of immune responses, as well as to differentiate cellular immune responses from humoral immune responses.

Suitable biological response modifiers include cytokines, hormones, lipidic derivatives, small molecule drugs and other growth modulators, such as, but not limited to, interleukin 2 (IL-2), interleukin 4 (IL-4), interleukin 10 (IL-10), interleukin 12 (IL-12), interferon gamma (IFN-gamma) insulin-like growth factor I (IGF-1), transforming growth factor beta (TGF-β) steroids, prostaglandins and leukotrienes. The ability of a yeast vehicle to express (i.e., produce), and possibly secrete, IL-2, IL-12 and/or IFN-gamma preferentially enhances cell-mediated immunity, whereas the ability of a yeast vehicle to express, and possibly secrete, IL-4, IL-5 and/or IL-10 preferentially enhances humoral immunity. Other suitable biological response modifiers include, but are not limited to, anti-CTLA-4 antibody (e.g., to release anergic T cells); T cell co-stimulators (e.g., anti-CD137, anti-CD28, anti-CD40); alemtuzumab (e.g., CamPath®), denileukin diftitox (e.g., ONTAK®), anti-CD4, anti-CD25, anti-PD-1, anti-PD-L1, anti-PD-L2 or agents that block FOXP3 (e.g., to abrogate the activity/kill CD4+/CD25+ T regulatory cells); Flt3 ligand, imiquimod (Aldara™), GM-CSF, sargramostim (Leukine®), Toll-like receptor (TLR)-7 agonists, or TLR-9 agonists (e.g., agents that increase the number of, or increase the activation state, of dendritic cells, macrophages and other professional antigen-presenting cells). Such biological response modifiers are well known in the art and are publicly available.

Compositions and therapeutic vaccines of the invention can further include any other compounds that are useful for protecting a subject from HCV infection or that treats or ameliorates any symptom of such an infection.

As mentioned above, the present invention also includes the use of any of the HCV fusion proteins described herein, or a nucleic acid molecule encoding such HCV fusion proteins, in a composition or vaccine in the absence of the yeast vehicle of the present invention, such as in any conventional or non-yeast-based composition or vaccine. Such a composition can include, in addition to the HCV fusion protein, a pharmaceutically acceptable carrier, such as an adjuvant. In addition, yeast-based vaccines of the invention may be provided in conjunction with a pharmaceutically acceptable carrier.

As used herein, a pharmaceutically acceptable carrier refers to any substance or vehicle suitable for delivering an HCV fusion protein useful in a method of the present invention to a suitable in vivo or ex vivo site. Such a carrier can include, but is not limited to, an adjuvant, an excipient, or any other type of delivery vehicle or carrier.

According to the present invention, adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax adjuvant (CytRx™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark).

Carriers are typically compounds that increase the half-life of a therapeutic composition in the treated animal. Suitable carriers include, but are not limited to, polymeric controlled release formulations, biodegradable implants, liposomes, oils, esters, and glycols.

Therapeutic compositions of the present invention can also contain one or more pharmaceutically acceptable excipients. As used herein, a pharmaceutically acceptable excipient refers to any substance suitable for delivering a therapeutic composition useful in the method of the present invention to a suitable in vivo or ex vivo site. Preferred pharmaceutically acceptable excipients are capable of maintaining a composition (or a yeast vehicle or dendritic cell comprising the yeast vehicle) in a form that, upon arrival of the composition at a target cell, tissue, or site in the body, the composition is capable of eliciting an immune response at the target site (noting that the target site can be systemic). Suitable excipients of the present invention include excipients or formularies that transport, but do not specifically target the vaccine to a site (also referred to herein as non-targeting carriers). Examples of pharmaceutically acceptable excipients include, but are not limited to water, saline, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol.

Methods of the Invention

Another embodiment of the present invention relates to a method to protect an animal against an HCV infection or disease resulting therefrom. The method includes the step of administering to an animal that has or is at risk of developing a HCV infection, a vaccine or composition of the present invention as described herein, to reduce or prevent the HCV infection or at least one symptom resulting from the HCV infection in the animal.

Yet another embodiment of the present invention relates to a method to elicit an antigen-specific humoral immune response and/or an antigen-specific cell-mediated immune response in an animal. The method includes administering to the animal a vaccine or composition of the present invention as described herein. The method of the present invention preferentially elicits an antigen-specific cell-mediated immune response in an animal.

In the above-embodiments, the vaccine or composition can include (1) a composition comprising (a) a yeast vehicle; and (b) any one or more of the above-described HCV fusion proteins; and/or (2) (a) any one or more of the above-described HCV fusion proteins; and (b) a pharmaceutically acceptable delivery vehicle (which can include or consist of a pharmaceutically acceptable excipient or adjuvant); and/or (3) (a) an isolated nucleic acid molecule (e.g., a DNA construct, a vector, a viral vector) encoding any one or more of the above-described HCV fusion proteins; and/or (4) isolated dendritic cells (e.g., autologous dendritic cells containing (pulsed with) (a) a yeast vehicle; and/or (b) any one or more of the above-described HCV fusion proteins; and/or (5) HCV pseudovirions composed of any of the E1-E2 containing HCV fusion proteins of described herein.

In one embodiment of the present invention, the vaccine or composition of the invention as described herein can be administered in a protocol that includes the administration of one or more other vaccine or immunotherapy compositions, including any conventional vaccine or composition. For example, such other vaccines or immunotherapy compositions can include any other antigen-containing, antigen-encoding, or antigen-expressing composition, such as a DNA vaccine encoding an HCV antigen or other viral vectors comprising an HCV antigen. Viral vectors for vaccines are known in the art and include, but are not limited to, pox viruses (vaccinia, canary, avipox), adeno viruses, adeno-associated viruses, alpha viruses (Sindbis, VEE). Other types of vaccines, including protein-based vaccines, are also encompassed by this embodiment. In one aspect, such a conventional vaccine or vaccine that is not a part of the present invention or a vaccine of the present invention that does not include a yeast vehicle (e.g., a vaccine comprising a novel HCV fusion protein of the invention in combination with a pharmaceutically acceptable carrier, or a DNA vaccine encoding a novel HCV fusion protein of the invention) can be administered initially to a subject to prime the immune response of the subject against the HCV antigen(s). Subsequently, the vaccine or composition of the present invention, and particularly, a yeast-based vaccine of the present invention, can be administered to the subject in order to boost the immune response. Alternatively, the vaccine or composition of the present invention can be administered to the subject to prime the immune response, including particularly a yeast-based vaccine of the present invention, and the conventional or other vaccine or composition (e.g., a non-yeast-based vaccine comprising a novel HCV fusion protein of the invention or DNA vaccine encoding a novel HCV fusion protein of the invention) can be used to boost the response.

The method of use of the therapeutic composition or vaccine of the present invention preferably elicits an immune response in an animal such that the animal is protected from HCV infection or from disease conditions or symptoms resulting from HCV infection. As used herein, the phrase "protected from a disease" refers to reducing the symptoms of the disease; reducing the occurrence of the disease, and/or reducing the severity of the disease. Protecting an animal can refer to the ability of a therapeutic composition of the present invention, when administered to an animal, to prevent a disease from occurring and/or to cure or to alleviate disease symptoms, signs or causes. As such, to protect an animal from a disease includes both preventing disease occurrence (prophylactic treatment or prophylactic vaccine) and treating an animal that has a disease or that is experiencing initial symptoms of a disease (therapeutic treatment or a therapeutic vaccine). In particular, protecting an animal from a disease is accomplished by eliciting an immune response in the animal by inducing a beneficial or protective immune response which may, in some instances, additionally suppress (e.g., reduce, inhibit or block) an overactive or harmful immune response. The term, "disease" refers to any deviation from the normal health of an animal and includes a state when disease symptoms are present, as well as conditions in which a deviation (e.g., infection, gene mutation, genetic defect, etc.) has occurred, but symptoms are not yet manifested.

In one embodiment, any of the vaccines of the present invention is administered to an individual, or to a population of individuals, who have been infected with HCV. In another embodiment, any of the vaccines of the present invention is administered to an individual, or to a population of individuals, who are at risk of being infected with HCV. Such individuals can include populations identified as higher-risk for HCV infection than, for example, the normal or entire population of individuals. Such populations can be defined by any suitable parameter. In another embodiment, any of the vaccines of the present invention is administered to any individual, or to any population of individuals, regardless of their known or predicted infection status or susceptibility to becoming infected with HCV.

More specifically, a vaccine as described herein, when administered to an animal by the method of the present invention, preferably produces a result which can include alleviation of the disease (e.g., reduction of at least one symptom or clinical manifestation of the disease), elimination of the disease, prevention or alleviation of a secondary disease resulting from the occurrence of a primary disease, prevention of the disease, and stimulation of effector cell immunity against the disease.

The present invention includes the delivery of a composition or vaccine of the invention to an animal. The administration process can be performed ex vivo or in vivo. Ex vivo administration refers to performing part of the regulatory step outside of the patient, such as administering a composition of the present invention to a population of cells (dendritic cells) removed from a patient under conditions such that a yeast vehicle and antigen are loaded into the cell, and returning the cells to the patient. The therapeutic composition of the present invention can be returned to a patient, or administered to a patient, by any suitable mode of administration.

Administration of a vaccine or composition, including a dendritic cell loaded with the yeast vehicle and antigen, a yeast vehicle alone, or a composition comprising a novel HCV fusion protein, alone or in combination with a carrier according to the present invention, can be systemic, mucosal and/or proximal to the location of the target site (e.g., near a tumor). The preferred routes of administration will be apparent to those of skill in the art, depending on the type of condition to be prevented or treated, the antigen used, and/or the target cell population or tissue. Preferred methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, aural, intranasal, oral, pulmonary administration, impregnation of a catheter, and direct injection into a tissue. Particularly preferred routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189:11277-11281, 1992, which is incorporated herein by reference in its entirety). For example, in one embodiment, a composition or vaccine of the invention can be formulated into a composition suitable for nebulized delivery using a suitable inhalation device or nebulizer. Oral delivery can include solids and liquids that can be taken through the mouth, and is useful in the development of mucosal immunity and since compositions comprising yeast vehicles can be easily prepared for oral delivery, for example, as tablets or capsules, as well as being formulated into food and beverage products. Other routes of administration that modulate mucosal immunity are useful in the treatment of viral infections. Such routes include bronchial, intradermal, intramuscular, intranasal, other inhalatory, rectal, subcutaneous, topical, transdermal, vaginal and urethral routes.

In one embodiment of any of the above-identified methods, the vaccine is administered to the respiratory tract. In another embodiment, the vaccine is administered by a parenteral route of administration. In yet another embodiment, the vaccine further comprises dendritic cells or macrophages, wherein a yeast vehicle expressing the fusion protein is delivered to dendritic cells or macrophages ex vivo and wherein the dendritic cell or macrophage containing the yeast vehicle expressing the HCV antigen is administered to the animal. In one aspect of this embodiment, the dendritic cell or the yeast vehicle has been additionally loaded with free antigen. In one aspect, the vaccine is administered as a therapeutic vaccine. In another aspect, the vaccine is administered as a prophylactic vaccine.

According to the present invention, an effective administration protocol (i.e., administering a vaccine or therapeutic composition in an effective manner) comprises suitable dose parameters and modes of administration that result in elicitation of an immune response in an animal that has a disease or condition, or that is at risk of contracting a disease or condition, preferably so that the animal is protected from the disease. Effective dose parameters can be determined using methods standard in the art for a particular disease. Such methods include, for example, determination of survival rates, side effects (i.e., toxicity) and progression or regression of disease.

In accordance with the present invention, a suitable single dose size is a dose that is capable of eliciting an antigen-specific immune response in an animal when administered one or more times over a suitable time period. Doses can vary depending upon the disease or condition being treated. For example, in one embodiment, a single dose of a yeast vehicle of the present invention is from about $1 \times 10^5$ to about $5 \times 10^7$ yeast cell equivalents per kilogram body weight of the organism being administered the composition. In a preferred embodiment, the yeast cells per dose are not adjusted for weight of the organism. In this embodiment, a single dose of a yeast vehicle of the present invention is from about $1 \times 10^4$ to about $1 \times 10^9$ yeast cells per dose. More preferably, a single dose of a yeast vehicle of the present invention is from about 0.1 Y.U. ($1 \times 10^6$ cells) to about 100 Y.U. ($1 \times 10^9$ cells) per dose (i.e., per organism), including any interim dose, in increments of $0.1 \times 10^6$ cells (i.e., $1.1 \times 10^6$, $1.2 \times 10^6$, $1.3 \times 10^6$. . . ). This range of doses can be effectively used in any organism of any size, including mice, monkeys, humans, etc.

When the vaccine is administered by loading the yeast vehicle and antigen into dendritic cells, a preferred single dose of a vaccine of the present invention is from about $0.5 \times 10^6$ to about $40 \times 10^6$ dendritic cells per individual per administration. Preferably, a single dose is from about $1 \times 10^6$ to about $20 \times 10^6$ dendritic cells per individual, and more preferably from about $1 \times 10^6$ to about $10 \times 10^6$ dendritic cells per individual.

When the vaccine comprises a fusion protein of the present invention and a carrier, a preferred single dose is from about 0.01 microgram×kilogram$^{-1}$ and about 10 milligram×kilogram$^{-1}$ body weight of an animal. A more preferred single dose of an agent comprises between about 1 microgram×kilogram$^{-1}$ and about 10 milligram×kilogram$^{-1}$ body weight of an animal. An even more preferred single dose of an agent comprises between about 5 microgram×kilogram$^{-1}$ and about 7 milligram×kilogram$^{-1}$ body weight of an animal. An even more preferred single dose of an agent comprises between about 10 microgram×kilogram$^{-1}$ and about 5 milligram×kilogram$^{-1}$ body weight of an animal. A particularly preferred single dose of an agent comprises between about 0.1 milligram×kilogram$^{-1}$ and about 5 milligram×kilogram$^{-1}$ body weight of an animal, if the an agent is delivered by aerosol. Another particularly preferred single dose of an agent comprises between about 0.1 microgram×kilogram$^{-1}$ and about 10 microgram×kilogram$^{-1}$ body weight of an animal, if the agent is delivered parenterally.

"Boosters" or "boosts" of a therapeutic composition are preferably administered when the immune response against the antigen has waned or as needed to provide an immune response or induce a memory response against a particular antigen or antigen(s). Boosters can be administered from about 2 weeks to several years after the original administration. In one embodiment, an administration schedule is one in which from about $1\times10^5$ to about $5\times10^7$ yeast cell equivalents of a composition per kg body weight of the organism is administered from about one to about 4 times over a time period of from about 1 month to about 6 months.

In the method of the present invention, vaccines and therapeutic compositions can be administered to animal, including any vertebrate, and particularly to any member of the Vertebrate class, Mammalia, including, without limitation, primates, rodents, livestock and domestic pets. Livestock include mammals to be consumed or that produce useful products (e.g., sheep for wool production). Preferred mammals to protect include humans, dogs, cats, mice, rats, goats, sheep, cattle, horses and pigs, with humans being particularly preferred. According to the present invention, the term "patient" or "subject" can be used to describe any animal that is the subject of a diagnostic, prophylactic, or therapeutic treatment as described herein.

Isolated Fusion Proteins, Nucleic Acid Molecules, and Cells

Another embodiment of the present invention includes an isolated protein, comprising any of the isolated fusion protein comprising an HCV antigen(s) as described herein. Also included in the present invention are isolated nucleic acid molecules encoding any of such proteins, recombinant nucleic acid molecules comprising nucleic acid sequences encoding such proteins, and cells and vectors, including viral vectors, that contain or are transfected/transformed with such nucleic acid molecules or recombinant nucleic acid molecules.

As used herein, reference to an isolated protein or polypeptide in the present invention includes full-length proteins, fusion proteins, or any fragment, domain, conformational epitope, or homologue of such proteins. More specifically, an isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. According to the present invention, the terms "modification" and "mutation" can be used interchangeably, particularly with regard to the modifications/mutations to the amino acid sequence of proteins or portions thereof (or nucleic acid sequences) described herein.

As used herein, the term "homologue" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have either enhanced, decreased, or substantially similar properties as compared to the naturally occurring protein or peptide. A homologue can include an agonist of a protein or an antagonist of a protein. Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

The minimum size of a protein and/or a homologue or fragment or other portion thereof of the present invention is, in one aspect, a size sufficient to have the requisite biological activity, such as serving as an antigen(s) or immunogen(s) in a fusion protein or other composition of the invention, or as a target in an in vitro assay. In one embodiment, a protein of the present invention is at least about 8 amino acids in length, or at least about 25 amino acids in length, or at least about 30 amino acids in length, or at least about 40 amino acids in length, or at least about 50 amino acids in length, or at least about 75 amino acids in length, or at least about 100 amino acids in length, or at least about 125 amino acids in length, or at least about 150 amino acids in length, or at least about 175 amino acids in length, or at least about 200 amino acids in length, or at least about 250 amino acids in length, or at least about 300 amino acids in length, or at least about 350 amino acids in length, or at least about 400 amino acids in length, or at least about 450 amino acids in length, or at least about 500 amino acids in length, or at least about 550 amino acids in length, or at least about 600 amino acids in length, and so on, in any length between 8 amino acids and up to the full length of a protein of the invention, the full-length of a combination of proteins or portions thereof, or longer, in whole integers (e.g., 8, 9, 10, . . . 25, 26, . . . 102, 103, . . .). There is no limit, other than a practical limit, on the maximum size of such a protein in that the protein can include a portion of a protein, a functional domain, or a biologically active or useful fragment thereof, or a full-length protein, plus additional sequence (e.g., a fusion protein sequence), if desired.

Preferred fusion proteins according to the present invention include any of the fusion proteins described herein. Exemplary fusion proteins encompassed by the present invention include those fusion proteins comprising, consisting essentially of, or consisting of, and amino acid sequence selected from SEQ ID NO:2, SEQ ID NO:4, SEQ ID NO:6, SEQ ID NO:8, SEQ ID NO:12, SEQ ID NO:14, SEQ ID NO:16 AND SEQ ID NO:18. Other fusion protein sequences will be apparent to those of skill in the art given the guidance provided herein, since various HCV protein sequences are well-known in the art.

The present invention also includes any nucleic acid molecules comprising, consisting essentially of, or consisting of, a nucleic acid sequence encoding any of the fusion proteins described herein. In accordance with the present invention, an isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

Preferably, an isolated nucleic acid molecule of the present invention is produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect. Protein homologues (e.g., proteins encoded by nucleic acid homologues) have been discussed in detail above.

A nucleic acid molecule homologue can be produced using a number of methods known to those skilled in the art (see, for example, Sambrook et al., *Molecular Cloning: A Laboratory Manual*, Cold Spring Harbor Labs Press (1989)). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid and/or by hybridization with a wild-type gene.

A recombinant nucleic acid molecule expressing a fusion protein of the present invention is a molecule that can include at least one of any nucleic acid sequence encoding any one or more fusion proteins described herein operatively linked to at least one of any transcription control sequence capable of effectively regulating expression of the nucleic acid molecule (s) in the cell to be transfected. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

A recombinant nucleic acid molecule includes a recombinant vector, which is any nucleic acid sequence, typically a heterologous sequence, which is operatively linked to the isolated nucleic acid molecule encoding a fusion protein of the present invention, which is capable of enabling recombinant production of the fusion protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a virus or a plasmid. Recombinant vectors can be used in the cloning, sequencing, and/or otherwise manipulating of nucleic acid molecules, and can be used in delivery of such molecules (e.g., as in a DNA vaccine or a viral vector-based vaccine). Recombinant vectors are preferably used in the expression of nucleic acid molecules, and can also be referred to as expression vectors. Preferred recombinant vectors are capable of being expressed in a transfected host cell.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. In particular, recombinant molecules of the present invention include nucleic acid molecules that are operatively linked to one or more transcription control sequences. The phrase "operatively linked" refers to linking a nucleic acid molecule to a transcription control sequence in a manner such that the molecule is expressed when transfected (i.e., transformed, transduced or transfected) into a host cell.

Transcription control sequences are sequences that control the initiation, elongation, and termination of transcription. Particularly important transcription control sequences are those that control transcription initiation, such as promoter, enhancer, operator and repressor sequences. Suitable transcription control sequences include any transcription control sequence that can function in a host cell according to the present invention. A variety of suitable transcription control sequences are known to those skilled in the art.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast, or into plant cells. In microbial systems and plant systems, the term "transformation" is used to describe an inherited change due to the acquisition of exogenous nucleic acids by the microorganism or plant and is essentially synonymous with the term "transfection." Therefore, transfection techniques include, but are not limited to, transformation, chemical treatment of cells, particle bombardment, electroporation, microinjection, lipofection, adsorption, infection and protoplast fusion.

One type of recombinant vector useful in a recombinant nucleic acid molecule of the present invention is a recombinant viral vector. Such a vector includes a recombinant nucleic acid sequence encoding a fusion protein of the present invention that is packaged in a viral coat that can be expressed in a host cell in an animal or ex vivo after administration. A number of recombinant viral vectors can be used, including, but not limited to, those based on alphaviruses, poxviruses, adenoviruses, herpesviruses, lentiviruses, adeno-associated viruses and retroviruses. Particularly preferred viral vectors are those based on adenoviruses and adeno-associated viruses. Viral vectors suitable for gene delivery are well known in the art and can be selected by the skilled artisan for use in the present invention. A detailed discussion of current viral vectors is provided in "Molecular Biotechnology," Second Edition, by Glick and Pasternak, ASM Press, Washington D.C., 1998, pp. 555-590, the entirety of which is incorporated herein by reference.

Suitable host cells to transfect with a recombinant nucleic acid molecule according to the present invention include any cell that can be transfected or transformed, including any animal, insect, bacterial, fungal (including yeast) cell. In one embodiment, the host cell is an animal cell, including a tumor cell, that has been transfected with and expresses a fusion protein of the present invention. Such a cell is exemplified in the Examples section and is useful, for example, for assessing antigen-specific T cell responses that are induced by a vaccine or composition of the present invention. Other vaccines or compositions directed against an HCV antigen can also be tested such transfected tumor cells.

The following experimental results are provided for purposes of illustration and are not intended to limit the scope of the invention.

EXAMPLES

Example 1

The following example describes the engineering of GI-5005, a truncated NS3-Core fusion protein yeast vaccine of the present invention.

The GI-5005 *Saccharomyces cerevisiae* was engineered to express a HCV NS3-Core fusion protein under the control of the copper-inducible promoter, CUP1. Two regions of the HCV genome (genotype 1a, H77 strain, cDNA was provided by the NIH) were amplified by PCR in order to generate the product. The NS3-Core fusion protein is a single polypeptide with the following sequence elements fused in frame from N- to C-terminus (HCV polyprotein numbering in parentheses) (represented herein by SEQ ID NO:2): 1) the sequence MADEAP to impart resistance to proteasomal degradation; 2) amino acids 89 to 350 (1115 to 1376) of the HCV NS3 protease protein; 3) a single threonine amino acid residue introduced in cloning; 4) amino acids 2 to 140 (2 to 140) of the HCV Core protein; and 5) the sequence ED to increase the hydrophilicity of the Core variant.

Figure 1B:
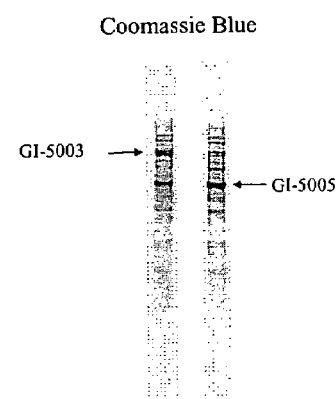

Expression of the HCV NS3-Core fusion protein was confirmed by Western blot analysis of lysates from copper-induced, heat-inactivated GI-5005 yeast. Monoclonal antibodies specific for HCV NS3 (Virostat) or HCV Core protein (Anogen) were used for protein detection (See FIG. 1A and FIG. 1B).

Example 2

The following example describes the engineering of GI-5003, an inactivated HCV NS3 yeast vaccine of the present invention.

The GI-5003 *Saccharomyces cerevisiae* was engineered to express an inactivated full-length HCV NS3 protein under the control of the copper-inducible promoter, CUP1. A single region of the HCV genome (genotype 1a, H77 strain, cDNA was provided by the NIH) was amplified by PCR in order to generate the product. The inactivated NS3 protein is a single polypeptide with the following sequence elements fused in frame from N- to C-terminus (HCV polyprotein numbering in parentheses) (represented herein by SEQ ID NO:4): 1) the sequence MADEAP to impart resistance to proteasomal degradation; and 2) amino acids 1 to 631 (1027 to 1657) of the HCV NS3 protease protein (note that the amino acid at HCV polypeptide residue 1165 has been changed from a serine to an alanine in order to inactivate the proteolytic activity).

Expression of the HCV NS3 protein was confirmed by Western blot analysis of lysates from copper-induced, heat-inactivated GI-5003 yeast. Monoclonal antibodies specific for HCV NS3 (Virostat) were used for protein detection (See FIG. 1A and FIG. 1B).

Example 3

The following example describes the engineering of the GI-5000 series truncated HCV E1-E2 fusion protein yeast vaccine of the present invention.

The E1-E2 fusion protein is a single polypeptide with the following sequence elements fused in frame from N- to C-terminus (HCV polyprotein numbering in parentheses) (represented herein by SEQ ID NO:6): 1) The sequence MADEAP to impart resistance to proteasomal degradation, 2) amino acids 1 to 156 (192 to 347) of HCV protein E1, 3) amino acids 1 to 334 (384-717) of HCV protein E2. 36 C-terminal hydrophobic amino acids of E1 and 29 C-terminal hydrophobic amino acids of E2 were omitted from the fusion protein to promote cytoplasmic accumulation in yeast.

Figure 1C:
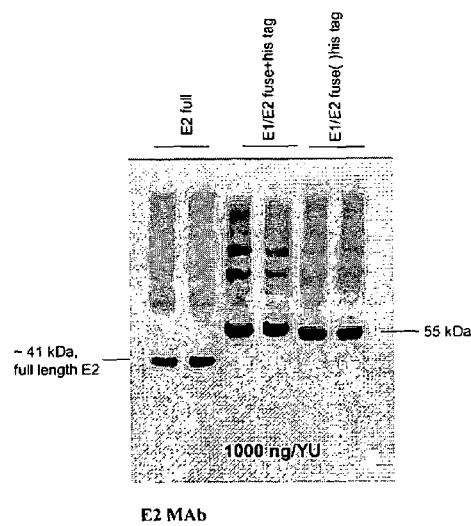
FIG. 1C is a digital image of a Western blot showing expression of a truncated HCV E1-E2 fusion protein in a yeast vehicle according to the present invention.

Expression of the HCV E1/E2 fusion protein was confirmed by Western blot analysis of lysates from copper-induced, heat-inactivated yeast (See FIG. 1C).

Example 4

The following example describes the engineering of the GI-5000 series TM domain-deleted HCV NS4b fusion protein yeast vehicle of the present invention. The NS4b protein is a single polypeptide with the following sequence elements arranged in tandem, in frame, from N- to C-terminus (polyprotein numbering in parentheses) (represented herein by SEQ ID NO:8): 1) The sequence MADEAP to impart resistance to proteosomal degradation, 2) amino acids 1 to 69 (1712 to 1780) of HCV protein NS4b, 3) amino acids 177 to 261 (1888 to 1972) of HCV protein NS4b. A 107 amino acid region corresponding to NS4b amino acids 70 to 176 (1781 to 1887) that contains multiple membrane spanning domains was omitted to promote cytoplasmic accumulation in yeast.

Figure 1D:
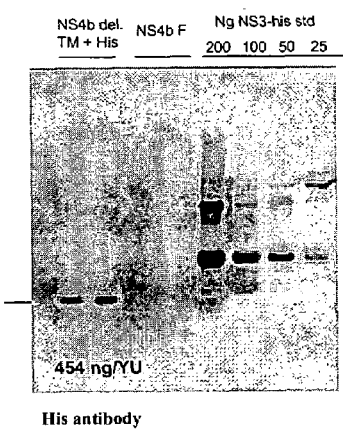
FIG. 1D is a digital image of a Western blot showing expression of a transmembrane (TM) domain-deleted HCV NS4b fusion protein in a yeast vehicle according to the present invention.

Expression of the HCV NS4b fusion protein was confirmed by Western blot analysis of lysates from copper-induced, heat-inactivated yeast (See FIG. 1D).

Example 5

The following example describes non-clinical pharmacology studies in mice using the GI-5005 yeast vehicles (also referred to herein as Tarmogen™™) expressing HCV antigens: immunogenicity studies.

GI-5005 consists of *S. cerevisiae* yeast (W303 strain obtained from the ATCC) that have been stably transduced with a yeast expression plasmid encoding a fusion protein of truncated HCV genotype 1a-derived NS3 and core gene products under the control of the yeast copper-inducible (CUP1) promoter (SEQ ID NO:2), as described in Example 1. In the following studies, C57BL/6 (H-$2^b$) and BALB/cBy (H-$2^d$) mice were injected subcutaneously with GI-5005 yeast. In vitro and in vivo assays that detect induction of antigen-specific lymphocytes by GI-5005 were employed, including lymphocyte proliferation, cell-mediated cytotoxicity, cytokine secretion, and protection from tumor challenge. To support these studies, the following yeast strains, cell lines and recombinant viruses have been generated and maintained:

GI-5003: HCV-NS3 protein-expressing yeast strain. GI-5003 expresses full-length NS3 in which the catalytic domain has been inactivated by a single point mutation.

GI-5005-L: GI-5005 yeast strain expressing less than 50 ng HCV-NS3-Core fusion protein per YU.

GI-5005-M: GI-5005 yeast strain expressing approximately 500 ng HCV-NS3-Core fusion protein per YU GI-5005-H: GI-5005 yeast strain expressing approximately 1400 ng HCV-NS3-Core fusion protein per YU EL4-NS3: C57BL/6-derived EL4 lymphoma cells ($H-2^b$) stably transfected with DNA encoding HCV NS3.

A20-NS3: BALB/c-derived A20 lymphoma cells ($H-2^d$) stably transfected with DNA encoding HCV NS3.

P815-NS3: DBA/2-derived P815 leukemia cells ($H-2^d$) stably transfected with DNA encoding HCV NS3.

Recombinant vaccinia viruses (rVV) encoding beta-galactosidase (rVV-lac), HIV-1 Gag (rVV-Gag), HCV NS3 (rVV-NS3) and HCV Core (rVV-Core) proteins.

In the studies that are described below, and unless otherwise indicated in a particular experiment, female BALB/c and/or C57BL/6 mice (5 per group; aged 6-10 weeks) were injected subcutaneously on a weekly basis with 5 YU (50 million) GI-5005 or GI-5003 and were sacrificed seven days after the final injection. Spleen cell suspensions, pooled from each group, were prepared in RPMI-1640 tissue culture medium supplemented with 10% heat-inactivated fetal calf serum, L-glutamine, HEPES and 2-mercaptoethanol and were subjected to in vitro stimulation (IVS) conditions utilizing both HCV antigen-specific (typically rVV-NS3 and/or rVV-Core) and yeast antigen-specific (typically GI-5005) stimuli as specified. Standard assays were employed to evaluate immune responses induced by administration of GI-5005 and included lymphocyte proliferation as assessed by $^3$H-thymidine incorporation, cell-mediated cytotoxicity assays employing $^{51}$Cr-labeled target cells, quantification of cytokine secretion, and protection from tumor challenge.

(a) GI-5005 Induces Antigen-Specific Lymphocyte Proliferation.

In a preliminary experiment to evaluate the immunogenicity of GI-5005, C57BL/6 mice were injected weekly for three weeks with 5 YU (50 million) heat-inactivated GI-5005 yeast cells. The mice showed no apparent adverse effects from immunization. Spleen cells were obtained seven days after the final immunization and single cell suspensions were stimulated in vitro with either nothing, EL4 lymphoma cells, EL4-NS3 (EL4 stably expressing HCV NS3), rVV-NS3 (recombinant vaccinia virus encoding HCV NS3) or rVV-Core. Lymphocyte proliferation was assessed using a standard thymidine incorporation assay after 5 days in culture. More specifically, spleen cells from C57BL/6 mice that were injected with 5 YU GI-5005 were placed in individual wells of 96-well U-bottomed tissue culture plates (400,000 cells/well) and stimulated in vitro with: nothing, mitomycin C-treated EL4 (10,000 cells/well), mitomycin C-treated EL4-NS3 (10,000 cells/well), rVV-NS3 (400,000 pfu/well) or rVV-Core (400,000 pfu/well). 3HTdR was added on day 5 and the plates were harvested 18 hours thereafter. Results are expressed as the average CPM +/-S.D. for triplicate samples. The results presented in FIG. 2 show that GI-5005 induces NS3- and Core-specific lymphocyte proliferation.

(b) GI-5005 Induces Antigen-Specific Cytotoxic Effector Cell Responses:

GI-5005 Induces Cytotoxic Effector Cells that Kill Tumor Cells Stably Expressing HCV NS3

FIG. 3 shows that immunization with GI-5005 induces cytotoxic effector cells that can kill HCV NS3-expressing tumor cells. Specifically, spleen cells from C57BL/6 mice that were injected weekly for three weeks with 5 YU GI-5005 were placed in individual wells of either 25 cm$^2$ tissue culture flasks at 30×10$^6$ cells/flask (FIGS. 3A-3B) or 24-well flat-bottomed tissue culture plates at 6×10$^6$/well (FIG. 3C). Spleen cells were stimulated in vitro (IVS) for 6 days with either 1 YU (10$^7$ yeast cells) GI-5005/flask (FIG. 3A); with nothing, 1 YU/flask GI-1001 or 1 YU/flask GI-5005 (FIG. 3B); or with 6×10$^6$ pfu/well rVV-lac or rVV-NS3 (FIG. 3C). Spleen cells in culture with rVV-lac or rVV-NS3 were expanded for an additional 3 days in the presence of 10% T-stim as a source of T cell growth factors. At the end of the 6 (FIGS. 3A,3B) or 9 (FIG. 3C) day IVS culture period, doubling dilutions of the spleen cell cultures were mixed with ten thousand $^{51}$Cr-labeled EL4 or EL4-NS3 cells as indicated. E:T ratio refers to the effector:target ratio based on spleen effector cell concentrations at the start of the IVS culture period. Results are expressed as the average percent specific lysis +/-S.D. for triplicate samples isolated after six hours of co-culture in 96-well V-bottomed plates. Percent spontaneous chromium release values were 19% for EL-4 (FIG. 3A), 40% for EL4-NS3 (FIGS. 3A,3B) and 29% for EL4-NS3 (FIG. 3C).

In the results presented in FIG. 3A, spleen cells derived from GI-5005 immunized C57BL/6 mice were stimulated in vitro with GI-5005 yeast, at a yeast to spleen cell ratio of 1:3, for 6 days prior to testing on $^{51}$Cr-labeled non-transfected EL4 lymphoma cells or on EL4 cells stably expressing HCV-NS3 (EL4-NS3). The stimulated spleen cells killed EL4-NS3 targets in a dose-dependent manner. In contrast, significantly less killing was observed on non-transfected EL4 cells. In addition to providing evidence that immunization with GI-5005 induced NS3-specific cytotoxic effector cells, these data also indicated that GI-5005 yeast could be used in vitro to re-stimulate NS3-specific cytotoxic effector cells. The results presented in FIG. 3B provide further confirmation for this finding and show that in vitro stimulation (IVS) of spleen cells from GI-5005-immunized mice with GI-5005 reveals cytotoxic effector cells capable of enhanced cytotoxic activity against EL4-NS3, as compared to IVS with nothing (nil) or with vector control yeast (GI-1001). The requirement for exposure to some form of HCV NS3 antigen to activate cytotoxic effector cells activity during the IVS period was further investigated using stimulation with recombinant vaccinia virus encoding NS3 (rVV-NS3; FIG. 3C). These data show that NS3-specific cytotoxic effector cells present in the spleen of immunized mice are stimulated by IVS with rVV-NS3 as compared to IVS with rVV-lac, a recombinant virus encoding the irrelevant antigen beta-galactosidase.

GI-5005 Induces Cytotoxic Effector Cells that Kill Tumor Cells Infected with Recombinant Vaccinia Virus Encoding HCV NS3 or Core The results presented above demonstrated that immunization with GI-5005 leads to induction of cytotoxic effector cells that can kill syngeneic tumor cells expressing NS3. However, GI-5005 also expresses the HCV Core antigen. Attempts to derive stably transfected tumor cell lines expressing HCV Core protein were unsuccessful. To overcome the lack of a Core-expressing target cell, the studies presented in FIG. 4 were performed. In brief, $H-2^d$-bearing P815 leukemia cells were infected overnight with recombinant vaccinia viruses encoding either HCV NS3 or HCV Core prior to their use in a standard chromium release assay employing spleen cells from BALB/c mice that had been immunized with either GI-5005 or GI-5003 (a Tarmogen™™ expressing full-length HCV-NS3 but not Core) and stimulated in vitro for 5 days in the presence of GI-5005. More particularly, spleen cells from BALB/c mice that were injected weekly for three weeks with 5 YU GI-5005 (GI-5005) or 5 YU GI-5003 (GI-5003) were placed in individual wells of 24-well flat-bottomed tissue culture plates (8×10⁶/well) and were stimulated in vitro with GI-5005 (1×10⁶/well) for 5 days. At the end of the IVS culture period, doubling dilutions of the spleen cell cultures were mixed with ten thousand 51 Cr-labeled P815 leukemia cells that had been infected overnight with recombinant vaccinia virus encoding HCV NS3 (FIG. 4A) or HCV Core (FIG. 4B). E:T ratio refers to the effector:target cell ratio based on spleen effector cell concentrations at the start of the IVS culture period. Results are expressed as the average percent specific lysis +/−S.D. for triplicate samples isolated after 6 hours of co-culture in 96-well V-bottomed plates. Percent spontaneous chromium release values were 21% for P815-rVV-NS3 and 40% for P815-rVV-Core.

FIGS. 4A and 4B shows that GI-5005 induces cytotoxic cells that can kill tumor cells infected with either rVV-NS3 (FIG. 4A) or rVV-Core (FIG. 4B) whereas killing induced by GI-5003 is restricted to NS3. In summary, the results presented in FIGS. 3 and 4 indicate that immunization with GI-5005 induces NS3- and Core-specific cytotoxic effector cell activity.

(c) GI-5005 Induces Cells that Secrete Pro-Inflammatory Cytokines

FIG. 5 shows the cytokines that are secreted when spleen cells from either naïve or GI-5005 immunized C57BL/6 mice are placed in tissue culture with GI-5005 yeast. Cell-free supernatants were collected 48 hours after initiation of culture and cytokine concentrations were determined using the flow cytometer-based Luminex™ assay (Biosource). More specifically, spleen cells from naïve C57BL/6 mice or from C57BL/6 mice that received three weekly injections of 5 YU GI-5005 were placed in individual wells of 24-well flat-bottomed tissue culture plates (10×10⁶/well). Spleen cells were stimulated with either GI-5005 (1×10⁶ yeast cells/well) or PMA (15 ng/mL) plus Ionomycin (750 ng/mL). Cell-free supernatants were collected at 48 hours after initiation of culture and cytokines were quantified by the University of Colorado Cancer Center Flow Cytometer Facility using the flow-cytometer Luminex™ assay (Biosource). IFN-g=IFN-γ; TNF-a=TNF-α.

These results show that GI-5005 administration elicits T cells that secrete IL-2 and IL-5, as well as the pro-inflammatory cytokines IL-6, GM-CSF, IFN-γ and TNF-α. It is important to note that the cytokine response of spleen cells from immunized mice exposed to yeast in vitro is comparable in magnitude to that observed upon polyclonal stimulation of T cells from naïve C57BL/6 mice with PMA plus ionomycin. In addition, FIG. 5 also shows the cytokine response of naïve C57BL/6 spleen cells to yeast and indicates that the innate response to yeast includes secretion of IL-6, IL-12 and TNF-α, presumably derived from monocytes and dendritic cells in the population. Similar results were obtained with spleen cells from naïve and immunized BALB/c mice (see FIGS. 8 and 11).

(d) Effect of Repeated Administration on Immune Responses Induced with GI-5005

Figure 8A:
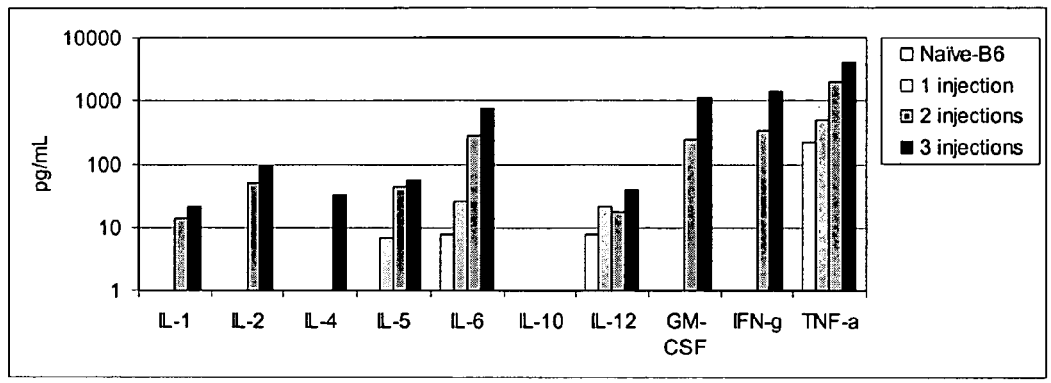
FIGS. 8A and 8B are graphs showing pro-inflammatory yeast-specific cytokine-secreting cells induced by one, two or three weekly immunizations with a vaccine of the invention expressing a truncated NS3-Core fusion protein.
Figure 8B:
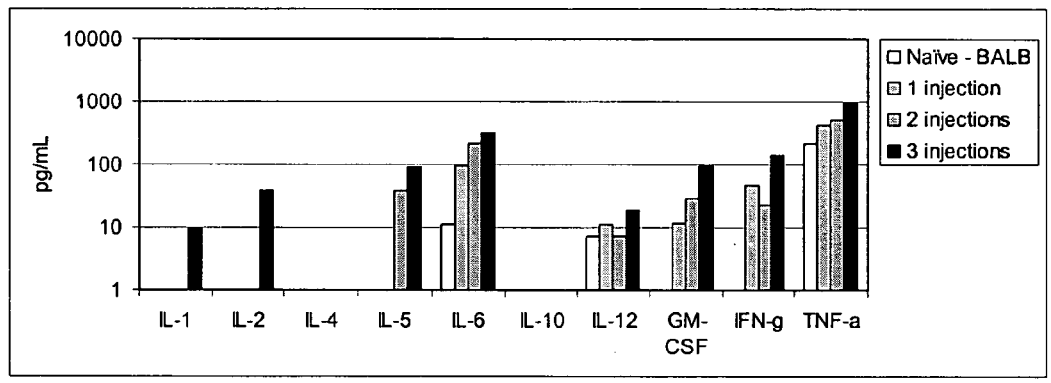

The results presented in FIGS. 6, 7 and 8 are from experiments comparing one, two or three weekly immunizations with GI-5005 conducted in both C57BL/6 and BALB/c mice. FIG. 6 examines NS3- and Core-specific lymphocyte proliferation, FIG. 7 shows the induction of NS3- and Core-specific cytotoxic cell activity and FIG. 8 shows cytokine secretion profiles. Overall, these results indicate that a single injection of GI-5005 induces a weak response that is significantly enhanced by additional administrations.

FIG. 6 shows the results of a lymphocyte proliferation assay performed with spleen cells from C57BL/6 mice that received one, two or three weekly immunizations with GI-5005. Specifically, spleen cells from C57BL/6 mice that received one, two or three weekly injections with 5YU GI-5005 were placed in individual wells of 96-well U-bottomed tissue culture plates (400,000 cells/well) and stimulated in vitro with either nothing, rVV-NS3, rVV-Core or rVV-rastafar (100,000 pfu/well). 3HTdR was added on day 5 and the plates were harvested 18 hours thereafter. Results are expressed as the average CPM +/−S.D. for triplicate samples. The response of HCV NS3 and Core-specific lymphocytes increased in proportion with the number of immunizations and the calculated stimulation indices improved from 1.8 to 2.8 against rVV-NS3 and from 6.5 to 8.6 against rVV-Core with one vs. three immunizations. No stimulation was observed against rVV-rastafar (encoding human Ras), confirming the antigen-specificity of the response induced by GI-5005.

FIG. 7 shows the results of chromium release assays performed with spleen effector cells derived from C57BL/6 and BALB/c mice that received one, two or three immunizations with GI-5005. Specifically, spleen cells from C57BL/6 mice (FIGS. 7A and 7B) or BALB/c mice (FIGS. 7C and 7D) that received one, two or three weekly injections with 5 YU GI-5005 were placed in individual wells of 24-well flat-bottomed tissue culture plates (10×10⁶/well) and stimulated in vitro with GI-5005 (1×10⁶/well) for 5 days. At the end of the IVS culture period, doubling dilutions of the spleen cell cultures were mixed with ten thousand 51Cr-labeled EL4 lymphoma cells (FIGS. 7A and 7B) or P815 leukemia cells (FIGS. 7C and 7D) that had been infected overnight with recombinant vaccinia virus encoding HCV NS3 (FIGS. 7A and 7C) or HCV Core (FIGS. 7B and 7D). E:T ratio refers to the effector:target cell ratio based on spleen effector cell concentrations at the start of the IVS culture period. Results are expressed as the average percent specific lysis +/−S.D. for triplicate samples isolated after 6 hours of co-culture in 96-well, V-bottomed plates. Percent spontaneous $^{51}$Cr release was 10% for EL-4-rVV-NS3, 10% for EL4-rVV-Core, 12% for P815-rVV-NS3 and 11% for P815-rVV-Core. Confirming the findings reported in FIG. 4, the results presented in FIG. 7 show dose-dependent killing on syngeneic tumor cell targets infected with either rVV-NS3 or rVV-Core which increases in proportion to the number of immunizations.

The results presented in FIG. 8 show the cytokine secretion profiles of spleen cells derived from C57BL/6 and BALB/c mice that received one, two or three immunizations with GI-5005 in response to in vitro stimulation with GI-5005. Specifically, spleen cells from C57BL/6 mice (upper panels) or BALB/c mice (lower panels) that received one, two or three weekly injections with 5 YU GI-5005 were placed in individual wells of 24-well flat-bottomed tissue culture plates (10×10⁶/well) and stimulated in vitro with GI-5005 (1×10⁶/well). Cell-free supernatants were collected at 48 hours after initiation of culture and cytokines were quantified by the University of Colorado Cancer Center Flow Cytometer Facility using the flow-cytometer based Luminex™ assay (Biosource). IFN-g=IFN-γ; TNF-a=TNF-α. These results show that the cytokine response of cells from immunized mice against yeast antigens is predominantly of the $T_H1$-like, pro-inflammatory variety and that more than one immunization is required to see the full spectrum of response. It is important to further note that the TH2 cytokines IL-4 and IL-10 are generally not detected, suggesting that yeast vehicles of the invention primarily induce cellular rather than humoral immunity.

The data presented above indicated that immune responses induced by GI-5005 were enhanced by repeated weekly administrations. To explore boosting of immune responses with GI-5005, the experiment outlined in Table 2 was undertaken. In brief, female BALB/c mice received five weekly injections of GI-5005 followed by no boosting or by boosting at weekly, bi-weekly, monthly or bimonthly intervals. Mice were sacrificed 16 days after the last boosting. The results importantly show that repeated weekly immunization does not result in induction of neutralization and/or tolerance in that even after 12 weekly injections a subsequent administration resulted in boosting as measured by lymphocyte proliferation and cell-mediated cytotoxicity assays.

TABLE 2

Immunization and boosting schedule with GI-5005

| Group | D 0 | D 7 | D 14 | D 21 | D 28 | D 35 | D 42 | D 49 | D 56 | D 63 | D 70 | D 77 | D 84 | D 100 |
|---|---|---|---|---|---|---|---|---|---|---|---|---|---|---|
| PBS control | — | — | — | — | — | — | — | — | — | — | — | — | — | Sacrifice |
| No boost | I | I | I | I | I | — | — | — | — | — | — | — | — | Sacrifice |
| 2 month boost | I | I | I | I | I | — | — | — | — | — | — | — | I | Sacrifice |
| Monthly boost | I | I | I | I | I | — | — | — | I | — | — | — | I | Sacrifice |
| Bi-weekly boost | I | I | I | I | I | — | I | — | I | — | I | — | I | Sacrifice |
| Weekly boost | I | I | I | I | I | I | I | I | I | I | I | I | I | Sacrifice |

I = immunization with GI-5005

Figure 9:
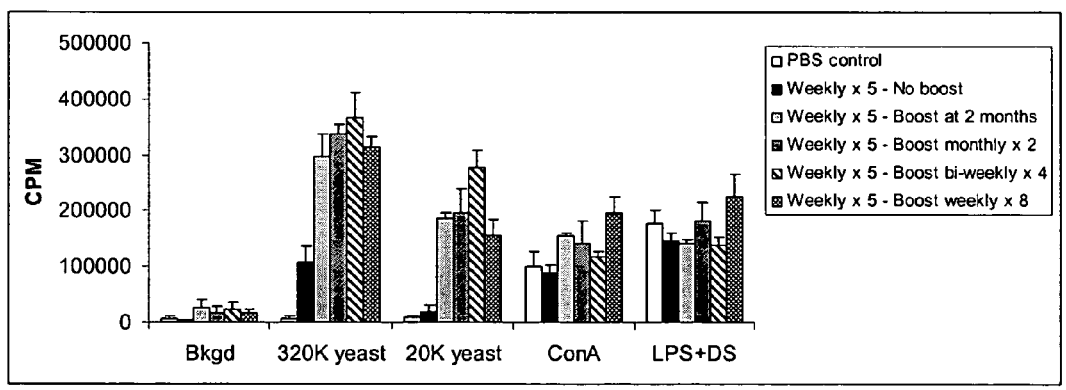
FIG. 9 is a graph illustrating lymphocyte proliferation in spleen cells derived from BALB/c mice that that were immunized and boosted with a vaccine of the invention expressing a truncated NS3-Core fusion protein under different immunization protocols.
Figure 13A:
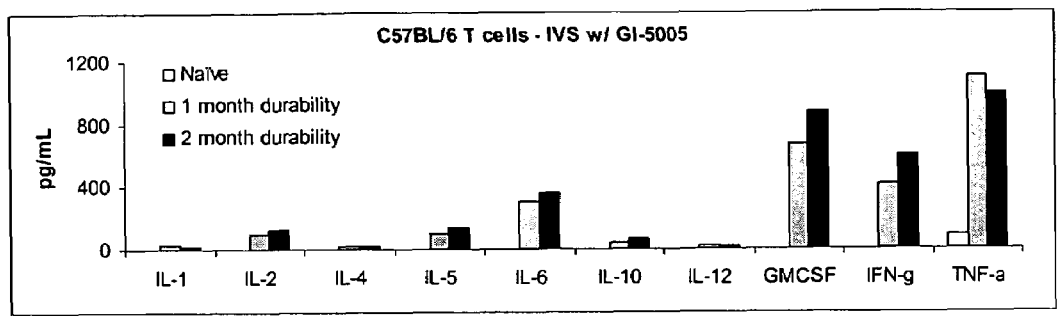
FIGS. 13A-13D are graphs showing the durability of yeast- and NS3-specific cytokine-secreting cells induced with a vaccine of the invention expressing a truncated NS3-Core fusion protein.
Figure 13B:
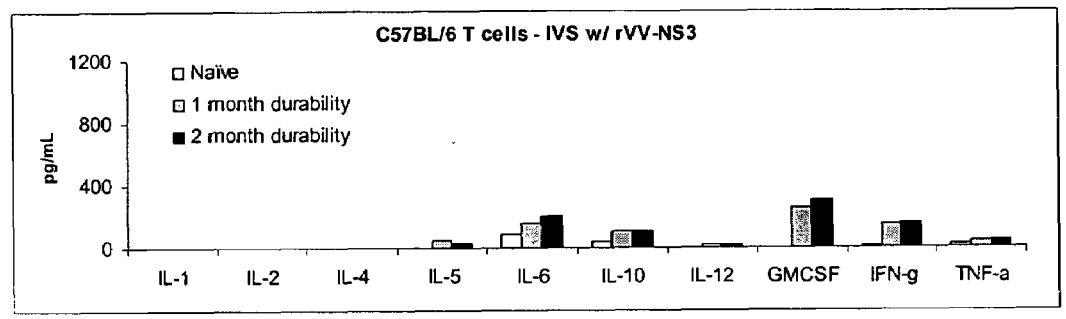
Figure 13C:
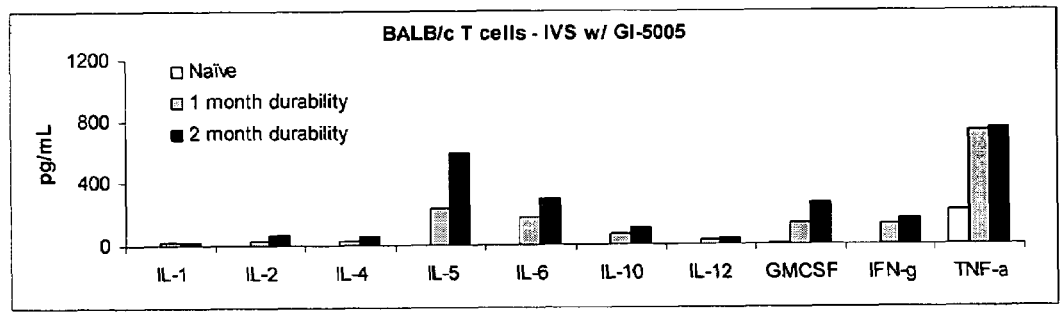
Figure 13D:
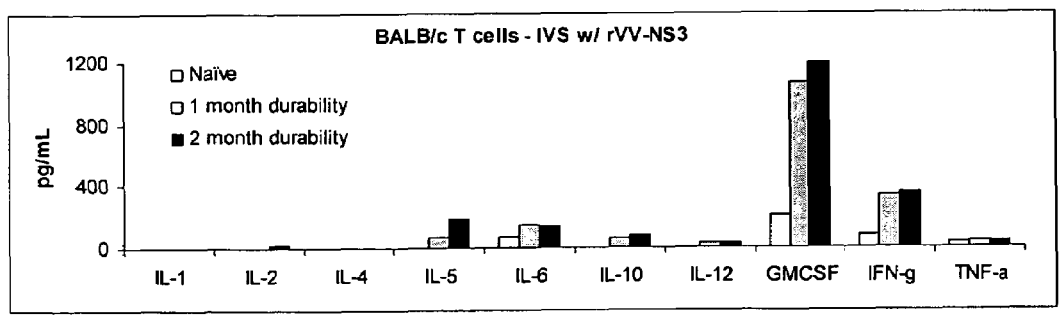
Figure 14A:
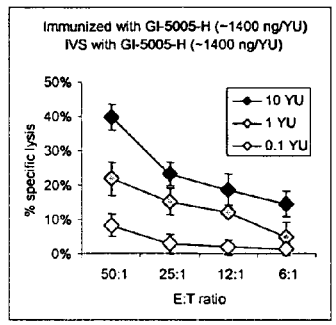
FIGS. 14A-14I are graphs illustrating cytotoxic effector cell activity induced with a vaccine of the invention expressing different amounts of a truncated NS3-Core fusion protein.
Figure 14B:
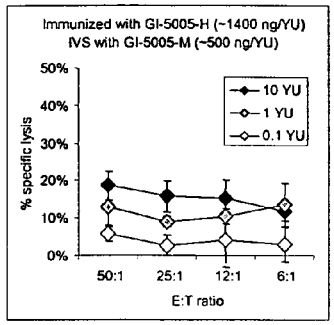
Figure 14C:
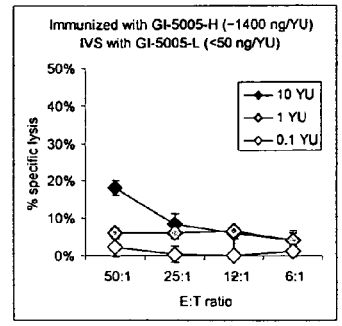
Figure 14D:
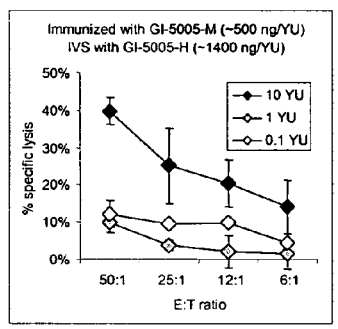
Figure 14E:
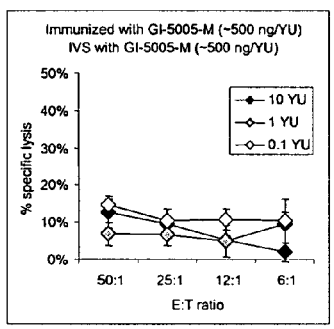
Figure 14F:
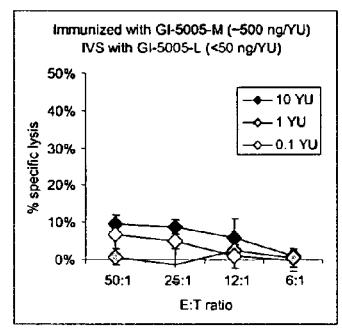
Figure 14G:
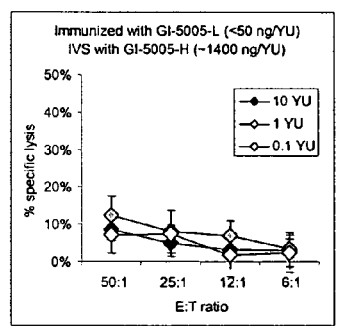
Figure 14H:
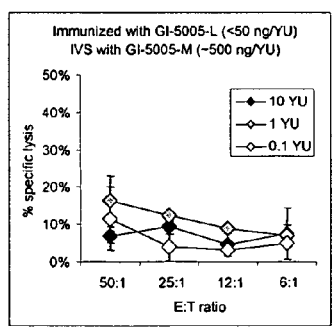
Figure 14I:
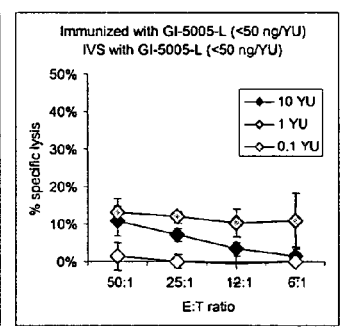

FIG. 9 shows the results of a lymphocyte proliferation assay performed with spleen cells derived from the BALB/c mice that received GI-5005 on the immunization schedule outlined in Table 2. Briefly, spleen cells from BALB/c mice that were immunized with 5 YU GI-5005 on the schedule as described in Table 2 were placed in individual wells of 96-well U-bottomed tissue culture plates (400,000 cells/well) and stimulated in vitro with either nothing (Bkgd), GI-5005 (320,000 or 20,000 yeast cells/well), Concanavlin A (ConA; 2.5 µg/mL) or Lipopolysaccharide+dextran sulfate (LPS+ DS; 25 µg/ml and 20 µg/mL). 3HTdR was added on day 3 and the plates were harvested 18 hours thereafter. Results are expressed as the average CPM +/−S.D. for triplicate samples. FIG. 9 shows that the boostable response against yeast-associated antigens is quite evident and there is no apparent induction of tolerance.

FIG. 10 shows the results of a chromium release assay performed with spleen effector cells derived from the BALB/c mice that were immunized and boosted as described in Table 2. Briefly, spleen cells from BALB/c mice that were immunized with 5 YU GI-5005 on the schedule as described in Table 2 were placed in individual wells of 24-well flat-bottomed tissue culture plates ($10 \times 10^6$/well) and stimulated in vitro with GI-5005 ($1 \times 10^6$/well) for 5 days. At the end of the IVS culture period, doubling dilutions of the spleen cell cultures were mixed with ten thousand $^{51}$Cr-labeled P815-NS3 leukemia cells. E:T ratio refers to the effector:target cell ratio. Results are expressed as the average percent specific lysis +/−S.D. for triplicate samples isolated after 6 hours of co-culture in 96-well, V-bottomed plates. Percent spontaneous 51Cr release was 12% for P815-NS3. Confirming the findings reported in FIG. 9, the results presented in FIG. 10 show dose-dependent killing on syngeneic tumor cells stably expressing HCV NS3 and further demonstrate the durability as well as boostability of the CTL response induced by GI-5005.

(e) Durability of Immune Responses Induced with GI-5005

In order to evaluate the robustness of the cellular immune responses induced upon immunization with GI-5005, C57BL/6 and BALB/c mice that received three weekly doses of GI-5005 were sacrificed one month and two months post-dosing. FIG. 11 examines the durability of yeast-specific lymphocyte proliferation while FIG. 12 examines the durability of NS3- and Core-specific cytotoxic cell activity and FIG. 13 shows yeast- as well as NS3-specific cytokine secretion profiles. Overall, these results suggest that administration of GI-5005 induces memory T cell responses that are long lasting and robust.

Durability of Lymphocyte Proliferative Responses Induced with GI-5005

The results presented in FIG. 11 show that proliferative responses against yeast antigens last at least 2 months following three weekly immunizations. Briefly, spleen cells from C57BL/6 (FIG. 11A) or BALB/c (FIG. 11B) mice that received either nothing (Naïve) or three weekly immunizations with 5 YU GI-5005, and were rested for five (1 month durability) or nine (2 month durability) weeks prior to sacrifice, were placed in individual wells of 96-well U-bottomed tissue culture plates (400,000 cells/well) and stimulated in vitro with either nothing (Bkgd) or GI-5005, (400,000 yeast cells/well). $^3$HTdR was added on day 5 and the plates were harvested 18 hours thereafter. Results are expressed as the average CPM +/−S.D. for triplicate samples. It is important to note these results examine yeast-specific as opposed to HCV NS3- or Core-specific proliferative responses as described in FIGS. 2 and 6. The stimulation indices against yeast antigens in these particular experiments range from approximately 11 to 77.

Durability of Cytotoxic Effector Cell Responses Induced with GI-5005

As shown in FIG. 12, and similar to results regarding lymphocyte proliferative responses, the durability of cytotoxic effector cell activity induced with GI-5005 is at least two months. Briefly, spleen cells from C57BL/6 (FIG. 12A) or BALB/c (FIG. 12B) mice that received either nothing (Naïve) or three weekly immunizations with 5 YU GI-5005, and were rested for five (1 month durability) or nine (2 month durability) weeks prior to sacrifice, were placed in individual wells of 24-well flat-bottomed tissue culture plates ($10 \times 10^6$/ well) and stimulated in vitro with GI-5005 ($1 \times 10^6$/well) for 5 days. At the end of the IVS culture period, doubling dilutions of the spleen cell cultures were mixed with ten thousand $^{51}$Cr-labeled EL4-NS3 lymphoma cells (FIG. 12A) or P815-NS3 leukemia cells (FIG. 12B). E:T ratio refers to the effector:target cell ratio based on spleen effector cell concentrations at the start of the IVS culture period. Results are expressed as the average percent specific lysis +/−S.D. for triplicate samples isolated after 6 hours of co-culture in 96-well, V-bottomed plates. Percent spontaneous $^{51}$Cr release was 11% for EL-4-NS3 and 11% for P815-NS3.

Durability of Cytokine Secretion Responses Induced with GI-5005

FIG. 13 shows the durability of the cytokine secretion profiles of spleen cells derived from C57BL/6 and BALB/c mice that received three weekly immunizations with GI-5005 in response to in vitro stimulation with GI-5005 and rVV-NS3. Briefly, spleen cells from C57BL/6 (FIGS. 13A and 13B) or BALB/c (FIGS. 13C and 13D) mice that received nothing (Naïve) or three weekly immunizations with 5 YU GI-5005 and were rested for five (1 month durability) or nine (2 month durability) weeks prior to sacrifice were placed in individual wells of 24-well flat-bottomed tissue culture plates ($10 \times 10^6$/well) and stimulated in vitro with GI-5005 ($1 \times 10^7$/well) or rVV-NS3 ($1 \times 10^7$ pfu/well). Cell-free supernatants were collected at 48 hours (IVS w/GI-5005) or 120 hours (IVS w/rVV-NS3) after initiation of culture. Cytokines were quantified using the Luminex™ assay (Biosource). IFN-g=IFN-γ; TNF-a=TNF-α. These results show that durability of cytokine-secreting cells induced by immunization with GI-5005 is at least two months. In contrast to the yeast-specific profile of cytokines, these data also show that the antigen-specific (i.e., NS3-specific) response, using rVV-NS3 as a stimulus, is limited predominantly to GM-CSF and IFN-γ.

(f) Comparison of Administration of Different Doses of GI-5005

The results summarized in FIGS. 14 and 15 compare the induction of cytotoxic effector cells and cytokine-secreting cells respectively by GI-5005 Tarmogen™s that express different amounts of antigen. This study was undertaken as part of the development of a potency assay.

In brief, GI-5005 Tarmogen™s were produced that express approximately 1400, 500 and <50 ng/YU of HCV NS3-Core fusion protein. This was accomplished by varying the amount of copper present during the induction period. The three Tarmogen™s are designated as GI-5005-H (1400 ng/YU; 0.02 ng protein/ng total protein), GI-5005-M (500 ng/YU; 0.008 ng fusion protein/total protein) and GI-5005-L (<50 ng/YU; <0.001 ng protein/ng total protein). Groups of five female BALB/c mice ($H-2^d$) were immunized weekly with the three different GI-5005 Tarmogen™s at three doses, 0.1, 1 and 10 YU. Mice were sacrificed seven days after the third weekly injection and their spleen cells were subjected to in vitro stimulation (IVS) as will now be described.

In FIG. 14, spleen cells from the immunized mice, pooled by group, were placed into IVS separately with each of the three different GI-5005 Tarmogen™s. Cell-mediated cytotoxic activity of the IVS cultures was assessed on $H-2^d$-bearing P815 cells stably expressing HCV NS3. Briefly, spleen cells from BALB/c mice that received three weekly injections of 0.1, 1 or 10 YU of either GI-5005-H (FIGS. 14A-14C), GI-5005-M (FIGS. 14D-14F) or GI-5000-L (FIGS. 14G-14I) were placed in individual wells of 24-well flat-bottomed tissue culture plates ($10 \times 10^6$ spleen cells/well) and stimulated in vitro (IVS) with the indicated GI-5005 Tarmogen™ ($2 \times 10^6$ yeast cells/well) for 5 days. At the end of the IVS culture period, doubling dilutions of the spleen cell cultures were mixed with ten thousand $^{51}$Cr-labeled P815-NS3 leukemia cells. E:T ratio refers to the effector:target cell ratio based on spleen effector cell concentrations at the start of the IVS culture period. Results are expressed as the average percent specific lysis +/−S.D. for triplicate samples isolated after 6 hours of co-culture in 96-well, V-bottomed plates. Percent spontaneous $^{51}$Cr release was 12% for P815-NS3. 10 YU, 1 YU & 0.1 YU in the legend of each figure refer to the amount of GI-5005 used for immunization. The data show clear dose responses based on a single parameter; that is, the amount of HCV antigen being expressed in the Tarmogen™ used for immunization or for in vitro stimulation. A similar conclusion can be drawn from the data presented in FIG. 15.

FIG. 15 shows the levels of IL-6 secreted in response to yeast-specific antigens vs. GM-CSF secreted in response to HCV NS3-specific antigen. Specifically, spleen cells from BALB/c mice that received three weekly injections of 0.1, 1 or 10 YU (X-axis) of either GI-5005-H (FIG. 15A), GI-5005-M (FIG. 15B) or GI-5000-L (FIG. 15C) were placed in individual wells of 24-well flat-bottomed tissue culture plates ($10 \times 10^6$ spleen cells/well) and stimulated in vitro (IVS) with either GI-5005-H ($2 \times 10^6$ yeast cells/well) or rVV-NS3 ($100 \times 10^6$ pfu/well). Cell-free supernatants were collected at 72 hours (IVS w/GI-5005) or 120 hours (IVS w/rVV-NS3) after initiation of culture. Cytokines were quantified using the Luminex™ assay (Biosource). In brief, these data indicate that the induction of IL-6-secreting cells is dependent on the number of Tarmogen™s that are used for immunization but is independent of the amount of HCV antigen being expressed in the Tarmogen™™. In contrast, the induction of cells secreting GM-CSF is dependent on both criteria. Based on the data presented in FIGS. 14 and 15 a minimum of 500 ng fusion protein/YU or 0.008 ng protein/ng total protein is required for inducing an antigen-specific response.

Example 6

The following example shows non-clinical pharmacology studies in mice using the GI-5005 Tarmogen™ expressing HCV antigens: tumor protection and therapy studies.

Because an in vivo animal model of protection or therapy against HCV is not available, the present inventors have used protection and therapy against HCV antigen-bearing tumors in vivo to demonstrate the activity of GI-5005.

(a) GI-5005 Induces Protective Immunity Against NS3-Expressing Tumor Cells

The experiments described above demonstrate the immunogenicity of GI-5005 in C57BL/6 and BALB/c mice. In order to determine if injection of GI-5005 yeast elicited protective immunity, BALB/c mice were injected subcutaneously once a week for three weeks with 0.1, 0.7 or 5 YU of either GI-5005 or GI-5003 (a Tarmogen™ that expresses only HCV NS3 protease), with 5 YU GI-4014 (a Tarmogen™ expressing a mutated Ras protein) as a negative control, or with nothing. One week after the final immunization, the mice were challenged with subcutaneously injected syngeneic A20 tumor cells stably transfected with HCV NS3 (A20-NS3). Tumor volume was measured on day 21 after challenge. The data presented in FIG. 16 show that the mice that were immunized with a Tarmogen™ expressing HCV NS3 antigens, GI-5005 or GI-5003, were protected from challenge with A20-NS3 tumor cells, whereas mice immunized with nothing or with GI-4014 were not. Results are expressed as the mean tumor volume +/−S.D. These results show that GI-5005 induces dose- and antigen-dependent immune responses that protect mice from syngeneic tumor cells expressing HCV NS3.

Figure 17:
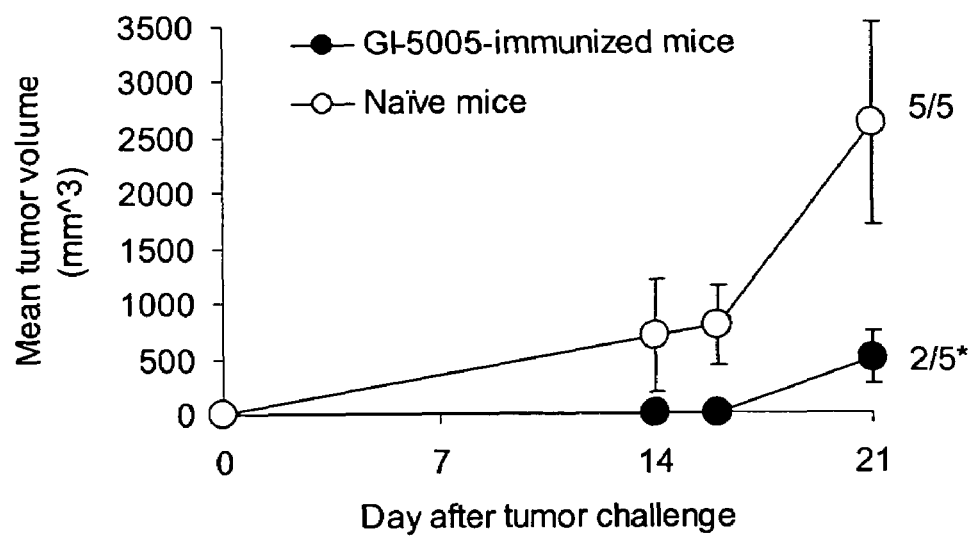
FIG. 17 is a graph illustrating that a vaccine of the invention expressing a truncated NS3-Core fusion protein induces protective immunity in C57BL/6 mice against challenge with syngeneic tumor cells expressing HCV NS3.

This experiment was repeated in C57BL/6 mice that were injected weekly for three weeks with GI-5005 and challenged seven days thereafter with EL4-NS3 lymphoma cells injected subcutaneously. Briefly, C57BL/6 mice (5 per group) were injected subcutaneously weekly for three weeks with nothing (Naive) or with 5 YU GI-5005. Mice were challenged 7 days after the final immunization with $5 \times 10^4$ A20-NS3 injected subcutaneously. Tumors were measured on the indicated day after challenge. Results are expressed as the mean tumor volume +/−S.D. Numbers refer to the number of animals with measurable tumors (* Tumors excised from immunized mice were found to no longer express NS3). The results presented in FIG. 17 show that mice injected with GI-5005 were protected from challenge with EL4-NS3 whereas naïve mice were not. Injection of GI-5005 did not protect mice from challenge with EL4 alone indicating that protective immunity was antigen-specific (data not shown). To determine whether the tumors that had grown in the immunized mice were still expressing HCV NS3, the tumors were excised from the two GI-5005 immunized mice that showed evidence of tumor growth, as well as from the five naïve mouse controls, and placed in tissue culture medium containing the antibiotic G4.18. In EL4-NS3, the mammalian expression vector encoding HCV NS3 also contains a neomycin resistance gene that allows transfectants to grow in the presence of the neomycin analog G4.18, thereby maintaining stable expression of HCV NS3. Whereas EL4-NS3 tumor cells excised from naïve mice grew out in the presence of G4.18, tumors from the GI-5005-immunized mice did not. This observation suggests that there was immunological pressure to eliminate expression of the transfected antigen. These observations indicate that GI-5005 induces protective immune responses in vivo against challenge with syngeneic tumor cells expressing NS3.

(b) Immune Responses in "Protected" Mice

Figure 18:
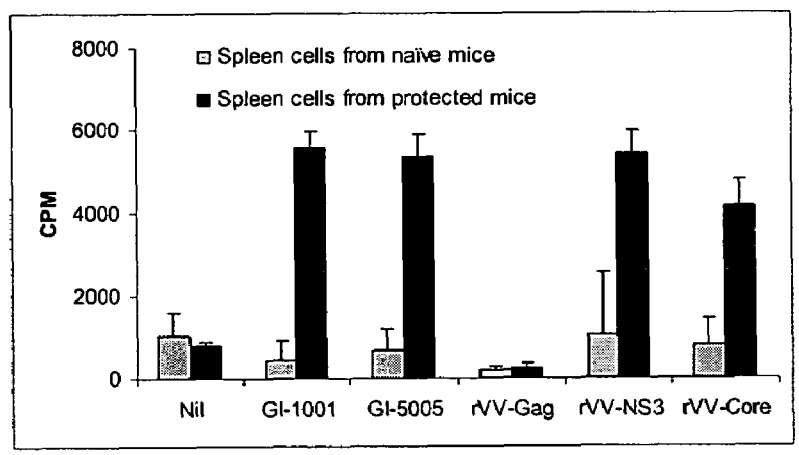
FIG. 18 is a graph showing lymphocyte proliferative activity in spleen cells from "protected" mice.
Figure 19:
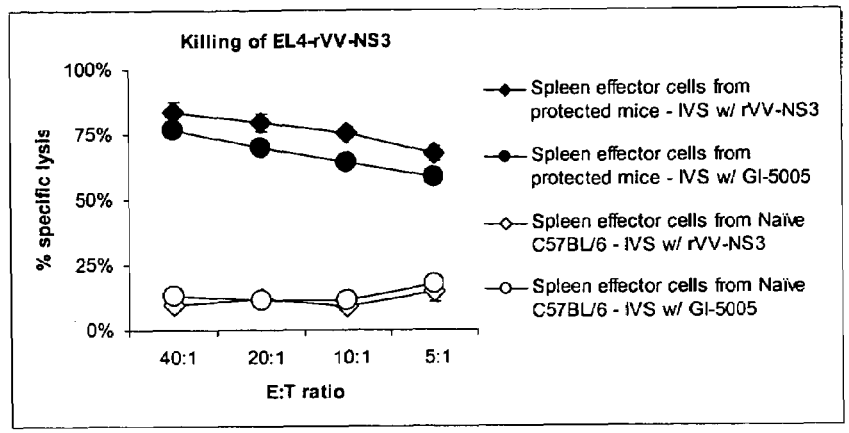
FIG. 19 is a graph showing cytotoxic effector cell activity in spleen cells from "protected" mice.

The availability of "protected" mice that had rejected syngeneic tumor cells expressing HCV NS3 provided the opportunity to examine antigen-specific immune responses in the setting of protective immunity. Spleen cells from the five mice described above that rejected EL4-NS3 tumor cells were pooled and placed in individual wells of 96-well U-bottomed tissue culture plates ($4\times10^5$ cells/well) and stimulated with either nothing, GI-1001 ($2\times10^5$ yeast cells/well), GI-5005 ($2\times10^5$ yeast cells/well), rVV-Gag ($1\times10^5$ pfu/well), rVV-NS3 ($1\times10^5$ pfu/well), or rVV-Core ($1\times10^5$ pfu/well). $^3$HTdR was added on day 5 and the cells were harvested 18 hours thereafter. Results are expressed as the average CPM +/−S.D. for quadruplicate samples. FIG. 18 shows the proliferative response of spleen cells derived from protected mice to yeast-specific, as well as HCV NS3- and HCV Core-specific stimuli. FIG. 19 examines their cytotoxic effector cell activity. In this experiment, spleen cells from the five immunized mice that rejected EL4-NS3 tumor cells or from naïve mice were pooled together and placed in individual wells of 24-well flat-bottomed tissue culture plates ($8\times10^6$ spleen cells/well) and stimulated in vitro (IVS) with either GI-5005 ($1\times10^6$ yeast cells/well) or rVV-NS3 ($8\times10^5$ pfu/well) for 5 days. At the end of the IVS culture period, doubling dilutions of the spleen cell cultures were mixed with ten thousand $^{51}$Cr-labeled EL4 target cells that had been infected overnight with rVV-NS3. E:T ratio refers to the effector:target cell ratio based on spleen effector cell concentrations at the start of the IVS culture period. Results are expressed as the average percent specific lysis +/−S.D. for triplicate samples isolated after 5 hours of co-culture in 96-well, V-bottomed plates. Percent spontaneous $^{51}$Cr release was 33% for EL4-rVV-NS3. Taken together, these findings suggest that protected mice, i.e. immunized mice that rejected NS3-expressing tumor cells, have enhanced immune responses to HCV NS3 as compared to mice that were simply immunized as shown in Example 5 above.

(c) GI-5005 Stimulates Cytotoxic Effector Cell Activity in Spleen Cells Isolated from Naïve Tumor-Bearing Mice The results presented above suggest that exposure of GI-5005 mice to a secondary source of HCV antigen, namely tumor cells expressing HCV NS3, results in a boosting effect as evidenced by enhanced proliferative and cytotoxic effector cell responses. In order to determine if GI-5005 yeast could further stimulate T cell activity from antigen-bearing mice, thus mimicking T cell activation in chronic HCV-infected patients, naïve C57BL/6 mice were injected subcutaneously with EL4-NS3 tumor cells. After 3 weeks, when tumor volumes reached approximately 2500 mm$^3$, the mice were sacrificed and spleen cells were incubated with either vector control (GI-1001) or GI-5005 yeast. Cytotoxic effector cell activity against rVV-NS3 infected EL4 target cells was assessed six days after initiation of in vitro stimulation. Specifically, spleen cells from five naive mice that were injected with EL4-NS3 tumor cells 21 days previously were pooled together and placed in individual wells of 24-well flat-bottomed tissue culture plates ($8\times10^6$ spleen cells/well) and stimulated in vitro (IVS) with either GI-1001 or GI-5005 ($1\times10^6$ yeast cells/well) for 6 days. At the end of the IVS culture period, doubling dilutions of the spleen cell cultures were mixed with ten thousand $^{51}$Cr-labeled EL4 target cells that had been infected overnight with rVV-NS3. E:T ratio refers to the effector:target cell ratio based on spleen effector cell concentrations at the start of the IVS culture period. Results are expressed as the average percent specific lysis +/−S.D. for triplicate samples isolated after 5 hours of co-culture in 96-well, V-bottomed plates. Percent spontaneous $^{51}$Cr release was 33% for EL4-rVV-NS3. The results presented in FIG. 20 show that GI-5005 can stimulate cytotoxic effector cells derived from mice bearing tumors expressing HCV-NS3.

(d) GI-5005 Induces Therapeutic Activity Against NS3-Expressing Tumor Cells

Figure 20:
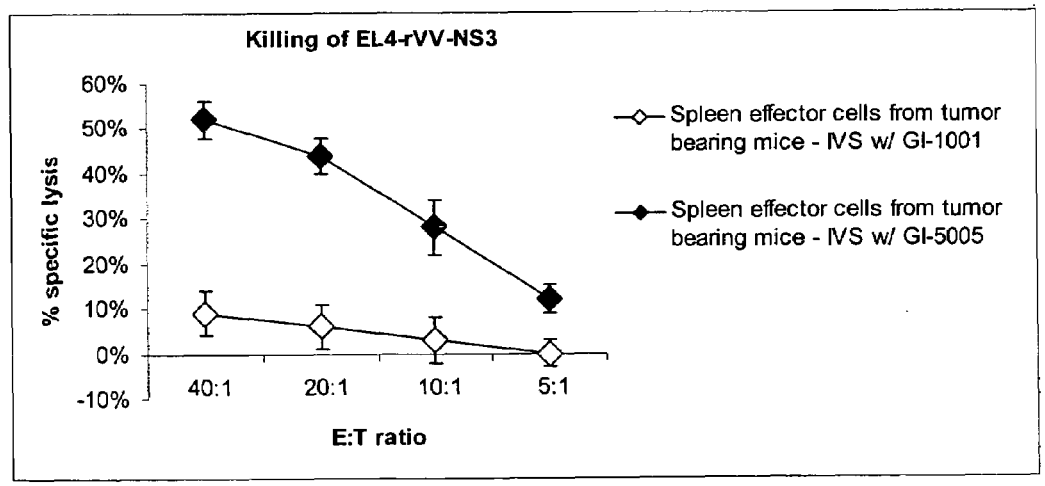
FIG. 20 is a graph illustrating that a vaccine of the invention expressing a truncated NS3-Core fusion protein stimulates cytotoxic effector cell activity in spleen cells isolated from naïve tumor-bearing mice.

The results presented in FIG. 20 show that GI-5005 can re-stimulate NS3-specific cytotoxic effector activity from spleen cells of C57BL/6 mice bearing EL4-NS3-expressing tumors. This suggests that a therapeutic effect might also be attainable. To assess this possibility, BALB/c mice (5 per group) were injected subcutaneously with syngeneic $1.25\times10^5$ A20-NS3 B lymphoma cells stably transfected with DNA encoding HCV NS3. Beginning seven days after tumor implantation, the mice were immunized once a week for three weeks with either PBS or with YU GI-5005. Tumor growth was monitored and the mice were sacrificed 28 days after tumor implantation when the tumors in the PBS group reached 2500 mm$^3$. Results in FIG. 21 are expressed as the mean tumor volume +/−S.D and numbers refer to the number of animals with measurable tumors (* Tumors excised from all tumor bearing mice were found to still express NS3).

Figure 21:
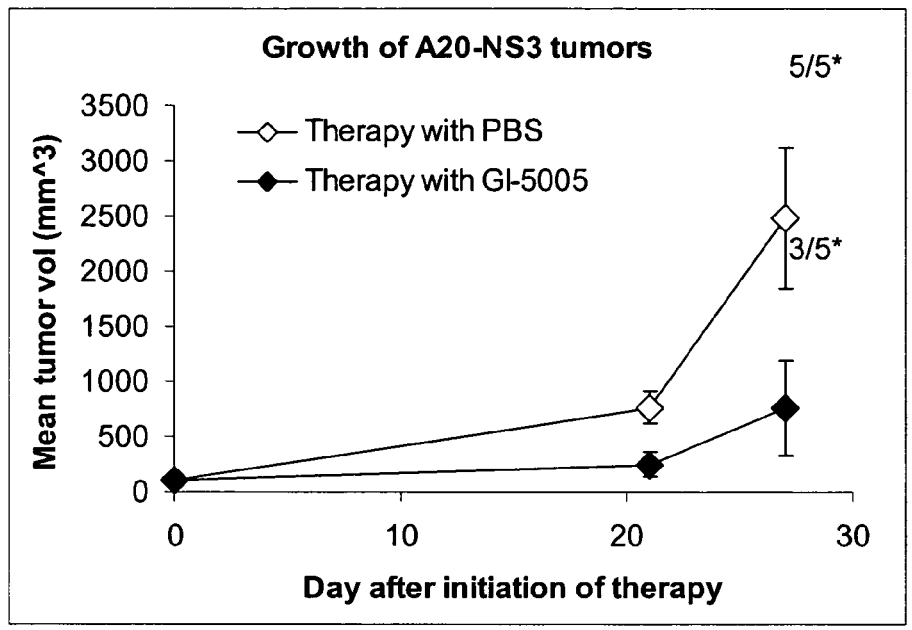
FIG. 21 is a graph showing that a vaccine of the invention expressing a truncated NS3-Core fusion protein induces therapeutic immunity in BALB/c mice bearing syngeneic B cell lymphomas expressing HCV NS3.

FIG. 21 shows that therapeutic administration of GI-5005 results in tumor remission. In brief, whereas all five tumor-bearing mice that were treated with PBS showed tumor growth, only three out five that were treated with GI-5005 exhibited tumor growth and the tumors that arose in the treated animals appeared to be growing much more slowly (mean tumor volume in tumor-bearing mice in the PBS treated group was 2488+/−636 vs. 1264+/−548 mm$^3$ in the GI-5005 treated group). However, in contrast to the results obtained with EL4-NS3 as described above, the HCV NS3 protein was still being expressed in all of the tumors from A20-NS3 tumor bearing mice (data not shown).

Figure 22A:
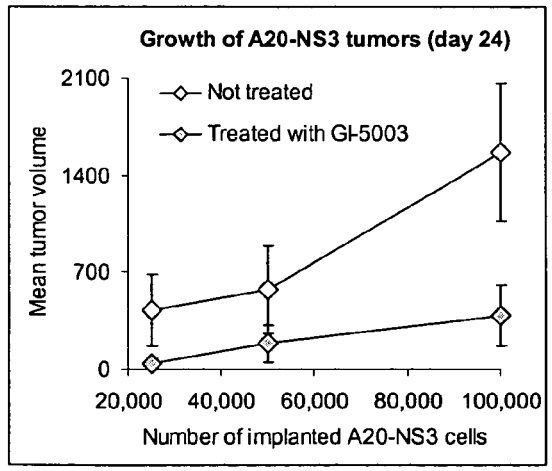
FIGS. 22A and 22B are graphs showing that a vaccine of the invention expressing a truncated NS3-Core fusion protein induces therapeutic immunity in BALB/c mice bearing syngeneic B cell lymphomas expressing HCV NS3.
Figure 22B:
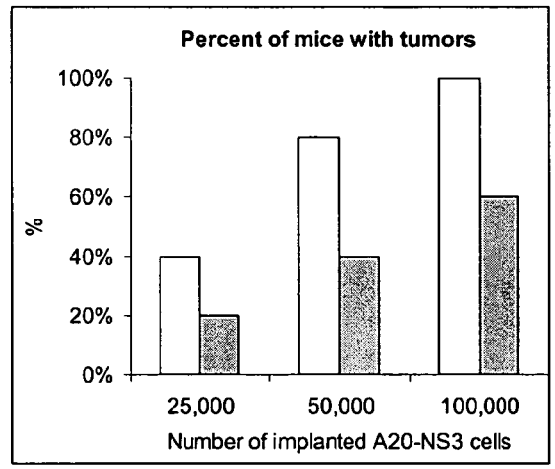

The immunotherapeutic property of GI-5005 was confirmed in a second study as shown in FIG. 22 in which the number of implanted tumor cells was varied. Briefly, BALB/c mice (5 per group) were injected subcutaneously with $2.5\times10^4$, $5.0\times10^4$, or $1\times10^5$ A20-NS3 B lymphoma cells. Mice were therapeutically immunized by subcutaneous injection at skin sites distal to the tumor on days 7, 14 and 21 after tumor implantation with either PBS or with 10 YU GI-5005. Tumor volume was measured on the indicated day after initiation of therapy. Results are expressed as the mean tumor volume +/−S.D (FIG. 22A) and as the percentage of tumor bearing mice (FIG. 22B) on day 24 after initiation of therapy.

Example 7

The following example describes toxicity studies with the yeast vaccines of the present invention.

As described above, the GI-5005 Tarmogen™ has been administered to more than 300 mice in a number of different studies to date and no grossly observable toxicity has been evident. Other related products using the yeast-based vaccine platform have been administered to mice, rats, rabbits, pig-tailed and rhesus macaque monkeys with no major observable toxicity. Because of the similarity, and therefore relevance of safety data, of other yeast based products to the GI-5005 Tarmogen™, a number of non-clinical safety assessments with these other Tarmogen™s are detailed following the toxicity data or GI-5005.

The objective of this study was to determine the toxic effects of GI-5005 in male and female New Zealand rabbits following once weekly subcutaneous administration at a fixed dose volume of 1 mL for up to thirteen consecutive weeks (dosing on Days 1, 8, 15, 22, 29, 36, 43, 50, 57, 64, 71, 78, 85 and 92), followed by specified recovery/necropsy intervals (Table 3). The dose levels were selected on the basis of available data from previous studies. The subcutaneous route is the intended route of administration of this test article in humans. The interim report as summarized below. Three treatment groups (Groups 2 to 4) of five male and five female New Zealand White rabbits were administered the test article at respective dose levels of 1, 10 and 100 Yeast Units (YU). A control group (Group 1) of five animals/sex received the vehicle, sterile phosphate buffered saline (PBS). The test article or vehicle was administered once on Days 1, 8, 15, 22, and 29. Additionally, three treatment groups (Groups 6 to 8) of five animals/sex/group (low and middle dose groups) and ten animals/sex/group (high dose group) were administered the test article at respective dose levels of 1, 10 and 100 YU. A control group (Group 5) of ten animals/sex received the vehicle PBS. In groups 5-8, the test article or vehicle was administered once on Days 1, 8, 15, 22, 29, 36, 43, 50, 57, 64, 71, 78, 85, an 92. Five animals/sex of groups 5-8 were sacrificed on Day-94. The remaining 5 animals/sex in Groups 5 and 8 were maintained for a recovery period of approximately 23 days.

All animals were observed for morbidity, mortality, injury, and availability of food and water twice daily. Detailed clinical examinations, injection site irritation evaluations, ophthalmoscopic examinations, and body weight and food consumption measurements were conducted during the course of the study. Clinical pathology evaluations (hematology, clinical chemistry, and urinalysis) were conducted on all surviving animals predose, the day following each dose, and for animals in Groups 1 to 4 at the Day 31 necropsy. Additional blood samples were collected from all surviving animals predose and 1 hour postdose for serum antibody analysis and for animals in Groups 1 to 4 at the Day 31 necropsy for serum antibody analysis. At the Day 31, Day 97 and Day 120 necropsies, all animals in the appropriate groups were euthanized and complete macroscopic and microscopic examinations were conducted, along with protocol-designated organ weight measurements.

No treatment-related effects on survival, clinical findings, food consumption, ophthalmology, or organ weights were observed. Microscopically, treatment-related changes were observed at the injection sites of both sexes at all dose levels, and included fibrosis, subacute inflammation, and necrosis. In addition, findings of granulomatous inflammation were also noted in some but not all of the injection sites. The incidence and severity of these findings were generally dose related. Granulocytic hyperplasia in the bone marrow of females at 1 YU and both sexes at 10 and 100 YU, and follicular lymphoid hyperplasia and/or reactive red pulp/stromal hyperplasia in the spleen of females at 10 YU and both sexes at 100 YU were considered a secondary response to the observed inflammation at the injection sites. These findings correlated with the microscopic findings of tissue thickening at the injection sites. Treatment related irritation, consisting of both erythema and edema, was observed at the injection sites of both sexes at 100 YU, Minimal findings were also noted in both sexes at 10 YU, suggesting a relationship to treatment. There was no indication of any sign of recovery following dosing at any of the injection sites. Although the effect was a modest, a loss of body weight was noted in both sexes at 100 YU, suggesting a relationship to treatment with GI-5005.

Treatment-related effects in hematology and clinical chemistry were observed and were considered secondary to the local inflammatory responses observed at the injection sites. Treatment-related increases in leukocyte counts, reflecting increases in neutrophil counts, were noted in all GI-5005-treated groups, with the onset and severity generally dose related. Some recovery in neutrophil levels was noted

TABLE 3

Rabbit GLP toxicity study design

| GROUP NUMBER | TREATMENT | DOSE LEVEL Yeast Units (YU)* | INITIAL M/F | TERMINAL NECROPSY (DAY 31) M/F | TERMINAL NECROPSY (Day 97) M/F | RECOVERY NECROPSY (DAY 120)* M/F |
|---|---|---|---|---|---|---|
| 1 | PBS | 0 | 5/5 | 5/5 | | |
| 2 | GI-5005 | 1 | 5/5 | 5/5 | | |
| 3 | GI-5005 | 10 | 5/5 | 5/5 | | |
| 4 | GI-5005 | 100 | 5/5 | 5/5 | | |
| 5 | PBS | 0 | 10/10 | | 5/5 | 5/5 |
| 6 | GI-5005 | 1 | 5/5 | | 5/5 | |
| 7 | GI-5005 | 10 | 5/5 | | 5/5 | |
| 8 | GI-5005 | 100 | 10/10 | | 5/5 | 5/5 |

*The test and control articles will be administered as single subcutaneous injections (1.0 mL total volume) on Days 1, 8, 15, 22, 29, 36, 43, 50, 57, 64, 71, 78, 85, and 92. One yeast unit equals 10 million heat-killed yeast cells. For reporting purposes, yeast units will be abbreviated as YU.

prior to the next dose. Treatment-related increases in globulin values were observed, with the onset and severity generally dose related. The increases tended to be progressive over time, with no indication of recovery.

Based on the conditions and findings of this study, administration of GI-5005 at dose levels of 1, 10 and 100 YU to male and female rabbits did not result in any apparent systemic toxicity. Primary treatment related findings were limited to local effects of fibrosis, subacute inflammation, and necrosis at the injection sites, which were infrequent and mild to moderate except at the highest dose tested. Injection site reactions may represent a potential dose limiting effect in the clinical setting. Concomitant increases in neutrophil counts and globulin values that were considered secondary to the local inflammatory response.

Figure 23A:
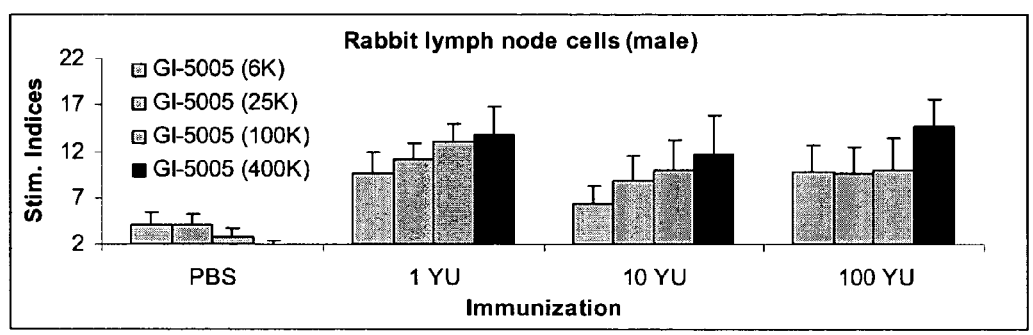
FIGS. 23A and 23B are graphs showing that a vaccine of the invention expressing a truncated NS3-Core fusion protein induces yeast-specific lymphocyte proliferation in male and female New Zealand White Rabbits.
Figure 23B:
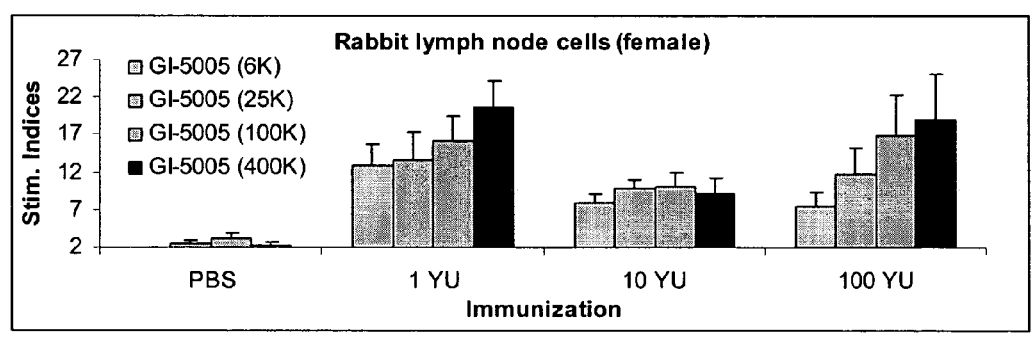

To demonstrate the immunogenicity of GI-5005 in the rabbit toxicity study, and therefore immuno-toxicologic relevance of the study, a lymphocyte proliferation assay was performed. While there are no standardized methods for assaying lymphocyte proliferation in rabbits, a non-optimized assay of lymphocyte proliferation in response to yeast proteins was performed using lymphocytes isolated from ileocecocolic and axillary lymph nodes harvested two days after the fifth immunization (Day 31). Lymph node cell suspensions from individual rabbits were placed in tissue culture in 96-well U-bottomed plates ($4 \times 10^5$ per well) with the indicated number of heat-killed GI-5005 yeast cells. Lymphocyte proliferation was determined on day 3 of culture by pulsing with 1 μCi/well of $^3$H-TdR for 18 hr. Average stimulation indices obtained with male (FIG. 23A) vs. female (FIG. 23B) lymph node cells are shown in FIG. 23 (Results are presented as average stimulation indices +/−S.E.M. obtained for evaluable lymph node cell samples from individual rabbits within each dose group). Overall, the data show that only 1 out of 10 rabbits immunized with the vehicle, PBS, showed a stimulation index of greater than 10 against the GI-5005 yeast, whereas 9 out of 10, 7 out of 10 and 8 out of 10 the rabbits immunized with 1, 10 or 100 YU GI-5005 respectively responded with a stimulation index of greater than 10. No differences between the response of male versus female rabbit lymph node cells could be discerned and a dose-response effect was not apparent.

An enzyme linked immunosorbent assay (ELISA) was used to detect and titer anti-*Saccharomyces cerevisiae* antibodies (ASCA) in the sera of rabbits (groups 1-4) that were injected with GI-5005 as part of MPI study 962-003. The serum samples examined were obtained on day 1, prior to the first injection, and on day 29, prior to the fifth weekly injection. All rabbits displayed ASCA titers of less than 1:100 at the initiation of the study (Table 4). In contrast, all rabbits that received GI-5005 showed elevated ASCA titers after administration of four weekly injections. However, the titers were low, less than 1:10,000, and no dose-response effect was observed.

TABLE 4

Summary of anti-*Saccharomyces cerevisiae* antibody (ASCA) units in sera of rabbits (Groups 1-4) that were injected with GI-5005 as part of MPI Study 962-003

| Injection | Mean ASCA units (day 1) | Mean ASCA units (day 15) | Mean ASCA units (day 29) |
|---|---|---|---|
| PBS | 4 +/− 5 | 3 +/− 4 | 6 +/− 8 |
| GI-5005 (1 YU) | 4 +/− 7 | 3 +/− 4 | 84 +/− 43 |
| GI-5005 (10 YU) | 2 +/− 2 | 6 +/− 10 | 127 +/− 162 |
| GI-5005 (100 YU) | 6 +/− 10 | 19 +/− 17 | 165 +/− 84 |

TABLE 4-continued

Summary of anti-*Saccharomyces cerevisiae* antibody (ASCA) units in sera of rabbits (Groups 1-4) that were injected with GI-5005 as part of MPI Study 962-003

| Injection | Mean ASCA units (day 1) | Mean ASCA units (day 15) | Mean ASCA units (day 29) |
|---|---|---|---|
| Positive rabbit antiserum* | 311 +/− 85 | 311 +/− 85 | 311 +/− 85 |

*A 1:1000 dilution of the positive control rabbit antiserum contained 311 +/− 85 ASCA units when run in this assay suggesting that within 95% confidence an observed ASCA unit value of less than 300 would represent a titer of less than 1:1000. Averaged data +/− S.D. is shown in the following table.

The presence of HCV-NS3- and Core-specific serum antibodies produced in rabbits immunized weekly for five weeks with PBS or with 1, 10 or 100 YU of the GI-5005 Tarmogen™ were qualitatively evaluated by Western blot analysis to gain a better understanding of the humoral antibody responses induced against the heterologous protein contained in this Tarmogen™. No HCV-specific antibodies were observed in sera obtained from any animals prior to immunization. In contrast, antibodies reacting specifically with NS3 and Core proteins were detected in serum samples from 7 of 9 tested rabbits at Day 31 after receiving 5 weekly doses of 100 YU GI-5005, and in serum samples from 1 of 3 animals in the 10 YU dose group. No HCV-specific antibodies were detected in serum samples from the PBS or 1 YU groups at day 31. This analysis shows that a dose-dependent induction of serum antibodies directed against the heterologous HCV NS3-Core protein contained in GI-5005 occurs as a result of subcutaneous administration of this Tarmogen™ in rabbits.

The preliminary 97 day and 120 day clinical pathology and gross observation data are consistent with the findings from the 31 day cohort. Thirteen weekly administrations of GI-5005 at dose levels of 1, 10 and 100 YU to male and female rabbits did not result in any apparent systemic toxicity. Primary treatment related findings were limited to local site reactions with the incidence and severity generally dose related. However, in the 100 YU dose group more severe granulomatous changes, fibrosis, and necrosis were observed in the injection site reactions, and may represent a potential dose limiting effect in the clinical setting. Histopathological analysis of this 97 day cohort is not yet available. Treatment-related increases in leukocyte counts, reflecting increases in neutrophil counts, and increases in globulin values were also observed, with the onset and severity generally dose related for both effects. The increases tended to be progressive over time, with no indication of recovery.

Gross safety assessments from 331 C57BL/6 and BALB/c mice injected with GI-5000 Tarmogen™ series products and prototypes showed no treatment-related deaths and mild to moderate hair loss and inflammation with occasional ulceration consistent with delayed-type hypersensitivity at the site of injection in approximately 5% of animals. Injection site reactivity was limited to C57BL/6 mice that are typically more sensitive to skin trauma and may have been secondary to grooming behaviors resulting from group housing conditions. No other gross clinical abnormalities or adverse reactions were observed.

TABLE 5

Summary of safety studies performed with GI-5005 Tarmogen ™ s and prototypes

| Study type | Species tested | Conclusions |
|---|---|---|
| Safety assessments | Mice | More than 300 mice have been injected with heat-inactivated intact yeast via the subcutaneous route. No adverse effects have been observed at the injection site, with the exception of mild to moderate skin reactivity noted in approximately 5% of C57BL/6 mice, and no harmful effects have been observed at any time in any mice at doses as high as 10 YU. |
| 28-day GLP safety study | Rabbits | Weekly administration of a total of five doses of GI-5005 at dose levels of 1, 10, and 100 YU to male and female rabbits did not result in any apparent systemic toxicity. Adverse reactions were limited to mild to moderate injection site reactions. The study animals tolerated the treatment regimen well. |
| 97-day GLP safety study | Rabbits | The preliminary 97 day clinical pathology and gross observation data are consistent with the findings from the 31 day cohort. No apparent systemic toxicity. Primary treatment related findings were limited to local site reactions with the incidence and severity generally dose related. Histopathological analysis of this 97 day cohort is not yet available. Treatment-related increases in leukocyte counts, reflecting increases in neutrophil counts, and increases in globulin values were also observed, with the onset and severity generally dose related for both effects. |

Each publication described or cited herein is incorporated herein by reference in its entirety.

REFERENCES

1. Kiyosawa et al., *Hepatology* 12 (1990):671-675.
2. Tong et al., *NEJM* 332 (1995):1463-1466.
3. Yano et al., *Hepatology* 23 (1996):1334-1340.
4. Gordon et al., *Hepatology* 28 (1998) 2:562-567.
5. Di Bisceglie et al., *Hepatology* 14 (1991):969-974.
6. Koretz et al., *Ann Intern Med* 119 (1993):110-115.
7. Mattson et al., *Liver* 13 (1993):274-276.
8. Tremolada et al., *J Hepatol* 16 (1992):273-281.
9. Fattovich et al., *Gastroenterology* 112 (1997):463-472.
10. Serfaty et al., *Hepatology* 27 (1998):1435-1440.
11. Armstrong et al., *Hepatology* 31 (2000):777-82.
12. Shiratori et al., *Annals of Internal Medicine*, 142 (2005):105-114.
13. Yoshida et al., IHIT Study Group (Inhibition of Hepatocarcinogenesis by Interferon Therapy). *Ann. Intem. Med* 131 (1999):174-81.
14. Okanoue et al., Viral hepatitis therapy study group. *J Hepatol* 30 (1999): 653-9.
15. Shoukry et al., *Annual Rev. Microbiol* 58 (2004):391-424.
16. Stubbs et al., *Nat Med* 7 (2001):625-629.
17. Lu et al., *Cancer Research* 64 (2004):5084-5088.
18. Haller et al., Abstract, "A novel yeast-based immunotherapeutic product for chronic hepatitis C virus infection". *AASLD Meeting*, Mar. 4-5, 2005, Chicago, Ill.
19. Mondelli et al., *Journal of Hepatology* 31 (1999):65-70.
20. Day et al., *Journal of Virology* (2002):12584-12595.
21. Lauer and Walker, *New England Journal of Medicine* 345 (2001) 1:41-52.
22. Grakoui et al., *Science Mag. Report* 342 (2003).
23. Yewdell et al., *Adv. Immunol* 73 (1999): 1-77.
24. Shoukry et al., *The Journal of Experimental Medicine* 197 (2003):1645-1655.
25. Matzinger, *Science* 296 (2002):301-305.
26. Falo et al., *Nat Med* 1 (1995):649-53.
27. Kikuchi et al., *Int. Immunopharmacol,* 2 (2002):1503-1508.
28. Tada et al., *Microbio.1 Immunol.* 46 (2002):503-512.
29. Pichuantes et al., "Expression of heterologous gene products in yeast. In Protein Engineering—Principles and Practice. J. L. Cleland and C. S. Craik, editors." *Wiley-Liss New York* (1996):129-162.
30. Underhill, *Eur. J. Immunol.* 33 (2003):1767-1775.
31. Ozinsky et al., *Proc. Natl. Acad. Sci. U S A.* 97 (2000): 13766-13771.
32. Akira et al., *Nat. Immunol.* 2 (2001):675-680.
33. Medzhitov et al., *Science* 296 (2002):298-300.
34. Gantner et al., *J. Exp. Med.* 197 (2003):1107-1117.
35. Huang et al., *Science.* 294 (2001):870-875.
36. Savolainen et al., *Allergy* 53 (1998):506-512.
37. Mari et al., *Clin. Exp. Allergy.* 33 (2003):1429-1438.
38. Kortekangas-Savolainen et al., *Clin Exp Allergy* 24 (1994):836-842.
39. Belchi-Hernandez et al., *Allergy Clin. Immunol.* 97 (1996):131-134.
40. Dentico et al., *Eur J Epidemiol.* 8 (1992):650-655.
41. Joossens et al., *Gastroenterology* 122 (2002):1242-7.
42. Sandborn et al., *Inflammatory Bowel Dis.* 7 (2001): 192-201.
43. Ponton et al., *Med. Mycology* 38 (2000):225-236.
44. Wheeler et al., *Proc Natl Acad Sci U S A.* 100 (2003): 2766-2770.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An HCV Core-E1-E2 fusion protein comprising HCV sequences, wherein the HCV sequences consist essentially of an HCV fusion protein comprising a full-length HCV Core protein fused to a full-length HCV E1 protein fused to a full-length HCV E2 protein, wherein the full-length HCV Core protein is linked at its N-terminus to the amino acid sequence represented by SEQ ID NO:9 (MADEAP).

2. The fusion protein of claim 1, wherein the fusion protein consists essentially of SEQ ID NO:12.

3. The fusion protein of claim 1, wherein the HCV fusion protein has been appended to include two amino acids, glutamate and aspartate.

4. The fusion protein of claim 1, wherein the HCV fusion protein has been appended to include the amino acid sequence of G-G-G-H-H-H-H-H-H (SEQ ID NO:10).

5. An isolated nucleic acid molecule comprising a nucleic acid sequence encoding the HCV Core-E1-E2 fusion protein of claim 1.

6. The isolated nucleic acid molecule of claim 5, wherein the expression of the fusion protein is under the control of an inducible promoter.

7. The isolated nucleic acid molecule of claim 6, wherein the inducible promoter is CUP1.

8. A recombinant nucleic acid molecule comprising the isolated nucleic acid molecule of claim 5.

9. A recombinant cell that has been transfected with the recombinant nucleic acid molecule of claim 8.

10. The recombinant cell of claim 9, wherein the cell is a yeast cell.

11. A composition comprising the nucleic acid molecule of claim 5.

12. A composition comprising the HCV Core-E1-E2 fusion protein of claim 1.

13. A composition comprising:
a) a yeast vehicle; and
b) the HCV Core-E1-E2 fusion protein of claim 1.

14. The composition of claim 13, wherein the HCV Core-E1-E2 fusion protein consists essentially of SEQ ID NO:14.

15. The composition of claim 13, wherein the expression of the fusion protein is under the control of an inducible promoter.

16. The composition of claim 13, wherein the composition further comprises a dendritic cell, wherein the dendritic cell has been loaded intracellularly with the yeast vehicle that recombinantly expresses the HCV Core-E1-E2 fusion protein.

17. The composition of claim 13, further comprising at least one biological response modifier.

18. A composition comprising:
a) a yeast vehicle; and
b) an HCV Core-E1-E2 fusion protein according to claim 2, wherein the HCV Core-E1-E2 fusion protein is under the control of the promoter CUP1;
wherein the HCV Core-E1-E2 fusion protein is expressed by the yeast vehicle.

19. An HCV Core-E1-E2 fusion protein comprising HCV sequences, wherein the HCV sequences consist essentially of a truncated HCV Core protein fused to an HCV E1 protein with deleted transmembrane domain and an HCV E2 protein with deleted transmembrane domain, wherein the truncated HCV Core protein is linked at its N-terminus to the amino acid sequence represented by SEQ ID NO:9 (MADEAP).

20. The fusion protein of claim 19, wherein the truncated HCV Core protein consists essentially of positions 2 to 140 of HCV Core protein (positions 2 to 140, with respect to SEQ ID NO:20).

21. The fusion protein of claim 19, wherein the HCV E1 protein with deleted transmembrane domain consists essentially of positions 1 to 156 of HCV E1 protein (positions 192 to 31, with respect to SEQ ID NO:20).

22. The fusion protein of claim 19, wherein the HCV E2 protein with deleted transmembrane domain consists essentially of positions 1 to 334 of HCV E2 protein (positions 384 to 717, with respect to SEQ ID NO:20).

23. The fusion protein of claim 19, wherein the fusion protein consists essentially of SEQ ID NO:14.

24. A composition comprising:
a) a yeast vehicle; and
b) an HCV Core-E1-E2 fusion protein according to claim 23, wherein the HCV Core-E1-E2 fusion protein is under the control of the promoter CUP1;
wherein the HCV Core-E1-E2 fusion protein is expressed by the yeast vehicle.

25. A composition comprising:
a) a yeast vehicle; and
b) the HCV Core-E1-E2 fusion protein of claim 19.

26. The composition of claim 25, wherein the fusion protein consists essentially of SEQ ID NO:14.

27. An HCV E1-E2 fusion protein comprising HCV sequences, wherein the HCV sequences consist of a an HCV E1 protein fused to an HCV E2 protein, wherein the HCV E1 protein is linked at its N-terminus to the amino acid sequence represented by SEQ ID NO:9 (MADEAP).

28. The HCV E1-E2 fusion protein of claim 27, wherein the fusion protein consists essentially of SEQ ID NO:6.

29. The fusion protein of claim 27, wherein the HCV fusion protein has been appended to include two amino acids, glutamate and aspartate.

30. The fusion protein of claim 27, wherein the HCV fusion protein has been appended to include the amino acid sequence of G-G-G-H-H-H-H-H-H (SEQ ID NO:10).

31. An isolated nucleic acid molecule comprising a nucleic acid sequence encoding the HCV E1-E2 fusion protein of claim 27.

32. The isolated nucleic acid molecule of claim 31, wherein the nucleic acid sequence is SEQ ID NO:5.

33. The isolated nucleic acid molecule of claim 31, wherein the expression of the fusion protein is under the control of an inducible promoter.

34. The isolated nucleic acid molecule of claim 32, wherein the inducible promoter is CUP1.

35. A recombinant nucleic acid molecule comprising the isolated nucleic acid molecule of claim 27.

36. A recombinant cell that has been transfected with the recombinant nucleic acid molecule of claim 35.

37. The recombinant cell of claim 36, wherein the cell is a yeast cell.

38. A composition comprising the HCV E1-E2 fusion protein of claim 27.

39. A composition comprising:
a) a yeast vehicle; and
b) the HCV E1-E2 fusion protein of claim 27.

40. The composition of claim 39, wherein the HCV E1-E2 fusion protein consists essentially of SEQ ID NO:6.

41. A composition comprising:
a) a yeast vehicle; and
b) an HCV E1-E2 fusion protein according to claim 28, wherein the HCV E1-E2 fusion protein is under the control of the promoter CUP1;
wherein the HCV E1-E2 fusion protein is expressed by the yeast vehicle.

42. The composition of claim 41, wherein the HCV E1-E2 fusion protein has been appended to include the amino acid sequence of G-G-G-H-H-H-H-H-H (SEQ ID NO:10).

* * * * *

SEQUENCE LISTING

<160> NUMBER OF SEQ ID NOS: 21

<210> SEQ ID NO 1
<211> LENGTH: 1233
<212> TYPE: DNA
<213> ORGANISM: Artificial
<220> FEATURE:
<223> OTHER INFORMATION: recombinant fusion protein construct

<400> SEQUENCE: 1

```
atggccgacg aggcaccaca aggttcccgc tcattgacac cctgtacctg cggctcctcg      60
gacctttacc tggtcacgag gcacgccgat gtcattcccg tgcgccggcg aggtgatagc     120
aggggtagcc tgctttcgcc ccggcccatt tcctacttga aggctcctc ggggggtccg      180
ctgttgtgcc ccgcgggaca cgccgtgggc ctattcaggg ccgcggtgtg cacccgtgga    240
gtggctaaag cggtggactt tatccctgtg gagaacctag gacaaccat gagatccccg     300
gtgttcacgg acaactcctc tccaccagca gtgccccaga gcttccaggt ggcccacctg    360
catgctccca ccggcagcgg taagagcacc aaggtcccgg ctgcgtacgc agcccagggc    420
tacaaggtgt tggtgctcaa ccctctgtt gctgcaacgc tgggctttgg tgcttacatg      480
tccaaggccc atggggttga tcctaatatc aggaccgggg tgagaacaat taccactggc    540
agccccatca cgtactccac ctacggcaag ttccttgccg acggcgggtg ctcaggaggt   600
gcttatgaca taataatttg tgacgagtgc cactccacgg atgccacatc catcttgggc    660
atcggcactg tccttgacca agcagagact gcggggggcga actggttgt gctcgccact    720
gctacccctc cgggctccgt cactgtgtcc catcctaaca tcgaggaggt tgctctgtcc    780
accaccggag agatcccctt ttacactagt acgaatccta aacctcaaag aaaaaccaaa    840
cgtaacacca accgtcgccc acaggacgtc aagttcccgg gtggcggtca atcgttggt     900
ggagtttact tgttgccgcg cagggggcct agattgggtg tgcgcgcgac gaggaagact    960
tccgagcggt cgcaacctcg aggtagacgt cagcctatcc ccaaggcacg tcggcccgag   1020
ggcaggacct gggctcagcc cgggtaccct tggcccctct atggcaatga gggttgcggg   1080
tgggcgggat ggctcctgtc tccccgtggc tctcggccta gctggggccc cacagacccc   1140
cggcgtaggt cgcgcaattt gggtaaggtc atcgataccc ttacgtgcgg cttcgccgac   1200
ctcatggggt acataccgct cgtcgaggac tag                                 1233
```

<210> SEQ ID NO 2
<211> LENGTH: 410
<212> TYPE: PRT
<213> ORGANISM: Artificial
<220> FEATURE:
<223> OTHER INFORMATION: recombinant fusion protein

<400> SEQUENCE: 2

Met Ala Asp Glu Ala Pro Gln Gly Ser Arg Ser Leu Thr Pro Cys Thr
 1               5                  10                  15

Cys Gly Ser Ser Asp Leu Tyr Leu Val Thr Arg His Ala Asp Val Ile
            20                  25                  30

Pro Val Arg Arg Arg Gly Asp Ser Arg Gly Ser Leu Leu Ser Pro Arg
        35                  40                  45

Pro Ile Ser Tyr Leu Lys Gly Ser Ser Gly Gly Pro Leu Leu Cys Pro
    50                  55                  60

```
Ala Gly His Ala Val Gly Leu Phe Arg Ala Ala Val Cys Thr Arg Gly
 65                  70                  75                  80

Val Ala Lys Ala Val Asp Phe Ile Pro Val Glu Asn Leu Gly Thr Thr
                 85                  90                  95

Met Arg Ser Pro Val Phe Thr Asp Asn Ser Ser Pro Ala Val Pro
            100                 105                 110

Gln Ser Phe Gln Val Ala His Leu His Ala Pro Thr Gly Ser Gly Lys
        115                 120                 125

Ser Thr Lys Val Pro Ala Ala Tyr Ala Ala Gln Gly Tyr Lys Val Leu
    130                 135                 140

Val Leu Asn Pro Ser Val Ala Ala Thr Leu Gly Phe Gly Ala Tyr Met
145                 150                 155                 160

Ser Lys Ala His Gly Val Asp Pro Asn Ile Arg Thr Gly Val Arg Thr
                165                 170                 175

Ile Thr Thr Gly Ser Pro Ile Thr Tyr Ser Thr Tyr Gly Lys Phe Leu
            180                 185                 190

Ala Asp Gly Gly Cys Ser Gly Gly Ala Tyr Asp Ile Ile Ile Cys Asp
        195                 200                 205

Glu Cys His Ser Thr Asp Ala Thr Ser Ile Leu Gly Ile Gly Thr Val
    210                 215                 220

Leu Asp Gln Ala Glu Thr Ala Gly Ala Arg Leu Val Val Leu Ala Thr
225                 230                 235                 240

Ala Thr Pro Pro Gly Ser Val Thr Val Ser His Pro Asn Ile Glu Glu
                245                 250                 255

Val Ala Leu Ser Thr Thr Gly Glu Ile Pro Phe Tyr Thr Ser Thr Asn
            260                 265                 270

Pro Lys Pro Gln Arg Lys Thr Lys Arg Asn Thr Asn Arg Arg Pro Gln
        275                 280                 285

Asp Val Lys Phe Pro Gly Gly Gly Gln Ile Val Gly Gly Val Tyr Leu
    290                 295                 300

Leu Pro Arg Arg Gly Pro Arg Leu Gly Val Arg Ala Thr Arg Lys Thr
305                 310                 315                 320

Ser Glu Arg Ser Gln Pro Arg Gly Arg Arg Gln Pro Ile Pro Lys Ala
                325                 330                 335

Arg Arg Pro Glu Gly Arg Thr Trp Ala Gln Pro Gly Tyr Pro Trp Pro
            340                 345                 350

Leu Tyr Gly Asn Glu Gly Cys Gly Trp Ala Gly Trp Leu Leu Ser Pro
        355                 360                 365

Arg Gly Ser Arg Pro Ser Trp Gly Pro Thr Asp Pro Arg Arg Arg Ser
    370                 375                 380

Arg Asn Leu Gly Lys Val Ile Asp Thr Leu Thr Cys Gly Phe Ala Asp
385                 390                 395                 400

Leu Met Gly Tyr Ile Pro Leu Val Glu Asp
                405                 410

<210> SEQ ID NO 3
<211> LENGTH: 1914
<212> TYPE: DNA
<213> ORGANISM: Artificial
<220> FEATURE:
<223> OTHER INFORMATION: recombinant fusion protein construct

<400> SEQUENCE: 3
atggccgacg aggcaccagc gcccatcacg gcgtacgccc agcagacgag aggcctccta      60
gggtgtataa tcaccagcct gactggccgg gacaaaaacc aagtggaggg tgaggtccag     120
```

-continued

```
atcgtgtcaa ctgctaccca aaccttcctg gcaacgtgca tcaatggggt atgctggact      180
gtctaccacg gggccggaac gaggaccatc gcatcaccca agggtcctgt catccagatg      240
tataccaatg tggaccaaga ccttgtgggc tggcccgctc ctcaaggttc ccgctcattg      300
acaccctgta cctgcggctc ctcggacctt tacctggtca cgaggcacgc cgatgtcatt      360
cccgtgcgcc ggcgaggtga tagcaggggt agcctgcttt cgccccggcc catttcctac      420
ttgaaaggct ccgctggggg tccgctgttg tgccccgcgg acacgccgt gggcctattc       480
agggccgcgg tgtgcacccg tggagtggct aaagcggtgg actttatccc tgtggagaac      540
ctagggacaa ccatgagatc cccggtgttc acggacaact cctctccacc agcagtgccc      600
cagagcttcc aggtggccca cctgcatgct cccaccggca cggtaagag caccaaggtc       660
ccggctgcgt acgcagccca gggctacaag gtgttggtgc tcaacccctc tgttgctgca      720
acgctgggct ttggtgctta catgtccaag gcccatgggg ttgatcctaa atcaggacc       780
ggggtgagaa caattaccac tggcagcccc atcacgtact ccacctacgg caagttcctt     840
gccgacggcg ggtgctcagg aggtgcttat gacataataa tttgtgacga gtgccactcc      900
acggatgcca catccatctt gggcatcggc actgtccttg accaagcaga gactgcgggg      960
gcgagactgg ttgtgctcgc cactgctacc cctccgggct ccgtcactgt gtcccatcct     1020
aacatcgagg aggttgctct gtccaccacc ggagagatcc ccttttacgg caaggctatc    1080
cccctcgagg tgatcaaggg gggaagacat ctcatcttct gccactcaaa gaagaagtgc    1140
gacgagctcg ccgcgaagct ggtcgcattg ggcatcaatg ccgtggccta ctaccgcggt    1200
cttgacgtgt ctgtcatccc gaccagcggc gatgttgtcg tcgtgtcgac cgatgctctc    1260
atgactggct ttaccggcga cttcgactct gtgatagact gcaacacgtg tgtcactcag    1320
acagtcgatt tcagccttga ccctaccttt accattgaga caaccacgct ccccaggat     1380
gctgtctcca ggactcaacg ccggggcagg actggcaggg ggaagccagg catctataga    1440
tttgtggcac cggggagcg ccctccggc atgttcgact cgtccgtcct ctgtgagtgc      1500
tatgacgcgg gctgtgcttg gtatgagctc acgcccgccg agactacagt taggctacga    1560
gcgtacatga acaccccggg gcttcccgtg tgccaggacc atcttgaatt tgggagggc     1620
gtctttacgg gcctcactca tatagatgcc cactttttat cccagacaaa gcagagtggg    1680
gagaactttc cttacctggt agcgtaccaa gccaccgtgt gcgctagggc tcaagcccct    1740
cccccatcgt gggaccagat gtggaagtgt ttgatccgcc ttaaacccac cctccatggg    1800
ccaacacccc tgctatacag actgggcgct gttcagaatg aagtcaccct gacgcaccca    1860
atcaccaaat acatcatgac atgcatgtcg gccgacctgg aggtcgtcac gtag          1914
```

<210> SEQ ID NO 4
<211> LENGTH: 637
<212> TYPE: PRT
<213> ORGANISM: Artificial
<220> FEATURE:
<223> OTHER INFORMATION: recombinant fusion protein

<400> SEQUENCE: 4

Met Ala Asp Glu Ala Pro Ala Pro Ile Thr Ala Tyr Ala Gln Gln Thr
1               5                   10                  15

Arg Gly Leu Leu Gly Cys Ile Ile Thr Ser Leu Thr Gly Arg Asp Lys
                20                  25                  30

Asn Gln Val Glu Gly Glu Val Gln Ile Val Ser Thr Ala Thr Gln Thr
            35                  40                  45

-continued

```
Phe Leu Ala Thr Cys Ile Asn Gly Val Cys Trp Thr Val Tyr His Gly
 50                  55                  60

Ala Gly Thr Arg Thr Ile Ala Ser Pro Lys Gly Pro Val Ile Gln Met
 65                  70                  75                  80

Tyr Thr Asn Val Asp Gln Asp Leu Val Gly Trp Pro Ala Pro Gln Gly
                 85                  90                  95

Ser Arg Ser Leu Thr Pro Cys Thr Cys Gly Ser Ser Asp Leu Tyr Leu
            100                 105                 110

Val Thr Arg His Ala Asp Val Ile Pro Val Arg Arg Gly Asp Ser
        115                 120                 125

Arg Gly Ser Leu Leu Ser Pro Arg Pro Ile Ser Tyr Leu Lys Gly Ser
130                 135                 140

Ala Gly Gly Pro Leu Leu Cys Pro Ala Gly His Ala Val Gly Leu Phe
145                 150                 155                 160

Arg Ala Ala Val Cys Thr Arg Gly Val Ala Lys Ala Val Asp Phe Ile
                165                 170                 175

Pro Val Glu Asn Leu Gly Thr Thr Met Arg Ser Pro Val Phe Thr Asp
            180                 185                 190

Asn Ser Ser Pro Pro Ala Val Pro Gln Ser Phe Gln Val Ala His Leu
        195                 200                 205

His Ala Pro Thr Gly Ser Gly Lys Ser Thr Lys Val Pro Ala Ala Tyr
    210                 215                 220

Ala Ala Gln Gly Tyr Lys Val Leu Val Leu Asn Pro Ser Val Ala Ala
225                 230                 235                 240

Thr Leu Gly Phe Gly Ala Tyr Met Ser Lys Ala His Gly Val Asp Pro
                245                 250                 255

Asn Ile Arg Thr Gly Val Arg Thr Ile Thr Thr Gly Ser Pro Ile Thr
            260                 265                 270

Tyr Ser Thr Tyr Gly Lys Phe Leu Ala Asp Gly Gly Cys Ser Gly Gly
        275                 280                 285

Ala Tyr Asp Ile Ile Ile Cys Asp Glu Cys His Ser Thr Asp Ala Thr
    290                 295                 300

Ser Ile Leu Gly Ile Gly Thr Val Leu Asp Gln Ala Glu Thr Ala Gly
305                 310                 315                 320

Ala Arg Leu Val Val Leu Ala Thr Ala Thr Pro Pro Gly Ser Val Thr
                325                 330                 335

Val Ser His Pro Asn Ile Glu Glu Val Ala Leu Ser Thr Thr Gly Glu
            340                 345                 350

Ile Pro Phe Tyr Gly Lys Ala Ile Pro Leu Glu Val Ile Lys Gly Gly
        355                 360                 365

Arg His Leu Ile Phe Cys His Ser Lys Lys Lys Cys Asp Glu Leu Ala
    370                 375                 380

Ala Lys Leu Val Ala Leu Gly Ile Asn Ala Val Ala Tyr Tyr Arg Gly
385                 390                 395                 400

Leu Asp Val Ser Val Ile Pro Thr Ser Gly Asp Val Val Val Ser
                405                 410                 415

Thr Asp Ala Leu Met Thr Gly Phe Thr Gly Asp Phe Asp Ser Val Ile
            420                 425                 430

Asp Cys Asn Thr Cys Val Thr Gln Thr Val Asp Phe Ser Leu Asp Pro
        435                 440                 445

Thr Phe Thr Ile Glu Thr Thr Thr Leu Pro Gln Asp Ala Val Ser Arg
    450                 455                 460
```

```
Thr Gln Arg Arg Gly Arg Thr Gly Arg Gly Lys Pro Gly Ile Tyr Arg
465                 470                 475                 480

Phe Val Ala Pro Gly Glu Arg Pro Ser Gly Met Phe Asp Ser Ser Val
                485                 490                 495

Leu Cys Glu Cys Tyr Asp Ala Gly Cys Ala Trp Tyr Glu Leu Thr Pro
            500                 505                 510

Ala Glu Thr Thr Val Arg Leu Arg Ala Tyr Met Asn Thr Pro Gly Leu
        515                 520                 525

Pro Val Cys Gln Asp His Leu Glu Phe Trp Glu Gly Val Phe Thr Gly
    530                 535                 540

Leu Thr His Ile Asp Ala His Phe Leu Ser Gln Thr Lys Gln Ser Gly
545                 550                 555                 560

Glu Asn Phe Pro Tyr Leu Val Ala Tyr Gln Ala Thr Val Cys Ala Arg
                565                 570                 575

Ala Gln Ala Pro Pro Pro Ser Trp Asp Gln Met Trp Lys Cys Leu Ile
            580                 585                 590

Arg Leu Lys Pro Thr Leu His Gly Pro Thr Pro Leu Leu Tyr Arg Leu
        595                 600                 605

Gly Ala Val Gln Asn Glu Val Thr Leu Thr His Pro Ile Thr Lys Tyr
    610                 615                 620

Ile Met Thr Cys Met Ser Ala Asp Leu Glu Val Val Thr
625                 630                 635

<210> SEQ ID NO 5
<211> LENGTH: 1491
<212> TYPE: DNA
<213> ORGANISM: Artificial
<220> FEATURE:
<223> OTHER INFORMATION: recombinant fusion protein construct

<400> SEQUENCE: 5
atggccgacg aggcaccata ccaagtgcgc aattcctcgg ggctttacca tgtcaccaat      60
gattgcccta actcgagtat tgtgtacgag gcggccgatg ccatcctgca cactccgggg     120
tgtgtccctt gcgttcgcga gggtaacgcc tcgaggtgtt gggtggcggt gaccccacg     180 gtggccacca gggacggcaa actccccaca acgcagcttc gacgtcatat cgatctgctt     240
gtcgggagcg ccaccctctg ctcggccctc tacgtggggg acctgtgcgg gtctgtcttt     300
cttgttggtc aactgttta cttctctccc aggcgccact ggacgacgca agactgcaat     360
tgttctatct atcccggcca tataacgggt catcgcatgg catgggatat gatgatgaac     420
tggtccccta cggcagcgtt ggtggtagct cagctgctcc ggatcccaca agccatcatg     480
gacatggaaa cccacgtcac cgggggaagt gccggccgca ccacggctgg gcttgttggt     540
ctccttacac caggcgccaa gcagaacatc caactgatca acaccaacgg cagttggcac     600
atcaatagca cggccttgaa ctgcaatgaa agccttaaca ccggctggtt agcagggctc     660
ttctatcagc acaaattcaa ctcttcaggc tgtcctgaga ggttggccag ctgccgacgc     720
cttaccgatt tgcccagggg ctgggtcct atcagttatg ccaacggaag cggcctcgac     780
gaacgcccct actgctggca ctaccctcca agaccttgtg gcattgtgcc cgcaaagagc     840
gtgtgtggcc cggtatattg cttcactccc agccccgtgg tggtgggaac gaccgacagg     900
tcgggcgcgc ctacctacag ctgggggtgca aatgatacgg atgtcttcgt ccttaacaac     960
accaggccac cgctgggcaa ttggttcggt tgtacctgga tgaactcaac tggattcacc    1020
aaagtgtgcg gagcgccccc ttgtgtcatc ggagggggtgg gcaacaacac cttgctctgc    1080
```

```
cccactgatt gtttccgcaa gcatccggaa gccacatact ctcggtgcgg ctccggtccc   1140
tggattacac ccaggtgcat ggtcgactac ccgtataggc tttggcacta tccttgtacc   1200
atcaattaca ccatattcaa agtcaggatg tacgtgggag gggtcgagca caggctggaa   1260
gcggcctgca actggacgcg gggcgaacgc tgtgatctgg aagacaggga caggtccgag   1320
ctcagcccat tgctgctgtc caccacacag tggcaggtcc ttccgtgttc tttcacgacc   1380
ctgccagcct tgtccaccgg cctcatccac ctccaccaga acattgtgga cgtgcagtac   1440
ttgtacgggg tagggtcaag catcgcgtcc tgggccatta agtgggagta g            1491
```

<210> SEQ ID NO 6
<211> LENGTH: 496
<212> TYPE: PRT
<213> ORGANISM: Artificial
<220> FEATURE:
<223> OTHER INFORMATION: recombinant fusion protein

<400> SEQUENCE: 6

```
Met Ala Asp Glu Ala Pro Tyr Gln Val Arg Asn Ser Ser Gly Leu Tyr
1               5                   10                  15

His Val Thr Asn Asp Cys Pro Asn Ser Ser Ile Val Tyr Glu Ala Ala
            20                  25                  30

Asp Ala Ile Leu His Thr Pro Gly Cys Val Pro Cys Val Arg Glu Gly
        35                  40                  45

Asn Ala Ser Arg Cys Trp Val Ala Val Thr Pro Thr Val Ala Thr Arg
    50                  55                  60

Asp Gly Lys Leu Pro Thr Thr Gln Leu Arg Arg His Ile Asp Leu Leu
65                  70                  75                  80

Val Gly Ser Ala Thr Leu Cys Ser Ala Leu Tyr Val Gly Asp Leu Cys
                85                  90                  95

Gly Ser Val Phe Leu Val Gly Gln Leu Phe Thr Phe Ser Pro Arg Arg
            100                 105                 110

His Trp Thr Thr Gln Asp Cys Asn Cys Ser Ile Tyr Pro Gly His Ile
        115                 120                 125

Thr Gly His Arg Met Ala Trp Asp Met Met Met Asn Trp Ser Pro Thr
    130                 135                 140

Ala Ala Leu Val Val Ala Gln Leu Leu Arg Ile Pro Gln Ala Ile Met
145                 150                 155                 160

Asp Met Glu Thr His Val Thr Gly Gly Ser Ala Gly Arg Thr Thr Ala
                165                 170                 175

Gly Leu Val Gly Leu Leu Thr Pro Gly Ala Lys Gln Asn Ile Gln Leu
            180                 185                 190

Ile Asn Thr Asn Gly Ser Trp His Ile Asn Ser Thr Ala Leu Asn Cys
        195                 200                 205

Asn Glu Ser Leu Asn Thr Gly Trp Leu Ala Gly Leu Phe Tyr Gln His
    210                 215                 220

Lys Phe Asn Ser Ser Gly Cys Pro Glu Arg Leu Ala Ser Cys Arg Arg
225                 230                 235                 240

Leu Thr Asp Phe Ala Gln Gly Trp Gly Pro Ile Ser Tyr Ala Asn Gly
                245                 250                 255

Ser Gly Leu Asp Glu Arg Pro Tyr Cys Trp His Tyr Pro Pro Arg Pro
            260                 265                 270

Cys Gly Ile Val Pro Ala Lys Ser Val Cys Gly Pro Val Tyr Cys Phe
        275                 280                 285

Thr Pro Ser Pro Val Val Val Gly Thr Thr Asp Arg Ser Gly Ala Pro
```

```
              290                 295                 300
Thr Tyr Ser Trp Gly Ala Asn Asp Thr Asp Val Phe Val Leu Asn Asn
305                 310                 315                 320

Thr Arg Pro Pro Leu Gly Asn Trp Phe Gly Cys Thr Trp Met Asn Ser
                325                 330                 335

Thr Gly Phe Thr Lys Val Cys Gly Ala Pro Pro Cys Val Ile Gly Gly
            340                 345                 350

Val Gly Asn Asn Thr Leu Leu Cys Pro Thr Asp Cys Phe Arg Lys His
        355                 360                 365

Pro Glu Ala Thr Tyr Ser Arg Cys Gly Ser Gly Pro Trp Ile Thr Pro
370                 375                 380

Arg Cys Met Val Asp Tyr Pro Tyr Arg Leu Trp His Tyr Pro Cys Thr
385                 390                 395                 400

Ile Asn Tyr Thr Ile Phe Lys Val Arg Met Tyr Val Gly Gly Val Glu
                405                 410                 415

His Arg Leu Glu Ala Ala Cys Asn Trp Thr Arg Gly Glu Arg Cys Asp
            420                 425                 430

Leu Glu Asp Arg Asp Arg Ser Glu Leu Ser Pro Leu Leu Leu Ser Thr
435                 440                 445

Thr Gln Trp Gln Val Leu Pro Cys Ser Phe Thr Thr Leu Pro Ala Leu
    450                 455                 460

Ser Thr Gly Leu Ile His Leu His Gln Asn Ile Val Asp Val Gln Tyr
465                 470                 475                 480

Leu Tyr Gly Val Gly Ser Ser Ile Ala Ser Trp Ala Ile Lys Trp Glu
                485                 490                 495

<210> SEQ ID NO 7
<211> LENGTH: 483
<212> TYPE: DNA
<213> ORGANISM: Artificial
<220> FEATURE:
<223> OTHER INFORMATION: recombinant fusion protein construct

<400> SEQUENCE: 7
atggccgacg aggcaccatc tcagcactta ccgtacatcg agcaagggat gatgctcgct      60
gagcagttca gcagaaggc cctcggcctc ctgcagaccg cgtcccgcca tgcagaggtt     120
atcacccctg ctgtccagac caactggcag aaactcgagg tcttctgggc gaagcacatg     180
tggaatttca tcagtgggat acaatacttg gcgggcctgt caactagtcc tggagccctt     240
gtagtcggtg tggtctgcgc agcaaactg cgccggcacg ttggcccggg cgaggggca     300 gtgcaatgga tgaaccggct aatagccttc gcctcccggg ggaaccatgt ttcccccacg     360
cactacgtgc cggagagcga tgcagccgcc gcgtcactg ccatactcag cagcctcact     420
gtaacccagc tcctgaggcg actgcatcag tggataagct cggagtgtac cactccatgc     480
tag                                                                   483

<210> SEQ ID NO 8
<211> LENGTH: 160
<212> TYPE: PRT
<213> ORGANISM: Artificial
<220> FEATURE:
<223> OTHER INFORMATION: recombinant fusion protein

<400> SEQUENCE: 8

Met Ala Asp Glu Ala Pro Ser Gln His Leu Pro Tyr Ile Glu Gln Gly
1               5                   10                  15
```

-continued

```
Met Met Leu Ala Glu Gln Phe Lys Gln Lys Ala Leu Gly Leu Leu Gln
         20                  25                  30

Thr Ala Ser Arg His Ala Glu Val Ile Thr Pro Ala Val Gln Thr Asn
             35                  40                  45

Trp Gln Lys Leu Glu Val Phe Trp Ala Lys His Met Trp Asn Phe Ile
 50                  55                  60

Ser Gly Ile Gln Tyr Leu Ala Gly Leu Ser Thr Ser Pro Gly Ala Leu
 65                  70                  75                  80

Val Val Gly Val Val Cys Ala Ala Ile Leu Arg Arg His Val Gly Pro
                 85                  90                  95

Gly Glu Gly Ala Val Gln Trp Met Asn Arg Leu Ile Ala Phe Ala Ser
            100                 105                 110

Arg Gly Asn His Val Ser Pro Thr His Tyr Val Pro Glu Ser Asp Ala
        115                 120                 125

Ala Ala Arg Val Thr Ala Ile Leu Ser Ser Leu Thr Val Thr Gln Leu
    130                 135                 140

Leu Arg Arg Leu His Gln Trp Ile Ser Ser Glu Cys Thr Thr Pro Cys
145                 150                 155                 160

<210> SEQ ID NO 9
<211> LENGTH: 6
<212> TYPE: PRT
<213> ORGANISM: Artificial
<220> FEATURE:
<223> OTHER INFORMATION: synthetic peptide

<400> SEQUENCE: 9

Met Ala Asp Glu Ala Pro
1               5

<210> SEQ ID NO 10
<211> LENGTH: 9
<212> TYPE: PRT
<213> ORGANISM: Artificial
<220> FEATURE:
<223> OTHER INFORMATION: synthetic peptide

<400> SEQUENCE: 10

Gly Gly Gly His His His His His His
1               5

<210> SEQ ID NO 11
<211> LENGTH: 2256
<212> TYPE: DNA
<213> ORGANISM: Artificial
<220> FEATURE:
<223> OTHER INFORMATION: recombinant fusion protein construct

<400> SEQUENCE: 11
atggccgacg aggcaccaag cacgaatcct aaacctcaaa gaaaaaccaa acgtaacacc      60
aaccgtcgcc cacaggacgt caagttcccg ggtggcggtc agatcgttgg tggagtttac     120
ttgttgccgc gcaggggccc tagattgggt gtgcgcgcga cgaggaagac ttccgagcgg     180
tcgcaaccct cgaggtagacg tcagcctatc cccaaggcac gtcggcccga gggcaggacc     240
tgggctcagc ccgggtaccc ttggccccte tatggcaatg agggttgcgg gtgggcggga     300
tggctcctgt ctcccgtgg ctctcggcct agctggggcc ccacagaccc ccggcgtagg      360
tcgcgcaatt tgggtaaggt catcgatacc cttacgtgcg gcttcgccga cctcatgggg     420
tacataccgc tcgtcggcgc ccctcttgga ggcgctgcca gggcccctgg cgcatggcgtc    480
```

-continued

```
cgggttctgg aagacggcgt gaactatgca acagggaacc ttcctggttg ctctttctct      540
atcttccttc tggccctgct ctcttgcctg actgtgcccg cttcagccta ccaagtgcgc      600
aattcctcgg ggctttacca tgtcaccaat gattgcccta actgagtat tgtgtacgag       660
gcggccgatg ccatcctgca cactccgggg tgtgtccctt gcgttcgcga gggtaacgcc      720
tcgaggtgtt gggtggcggt gaccccacg gtggccacca gggacggcaa actccccaca       780
acgcagcttc gacgtcatat cgatctgctt gtcgggagcg ccaccctctg ctcggccctc      840
tacgtggggg acctgtgcgg gtctgtcttt cttgttggtc aactgtttac cttctctccc      900
aggcgccact ggacgacgca agactgcaat tgttctatct atcccggcca tataacgggt      960
catcgcatgg catgggatat gatgatgaac tggtcccta cggcagcgtt ggtggtagct      1020
cagctgctcc ggatcccaca agccatcatg gacatgatcg ctggtgctca ctggggagtc     1080
ctggcgggca tagcgtattt ctccatggtg gggaactggg cgaaggtcct ggtagtgctg     1140
ctgctatttg ccggcgtcga cgcggaaacc cacgtcaccg ggggaagtgc cggccgcacc     1200
acggctgggc ttgttggtct ccttacacca ggcgccaagc agaacatcca actgatcaac     1260
accaacggca gttggcacat caatagcacg gccttgaact gcaatgaaag ccttaacacc     1320
ggctggttag cagggctctt ctatcagcac aaattcaact cttcaggctg tcctgagagg     1380
ttggccagct gccgacgcct taccgatttt gcccagggcg ggggtcctat cagttatgcc     1440
aacggaagcg gcctcgacga acgcccctac tgctggcact accctccaag accttgtggc     1500
attgtgcccg caaagagcgt gtgtggcccg gtatattgct tcactcccag ccccgtggtg     1560
gtgggaacga ccgacaggtc gggcgcgcct acctacagct ggggtgcaaa tgatacggat     1620
gtcttcgtcc ttaacaacac caggccaccg ctgggcaatt ggttcggttg tacctggatg     1680
aactcaactg gattcaccaa agtgtgcgga gcgcccctt gtgtcatcgg aggggtgggc     1740
aacaacacct tgctctgccc cactgattgt ttccgcaagc atccggaagc cacatactct     1800
cggtgcggct ccggtccctg gattacaccc aggtgcatgg tcgactaccc gtataggctt     1860
tggcactatc cttgtaccat caattacacc atattcaaag tcaggatgta cgtgggaggg     1920
gtcgagcaca ggctggaagc ggcctgcaac tggacgcggg gcgaacgctg tgatctggaa     1980
gacagggaca ggtccgagct cagcccattg ctgctgtcca ccacagtg gcaggtcctt      2040
ccgtgttctt tcacgaccct gccagccttg tccaccggcc tcatccacct ccaccagaac     2100
attgtggacg tgcagtactt gtacgggta gggtcaagca tcgcgtcctg gccattaag      2160
tgggagtacg tcgttctcct gttcctcctg cttgcagacg cgcgcgtctg ctcctgcttg     2220
tggatgatgt tactcatatc ccaagcggag gcgtag                               2256
```

<210> SEQ ID NO 12
<211> LENGTH: 751
<212> TYPE: PRT
<213> ORGANISM: Artificial
<220> FEATURE:
<223> OTHER INFORMATION: recombinant fusion protein

<400> SEQUENCE: 12

```
Met Ala Asp Glu Ala Pro Ser Thr Asn Pro Lys Pro Gln Arg Lys Thr
1               5                   10                  15

Lys Arg Asn Thr Asn Arg Arg Pro Gln Asp Val Lys Phe Pro Gly Gly
            20                  25                  30

Gly Gln Ile Val Gly Gly Val Tyr Leu Leu Pro Arg Arg Gly Pro Arg
        35                  40                  45
```

-continued

```
Leu Gly Val Arg Ala Thr Arg Lys Thr Ser Glu Arg Ser Gln Pro Arg
 50                  55                  60

Gly Arg Arg Gln Pro Ile Pro Lys Ala Arg Arg Pro Glu Gly Arg Thr
 65                  70                  75                  80

Trp Ala Gln Pro Gly Tyr Pro Trp Pro Leu Tyr Gly Asn Glu Gly Cys
                     85                  90                  95

Gly Trp Ala Gly Trp Leu Leu Ser Pro Arg Gly Ser Arg Pro Ser Trp
                100                 105                 110

Gly Pro Thr Asp Pro Arg Arg Arg Ser Arg Asn Leu Gly Lys Val Ile
                115                 120                 125

Asp Thr Leu Thr Cys Gly Phe Ala Asp Leu Met Gly Tyr Ile Pro Leu
130                 135                 140

Val Gly Ala Pro Leu Gly Gly Ala Ala Arg Ala Leu Ala His Gly Val
145                 150                 155                 160

Arg Val Leu Glu Asp Gly Val Asn Tyr Ala Thr Gly Asn Leu Pro Gly
                165                 170                 175

Cys Ser Phe Ser Ile Phe Leu Leu Ala Leu Leu Ser Cys Leu Thr Val
                180                 185                 190

Pro Ala Ser Ala Tyr Gln Val Arg Asn Ser Ser Gly Leu Tyr His Val
                195                 200                 205

Thr Asn Asp Cys Pro Asn Ser Ser Ile Val Tyr Glu Ala Ala Asp Ala
210                 215                 220

Ile Leu His Thr Pro Gly Cys Val Pro Cys Val Arg Glu Gly Asn Ala
225                 230                 235                 240

Ser Arg Cys Trp Val Ala Val Thr Pro Thr Val Ala Thr Arg Asp Gly
                245                 250                 255

Lys Leu Pro Thr Thr Gln Leu Arg Arg His Ile Asp Leu Leu Val Gly
                260                 265                 270

Ser Ala Thr Leu Cys Ser Ala Leu Tyr Val Gly Asp Leu Cys Gly Ser
                275                 280                 285

Val Phe Leu Val Gly Gln Leu Phe Thr Phe Ser Pro Arg Arg His Trp
290                 295                 300

Thr Thr Gln Asp Cys Asn Cys Ser Ile Tyr Pro Gly His Ile Thr Gly
305                 310                 315                 320

His Arg Met Ala Trp Asp Met Met Met Asn Trp Ser Pro Thr Ala Ala
                325                 330                 335

Leu Val Val Ala Gln Leu Leu Arg Ile Pro Gln Ala Ile Met Asp Met
                340                 345                 350

Ile Ala Gly Ala His Trp Gly Val Leu Ala Gly Ile Ala Tyr Phe Ser
                355                 360                 365

Met Val Gly Asn Trp Ala Lys Val Leu Val Val Leu Leu Leu Phe Ala
370                 375                 380

Gly Val Asp Ala Glu Thr His Val Thr Gly Gly Ser Ala Gly Arg Thr
385                 390                 395                 400

Thr Ala Gly Leu Val Gly Leu Leu Thr Pro Gly Ala Lys Gln Asn Ile
                405                 410                 415

Gln Leu Ile Asn Thr Asn Gly Ser Trp His Ile Asn Ser Thr Ala Leu
                420                 425                 430

Asn Cys Asn Glu Ser Leu Asn Thr Gly Trp Leu Ala Gly Leu Phe Tyr
                435                 440                 445

Gln His Lys Phe Asn Ser Ser Gly Cys Pro Glu Arg Leu Ala Ser Cys
450                 455                 460

Arg Arg Leu Thr Asp Phe Ala Gln Gly Trp Gly Pro Ile Ser Tyr Ala
```

-continued

```
                465                 470                 475                 480
Asn Gly Ser Gly Leu Asp Glu Arg Pro Tyr Cys Trp His Tyr Pro Pro
                    485                 490                 495
Arg Pro Cys Gly Ile Val Pro Ala Lys Ser Val Cys Gly Pro Val Tyr
                500                 505                 510
Cys Phe Thr Pro Ser Pro Val Val Gly Thr Thr Asp Arg Ser Gly
            515                 520                 525
Ala Pro Thr Tyr Ser Trp Gly Ala Asn Asp Thr Asp Val Phe Val Leu
        530                 535                 540
Asn Asn Thr Arg Pro Pro Leu Gly Asn Trp Phe Gly Cys Thr Trp Met
545                 550                 555                 560
Asn Ser Thr Gly Phe Thr Lys Val Cys Gly Ala Pro Pro Cys Val Ile
                565                 570                 575
Gly Gly Val Gly Asn Asn Thr Leu Leu Cys Pro Thr Asp Cys Phe Arg
                580                 585                 590
Lys His Pro Glu Ala Thr Tyr Ser Arg Cys Gly Ser Gly Pro Trp Ile
            595                 600                 605
Thr Pro Arg Cys Met Val Asp Tyr Pro Tyr Arg Leu Trp His Tyr Pro
        610                 615                 620
Cys Thr Ile Asn Tyr Thr Ile Phe Lys Val Arg Met Tyr Val Gly Gly
625                 630                 635                 640
Val Glu His Arg Leu Glu Ala Ala Cys Asn Trp Thr Arg Gly Glu Arg
                645                 650                 655
Cys Asp Leu Glu Asp Arg Asp Arg Ser Glu Leu Ser Pro Leu Leu Leu
                660                 665                 670
Ser Thr Thr Gln Trp Gln Val Leu Pro Cys Ser Phe Thr Thr Leu Pro
            675                 680                 685
Ala Leu Ser Thr Gly Leu Ile His Leu His Gln Asn Ile Val Asp Val
        690                 695                 700
Gln Tyr Leu Tyr Gly Val Gly Ser Ser Ile Ala Ser Trp Ala Ile Lys
705                 710                 715                 720
Trp Glu Tyr Val Val Leu Leu Phe Leu Leu Leu Ala Asp Ala Arg Val
                725                 730                 735
Cys Ser Cys Leu Trp Met Met Leu Leu Ile Ser Gln Ala Glu Ala
                740                 745                 750
```

<210> SEQ ID NO 13
<211> LENGTH: 1908
<212> TYPE: DNA
<213> ORGANISM: Artificial
<220> FEATURE:
<223> OTHER INFORMATION: recombinant fusion protein construct

<400> SEQUENCE: 13

```
atggccgacg aggcaccaag tacgaatcct aaacctcaaa gaaaaccaa acgtaacacc      60
aaccgtcgcc cacaggacgt caagttcccg ggtggcggtc agatcgttgg tgagtttac    120
ttgttgccgc gcaggggccc tagattgggt gtgcgcgcga cgaggaagac ttccgagcgg    180
tcgcaacctc gaggtagacg tcagcctatc cccaaggcac gtcggcccga gggcaggacc    240
tgggctcagc ccgggtaccc ttggcccctc tatggcaatg agggttgcgg gtgggcggga    300
tggctcctgt ctccccgtgg ctctcggcct agctggggcc ccacagaccc ccggcgtagg    360
tcgcgcaatt tgggtaaggt catcgatacc cttacgtgcg gcttcgccga cctcatgggg    420
tacataccgc tcgtctacca agtgcgcaat tcctcggggc tttaccatgt caccaatgat    480
```

```
tgccctaact cgagtattgt gtacgaggcg gccgatgcca tcctgcacac tccggggtgt    540
gtcccttgcg ttcgcgaggg taacgcctcg aggtgttggg tggcggtgac ccccacggtg    600
gccaccaggg acggcaaact ccccacaacg cagcttcgac gtcatatcga tctgcttgtc    660
gggagcgcca ccctctgctc ggccctctac gtgggggacc tgtgcgggtc tgtctttctt    720
gttggtcaac tgtttacctt ctctcccagg cgccactgga cgacgcaaga ctgcaattgt    780
tctatctatc ccggccatat aacgggtcat cgcatggcat gggatatgat gatgaactgg    840 tccctacgg cagcgttggt ggtagctcag ctgctccgga tcccacaagc catcatggac     900
atggaaaccc acgtcaccgg gggaagtgcc ggccgcacca cggctgggct tgttggtctc    960
cttacaccag gcgccaagca gaacatccaa ctgatcaaca ccaacggcag ttggcacatc   1020
aatagcacgg ccttgaactg caatgaaagc cttaacaccg ctggttagc agggctcttc    1080 tatcagcaca aattcaactc ttcaggctgt cctgagaggt tggccagctg ccgacgcctt   1140
accgattttg cccagggctg gggtcctatc agttatgcca acggaagcgg cctcgacgaa   1200
cgcccctact gctggcacta ccctccaaga ccttgtggca ttgtgcccgc aaagagcgtg   1260
tgtggcccgg tatattgctt cactcccagc cccgtggtgg tgggaacgac cgacaggtcg   1320
ggcgcgccta cctacagctg gggtgcaaat gatacggatg tcttcgtcct aacaacacc    1380 aggccaccgc tggcaattg gttcggttgt acctggatga actcaactgg attcaccaaa    1440
gtgtgcggag cgccccttg tgtcatcgga ggggtgggca acaacacctt gctctgcccc    1500
actgattgtt ccgcaagca tccggaagcc acatactctc ggtgcggctc cggtccctgg   1560
attacaccca ggtgcatggt cgactacccg tataggcttt ggcactatcc ttgtaccatc   1620
aattaccaca tattcaaagt caggatgtac gtgggagggg tcgagcacag gctggaagcg   1680
gcctgcaact ggacgcgggg cgaacgctgt gatctggaag acagggacag gtccgagctc   1740
agcccattgc tgctgtccac cacacagtgg caggtccttc cgtgttcttt cacgaccctg   1800
ccagccttgt ccaccggcct catccacctc caccagaaca ttgtggacgt gcagtacttg   1860
tacggggtag ggtcaagcat cgcgtcctgg gccattaagt gggagtag             1908
```

<210> SEQ ID NO 14
<211> LENGTH: 635
<212> TYPE: PRT
<213> ORGANISM: Artificial
<220> FEATURE:
<223> OTHER INFORMATION: recombinant fusion protein

<400> SEQUENCE: 14

```
Met Ala Asp Glu Ala Pro Ser Thr Asn Pro Lys Pro Gln Arg Lys Thr
1               5                  10                  15

Lys Arg Asn Thr Asn Arg Arg Pro Gln Asp Val Lys Phe Pro Gly Gly
            20                  25                  30

Gly Gln Ile Val Gly Gly Val Tyr Leu Leu Pro Arg Arg Gly Pro Arg
        35                  40                  45

Leu Gly Val Arg Ala Thr Arg Lys Thr Ser Glu Arg Ser Gln Pro Arg
    50                  55                  60

Gly Arg Arg Gln Pro Ile Pro Lys Ala Arg Arg Pro Glu Gly Arg Thr
65                  70                  75                  80

Trp Ala Gln Pro Gly Tyr Pro Trp Pro Leu Tyr Gly Asn Glu Gly Cys
                85                  90                  95

Gly Trp Ala Gly Trp Leu Leu Ser Pro Arg Gly Ser Arg Pro Ser Trp
            100                 105                 110
```

-continued

```
Gly Pro Thr Asp Pro Arg Arg Arg Ser Arg Asn Leu Gly Lys Val Ile
        115                 120                 125

Asp Thr Leu Thr Cys Gly Phe Ala Asp Leu Met Gly Tyr Ile Pro Leu
    130                 135                 140

Val Tyr Gln Val Arg Asn Ser Ser Gly Leu Tyr His Val Thr Asn Asp
145                 150                 155                 160

Cys Pro Asn Ser Ser Ile Val Tyr Glu Ala Ala Asp Ala Ile Leu His
                165                 170                 175

Thr Pro Gly Cys Val Pro Cys Val Arg Glu Gly Asn Ala Ser Arg Cys
            180                 185                 190

Trp Val Ala Val Thr Pro Thr Val Ala Thr Arg Asp Gly Lys Leu Pro
        195                 200                 205

Thr Thr Gln Leu Arg Arg His Ile Asp Leu Leu Val Gly Ser Ala Thr
    210                 215                 220

Leu Cys Ser Ala Leu Tyr Val Gly Asp Leu Cys Gly Ser Val Phe Leu
225                 230                 235                 240

Val Gly Gln Leu Phe Thr Phe Ser Pro Arg Arg His Trp Thr Thr Gln
                245                 250                 255

Asp Cys Asn Cys Ser Ile Tyr Pro Gly His Ile Thr Gly His Arg Met
            260                 265                 270

Ala Trp Asp Met Met Met Asn Trp Ser Pro Thr Ala Ala Leu Val Val
        275                 280                 285

Ala Gln Leu Leu Arg Ile Pro Gln Ala Ile Met Asp Met Glu Thr His
    290                 295                 300

Val Thr Gly Gly Ser Ala Gly Arg Thr Thr Ala Gly Leu Val Gly Leu
305                 310                 315                 320

Leu Thr Pro Gly Ala Lys Gln Asn Ile Gln Leu Ile Asn Thr Asn Gly
                325                 330                 335

Ser Trp His Ile Asn Ser Thr Ala Leu Asn Cys Asn Glu Ser Leu Asn
            340                 345                 350

Thr Gly Trp Leu Ala Gly Leu Phe Tyr Gln His Lys Phe Asn Ser Ser
        355                 360                 365

Gly Cys Pro Glu Arg Leu Ala Ser Cys Arg Arg Leu Thr Asp Phe Ala
370                 375                 380

Gln Gly Trp Gly Pro Ile Ser Tyr Ala Asn Gly Ser Gly Leu Asp Glu
385                 390                 395                 400

Arg Pro Tyr Cys Trp His Tyr Pro Pro Arg Pro Cys Gly Ile Val Pro
                405                 410                 415

Ala Lys Ser Val Cys Gly Pro Val Tyr Cys Phe Thr Pro Ser Pro Val
            420                 425                 430

Val Val Gly Thr Thr Asp Arg Ser Gly Ala Pro Thr Tyr Ser Trp Gly
        435                 440                 445

Ala Asn Asp Thr Asp Val Phe Val Leu Asn Asn Thr Arg Pro Pro Leu
450                 455                 460

Gly Asn Trp Phe Gly Cys Thr Trp Met Asn Ser Thr Gly Phe Thr Lys
465                 470                 475                 480

Val Cys Gly Ala Pro Pro Cys Val Ile Gly Gly Val Gly Asn Asn Thr
                485                 490                 495

Leu Leu Cys Pro Thr Asp Cys Phe Arg Lys His Pro Glu Ala Thr Tyr
            500                 505                 510

Ser Arg Cys Gly Ser Gly Pro Trp Ile Thr Pro Arg Cys Met Val Asp
        515                 520                 525

Tyr Pro Tyr Arg Leu Trp His Tyr Pro Cys Thr Ile Asn Tyr Thr Ile
```

```
            530             535              540
Phe Lys Val Arg Met Tyr Val Gly Gly Val Glu His Arg Leu Glu Ala
545                 550                 555                 560

Ala Cys Asn Trp Thr Arg Gly Glu Arg Cys Asp Leu Glu Asp Arg Asp
                565                 570                 575

Arg Ser Glu Leu Ser Pro Leu Leu Ser Thr Thr Gln Trp Gln Val
            580                 585                 590

Leu Pro Cys Ser Phe Thr Thr Leu Pro Ala Leu Ser Thr Gly Leu Ile
            595                 600                 605

His Leu His Gln Asn Ile Val Asp Val Gln Tyr Leu Tyr Gly Val Gly
        610                 615                 620

Ser Ser Ile Ala Ser Trp Ala Ile Lys Trp Glu
625                 630                 635

<210> SEQ ID NO 15
<211> LENGTH: 2538
<212> TYPE: DNA
<213> ORGANISM: Artificial
<220> FEATURE:
<223> OTHER INFORMATION: recombinant fusion protein construct

<400> SEQUENCE: 15
atggccgacg aggcaccagc gcccatcacg gcgtacgccc agcagacgag aggcctccta    60
gggtgtataa tcaccagcct gactggccgg acaaaaaacc aagtggaggg tgaggtccag    120
atcgtgtcaa ctgctaccca aaccttcctg caacgtgca tcaatggggt atgctggact    180
gtctaccacg gggccggaac gaggaccatc gcatcaccca agggtcctgt catccagatg    240
tataccaatg tggaccaaga ccttgtgggc tggcccgctc ctcaaggttc ccgctcattg    300
acaccctgta cctgcggctc ctcggacctt tacctggtca cgaggcacgc cgatgtcatt    360
cccgtgcgcc ggcgaggtga tagcaggggt agcctgcttt cgccccggcc catttcctac    420
ttgaaaggct ccgctggggg tccgctgttg tgccccgcgg acacgccgt gggcctattc    480 agggccgcgg tgtgcacccg tggagtggct aaagcggtgg actttatccc tgtgagaac    540 ctagggacaa ccatgagatc cccggtgttc acggacaact cctctccacc agcagtgccc    600
cagagcttcc agtggcccca cctgcatgct cccaccggca gcgtaagag caccaaggtc    660 ccggctgcgt acgcagccca gggctacaag gtgttggtgc tcaacccctc tgttgctgca    720
acgctgggct ttggtgctta catgtccaag gcccatgggg ttgatcctaa tatcaggacc    780
ggggtgagaa caattaccac tggcagcccc atcacgtact ccacctacgg caagttcctt    840
gccgacggcg gtgctcagg aggtgcttat gacataataa tttgtgacga gtgccactcc    900
acggatgcca catccatctt gggcatcggc actgtccttg accaagcaga gactgcgggg    960
gcgagactgg ttgtgctcgc cactgctacc cctccgggct ccgtcactgt gtcccatcct    1020
aacatcgagg aggttgctct gtccaccacc ggagagatcc ctttttacgg caaggctatc    1080
cccctcgagg tgatcaaggg gggaagacat ctcatcttct gccactcaaa gaagaagtgc    1140
gacgagctcg ccgcgaagct ggtcgcattg gcatcaatg ccgtggccta ctaccgcggt    1200
cttgacgtgt ctgtcatccc gaccagcggc gatgttgtcg tcgtgtcgac cgatgctctc    1260
atgactggct ttaccggcga cttcgactct gtgatagact gcaacacgtg tgtcactcag    1320
acagtcgatt tcagccttga ccctacccttt accattgaga caaccacgct ccccaggat    1380 gctgtctcca ggactcaacg ccggggcagg actggcaggg ggaagccagg catctataga    1440
tttgtggcac cggggagcg cccctccggc atgttcgact cgtccgtcct ctgtgagtgc    1500
```

-continued

```
tatgacgcgg gctgtgcttg gtatgagctc acgcccgccg agactacagt taggctacga    1560
gcgtacatga acaccccggg gcttcccgtg tgccaggacc atcttgaatt ttgggagggc    1620
gtctttacgg gcctcactca tatagatgcc cactttttat cccagacaaa gcagagtggg    1680
gagaactttc cttacctggt agcgtaccaa gccaccgtgt gcgctagggc tcaagcccct    1740
cccccatcgt gggaccagat gtggaagtgt tgatccgcc ttaaacccac cctccatggg     1800
ccaacacccc tgctatacag actgggcgct gttcagaatg aagtcaccct gacgcaccca    1860
atcaccaaat acatcatgac atgcatgtcg gccgacctgg aggtcgtcac gagcacctgg    1920
gtgctcgttg gcggcgtcct ggctgctctg gccgcgtatt gcctgtcaac aggctgcgtg    1980
gtcatagtgg gcaggattgt cttgtccggg aagccggcaa ttatacctga cagggaggtt    2040
ctctaccagg agttcgatga gatggaagag tgctctcagc acttaccgta catcgagcaa    2100
gggatgatgc tcgctgagca gttcaagcag aaggccctcg gcctcctgca gaccgcgtcc    2160
cgccatgcag aggttatcac ccctgctgtc cagaccaact ggcagaaact cgaggtcttc    2220
tgggcgaagc acatgtggaa tttcatcagt gggatacaat acttggcggg cctgtcaact    2280
agtcctggag cccttgtagt cggtgtggtc tgcgcagcaa tactgcgccg gcacgttggc    2340
ccgggcgagg gggcagtgca atggatgaac cggctaatag ccttcgcctc ccggggggaac   2400 catgtttccc ccacgcacta cgtgccggag agcgatgcag ccgcccgcgt cactgccata    2460
ctcagcagcc tcactgtaac ccagctcctg aggcgactgc atcagtggat aagctcggag    2520
tgtaccactc catgctag                                                  2538
```

<210> SEQ ID NO 16
<211> LENGTH: 845
<212> TYPE: PRT
<213> ORGANISM: Artificial
<220> FEATURE:
<223> OTHER INFORMATION: recombinant fusion protein

<400> SEQUENCE: 16

```
Met Ala Asp Glu Ala Pro Ala Pro Ile Thr Ala Tyr Ala Gln Gln Thr
1               5                   10                  15

Arg Gly Leu Leu Gly Cys Ile Ile Thr Ser Leu Thr Gly Arg Asp Lys
                20                  25                  30

Asn Gln Val Glu Gly Glu Val Gln Ile Val Ser Thr Ala Thr Gln Thr
            35                  40                  45

Phe Leu Ala Thr Cys Ile Asn Gly Val Cys Trp Thr Val Tyr His Gly
        50                  55                  60

Ala Gly Thr Arg Thr Ile Ala Ser Pro Lys Gly Pro Val Ile Gln Met
65                  70                  75                  80

Tyr Thr Asn Val Asp Gln Asp Leu Val Gly Trp Pro Ala Pro Gln Gly
                85                  90                  95

Ser Arg Ser Leu Thr Pro Cys Thr Cys Gly Ser Ser Asp Leu Tyr Leu
                100                 105                 110

Val Thr Arg His Ala Asp Val Ile Pro Val Arg Arg Arg Gly Asp Ser
            115                 120                 125

Arg Gly Ser Leu Leu Ser Pro Arg Pro Ile Ser Tyr Leu Lys Gly Ser
        130                 135                 140

Ala Gly Gly Pro Leu Leu Cys Pro Ala Gly His Ala Val Gly Leu Phe
145                 150                 155                 160

Arg Ala Ala Val Cys Thr Arg Gly Val Ala Lys Ala Val Asp Phe Ile
                165                 170                 175
```

-continued

Pro Val Glu Asn Leu Gly Thr Thr Met Arg Ser Pro Val Phe Thr Asp
            180                 185                 190

Asn Ser Ser Pro Pro Ala Val Pro Gln Ser Phe Gln Val Ala His Leu
            195                 200                 205

His Ala Pro Thr Gly Ser Gly Lys Ser Thr Lys Val Pro Ala Ala Tyr
            210                 215                 220

Ala Ala Gln Gly Tyr Lys Val Leu Val Leu Asn Pro Ser Val Ala Ala
225                 230                 235                 240

Thr Leu Gly Phe Gly Ala Tyr Met Ser Lys Ala His Gly Val Asp Pro
                245                 250                 255

Asn Ile Arg Thr Gly Val Arg Thr Ile Thr Thr Gly Ser Pro Ile Thr
            260                 265                 270

Tyr Ser Thr Tyr Gly Lys Phe Leu Ala Asp Gly Gly Cys Ser Gly Gly
            275                 280                 285

Ala Tyr Asp Ile Ile Ile Cys Asp Glu Cys His Ser Thr Asp Ala Thr
            290                 295                 300

Ser Ile Leu Gly Ile Gly Thr Val Leu Asp Gln Ala Glu Thr Ala Gly
305                 310                 315                 320

Ala Arg Leu Val Val Leu Ala Thr Ala Thr Pro Pro Gly Ser Val Thr
                325                 330                 335

Val Ser His Pro Asn Ile Glu Glu Val Ala Leu Ser Thr Thr Gly Glu
            340                 345                 350

Ile Pro Phe Tyr Gly Lys Ala Ile Pro Leu Glu Val Ile Lys Gly Gly
            355                 360                 365

Arg His Leu Ile Phe Cys His Ser Lys Lys Lys Cys Asp Glu Leu Ala
            370                 375                 380

Ala Lys Leu Val Ala Leu Gly Ile Asn Ala Val Ala Tyr Tyr Arg Gly
385                 390                 395                 400

Leu Asp Val Ser Val Ile Pro Thr Ser Gly Asp Val Val Val Val Ser
                405                 410                 415

Thr Asp Ala Leu Met Thr Gly Phe Thr Gly Asp Phe Asp Ser Val Ile
            420                 425                 430

Asp Cys Asn Thr Cys Val Thr Gln Thr Val Asp Phe Ser Leu Asp Pro
            435                 440                 445

Thr Phe Thr Ile Glu Thr Thr Thr Leu Pro Gln Asp Ala Val Ser Arg
            450                 455                 460

Thr Gln Arg Arg Gly Arg Thr Gly Arg Gly Lys Pro Gly Ile Tyr Arg
465                 470                 475                 480

Phe Val Ala Pro Gly Glu Arg Pro Ser Gly Met Phe Asp Ser Ser Val
                485                 490                 495

Leu Cys Glu Cys Tyr Asp Ala Gly Cys Ala Trp Tyr Glu Leu Thr Pro
            500                 505                 510

Ala Glu Thr Thr Val Arg Leu Arg Ala Tyr Met Asn Thr Pro Gly Leu
            515                 520                 525

Pro Val Cys Gln Asp His Leu Glu Phe Trp Glu Gly Val Phe Thr Gly
            530                 535                 540

Leu Thr His Ile Asp Ala His Phe Leu Ser Gln Thr Lys Gln Ser Gly
545                 550                 555                 560

Glu Asn Phe Pro Tyr Leu Val Ala Tyr Gln Ala Thr Val Cys Ala Arg
                565                 570                 575

Ala Gln Ala Pro Pro Pro Ser Trp Asp Gln Met Trp Lys Cys Leu Ile
            580                 585                 590

| | | | | | | | | | | | | |
|---|---|---|---|---|---|---|---|---|---|---|---|---|
|Arg|Leu|Lys|Pro|Thr|Leu|His|Gly|Pro|Thr|Pro|Leu|Leu|Tyr|Arg|Leu|
| |595| | | | |600| | | | |605| | | | |

Arg Leu Lys Pro Thr Leu His Gly Pro Thr Pro Leu Leu Tyr Arg Leu
        595                 600                 605

Gly Ala Val Gln Asn Glu Val Thr Leu Thr His Pro Ile Thr Lys Tyr
    610                 615                 620

Ile Met Thr Cys Met Ser Ala Asp Leu Glu Val Val Thr Ser Thr Trp
625                 630                 635                 640

Val Leu Val Gly Gly Val Leu Ala Ala Leu Ala Ala Tyr Cys Leu Ser
                645                 650                 655

Thr Gly Cys Val Val Ile Val Gly Arg Ile Val Leu Ser Gly Lys Pro
            660                 665                 670

Ala Ile Ile Pro Asp Arg Glu Val Leu Tyr Gln Glu Phe Asp Glu Met
        675                 680                 685

Glu Glu Cys Ser Gln His Leu Pro Tyr Ile Glu Gln Gly Met Met Leu
    690                 695                 700

Ala Glu Gln Phe Lys Gln Lys Ala Leu Gly Leu Leu Gln Thr Ala Ser
705                 710                 715                 720

Arg His Ala Glu Val Ile Thr Pro Ala Val Gln Thr Asn Trp Gln Lys
                725                 730                 735

Leu Glu Val Phe Trp Ala Lys His Met Trp Asn Phe Ile Ser Gly Ile
            740                 745                 750

Gln Tyr Leu Ala Gly Leu Ser Thr Ser Pro Gly Ala Leu Val Val Gly
        755                 760                 765

Val Val Cys Ala Ala Ile Leu Arg Arg His Val Gly Pro Gly Glu Gly
    770                 775                 780

Ala Val Gln Trp Met Asn Arg Leu Ile Ala Phe Ala Ser Arg Gly Asn
785                 790                 795                 800

His Val Ser Pro Thr His Tyr Val Pro Glu Ser Asp Ala Ala Ala Arg
                805                 810                 815

Val Thr Ala Ile Leu Ser Ser Leu Thr Val Thr Gln Leu Leu Arg Arg
            820                 825                 830

Leu His Gln Trp Ile Ser Ser Glu Cys Thr Thr Pro Cys
        835                 840                 845

<210> SEQ ID NO 17
<211> LENGTH: 2982
<212> TYPE: DNA
<213> ORGANISM: Artificial
<220> FEATURE:
<223> OTHER INFORMATION: recombinant fusion protein construct

<400> SEQUENCE: 17

```
atggccgacg aggcaccatc cggttcctgg ctaagggaca tctgggactg gatatgcgag      60
gtgctgagcg actttaagac ctggctgaaa gccaagctca tgccacaact gcctgggatt     120
cccttttgtgt cctgccagcg cgggtatagg ggggtctggc gaggagacgg cattatgcac    180
actcgctgcc actgtggagc tgagatcact ggacatgtca aaaacgggac gatgaggatc     240
gtcggtccta ggacctgcag gaacatgtgg agtgggacgt tccccattaa cgcctacacc     300
acgggcccct gtactcccct tcctgcgccg aactataagt tcgcgctgtg gagggtgtct     360
gcagaggaat acgtggagat aaggcgggtg ggggacttcc actacgtatc gggtatgact     420
actgacaatt taaatgccc gtgccagatc ccatcgcccg aatttttcac agaattggac     480
ggggtgcgcc acataggtt tgcgccccct gcaagccct gctgcggga ggagtatca        540
ttcagagtag actccacga gtacccggtg gggtcgcaat accttgcga gcccgaaccg      600
gacgtagccg tgttgacgtc catgctcact gatccctccc atataacagc agaggcggcc     660
```

```
gggagaaggt tggcgagagg gtcacccccct tctatggcca gctcctcggc cagccagctg    720
tccgctccat ctctcaaggc aacttgcacc gccaaccatg actcccctga cgccgagctc    780
atagaggcta acctcctgtg gaggcaggag atgggcggca acatcaccag ggttgagtca    840
gagaacaaag tggtgattct ggactccttc gatccgcttg tggcagagga ggatgagcgg    900
gaggtctccg tacccgcaga aattctgcgg aagtctcgga gattcgcccg ggccctgccc    960
gtttgggcgc ggccggacta acccccccg ctagtagaga cgtggaaaaa gcctgactac    1020
gaaccacctg tggtccatgg ctgcccgcta ccacctccac ggtcccctcc tgtgcctccg    1080
cctcggaaaa agcgtacggt ggtcctcacc gaatcaaccc tatctactgc cttggccgag    1140
cttgccacca aaagttttgg cagctcctca acttccggca ttacgggcga caatacgaca    1200
acatcctctg agcccgcccc ttctggctgc ccccccgact ccgacgttga gtcctattct    1260
tccatgcccc ccctggaggg ggagcctggg gatccggatc tcagcgacgg gtcatggtcg    1320
acggtcagta gtggggccga cacggaagat gtcgtgtgct gctcaatgtc ttattcctgg    1380
acaggcgcac tcgtcacccc gtgcgctgcg gaagaacaaa aactgcccat caacgcactg    1440
agcaactcgt tgctacgcca tcacaatctg gtgtattcca ccacttcacg cagtgcttgc    1500
caaaggcaga gaaagtcac atttgacaga ctgcaagttc tggacagcca ttaccaggac    1560
gtgctcaagg aggtcaaagc agcggcgtca aaagtgaagg ctaacttgct atccgtagag    1620
gaagcttgca gcctgacgcc ccacattca gccaaatcca gtttggcta tggggcaaaa    1680
gacgtccgtt gccatgccag aaaggccgta gcccacatca actccgtgtg gaaagacctt    1740
ctggaagaca gtgtaacacc aatagacact accatcatgg ccaagaacga gttttctgc    1800
gttcagcctg agaagggggg tcgtaagcca gctcgtctca tcgtgttccc cgacctgggc    1860
gtgcgcgtgt gcgagaagat ggccctgtac gacgtggtta gcaagctccc cctggccgtg    1920
atgggaagct cctacggatt ccaatactca ccaggacagc gggttgaatt cctcgtgcaa    1980
gcgtggaagt ccaagaagac cccgatgggg ttctcgtatg ataccccgctg ttttgactcc    2040
acagtcactg agagcgacat ccgtacggag gaggcaattt accaatgttg tgacctggac    2100
ccccaagccc gcgtggccat caagtccctc actgagaggc tttatgttgg gggccctctt    2160
accaattcaa gggggggaaaa ctgccggcta cgcaggtgcc gcgcgagcgg cgtactgaca    2220
actagctgtg gtaacacccct cacttgctac atcaaggccc gggcagcctg tcgagccgca    2280
gggctccagg actgcaccat gctcgtgtgt ggcgacgact tagtcgttat ctgtgaaagt    2340
gcggggtcc aggaggacgc ggcgagcctg agagccttca cggaggctat gaccaggtac    2400
tccgccccccc ccgggaccc ccacaaacca gaatacgact ggagcttat aacatcatgc    2460
tcctccaacg tgtcagtcgc ccacgacggc gctggaaaga gggtctacta ccttacccgt    2520
gaccctacaa cccccctcgc gagagccgcg tgggagacag caagacacac tccagtcaat    2580
tcctggctag gcaacataat catgtttgcc cccacactgt gggcgaggat gatactgatg    2640
acccatttct ttagcgtcct catagccagg atcagcttg aacaggctct taactgtgag    2700
atctacggag cctgctactc catagaacca ctggatctac ctccaatcat tcaaagactc    2760
catggcctca gcgcattttc actccacagt tactctccag gtgaaatcaa tagggtggcc    2820
gcatgcctca gaaaacttgg ggtcccgccc ttgcgagctt ggagacaccg ggcccggagc    2880
gtccgcgcta ggcttctgtc cagaggaggc agggctgcca tatgtggcaa gtacctcttc    2940
aactgggcag taagaacaaa gctcaaactc actccaatat ag    2982
```

```
<210> SEQ ID NO 18
<211> LENGTH: 993
<212> TYPE: PRT
<213> ORGANISM: Artificial
<220> FEATURE:
<223> OTHER INFORMATION: recombinant fusion protein

<400> SEQUENCE: 18

Met Ala Asp Glu Ala Pro Ser Gly Ser Trp Leu Arg Asp Ile Trp Asp
1               5                   10                  15

Trp Ile Cys Glu Val Leu Ser Asp Phe Lys Thr Trp Leu Lys Ala Lys
                20                  25                  30

Leu Met Pro Gln Leu Pro Gly Ile Pro Phe Val Ser Cys Gln Arg Gly
            35                  40                  45

Tyr Arg Gly Val Trp Arg Gly Asp Gly Ile Met Thr Arg Cys His
    50                  55                  60

Cys Gly Ala Glu Ile Thr Gly His Val Lys Asn Gly Thr Met Arg Ile
65              70                  75                  80

Val Gly Pro Arg Thr Cys Arg Asn Met Trp Ser Gly Thr Phe Pro Ile
                85                  90                  95

Asn Ala Tyr Thr Thr Gly Pro Cys Thr Pro Leu Pro Ala Pro Asn Tyr
            100                 105                 110

Lys Phe Ala Leu Trp Arg Val Ser Ala Glu Glu Tyr Val Glu Ile Arg
        115                 120                 125

Arg Val Gly Asp Phe His Tyr Val Ser Gly Met Thr Thr Asp Asn Leu
    130                 135                 140

Lys Cys Pro Cys Gln Ile Pro Ser Pro Glu Phe Phe Thr Glu Leu Asp
145             150                 155                 160

Gly Val Arg Leu His Arg Phe Ala Pro Pro Cys Lys Pro Leu Leu Arg
                165                 170                 175

Glu Glu Val Ser Phe Arg Val Gly Leu His Glu Tyr Pro Val Gly Ser
            180                 185                 190

Gln Leu Pro Cys Glu Pro Glu Pro Asp Val Ala Val Leu Thr Ser Met
        195                 200                 205

Leu Thr Asp Pro Ser His Ile Thr Ala Glu Ala Ala Gly Arg Arg Leu
    210                 215                 220

Ala Arg Gly Ser Pro Pro Ser Met Ala Ser Ser Ser Ala Ser Gln Leu
225             230                 235                 240

Ser Ala Pro Ser Leu Lys Ala Thr Cys Thr Ala Asn His Asp Ser Pro
                245                 250                 255

Asp Ala Glu Leu Ile Glu Ala Asn Leu Leu Trp Arg Gln Glu Met Gly
            260                 265                 270

Gly Asn Ile Thr Arg Val Glu Ser Glu Asn Lys Val Val Ile Leu Asp
        275                 280                 285

Ser Phe Asp Pro Leu Val Ala Glu Glu Asp Glu Arg Glu Val Ser Val
    290                 295                 300

Pro Ala Glu Ile Leu Arg Lys Ser Arg Arg Phe Ala Arg Ala Leu Pro
305             310                 315                 320

Val Trp Ala Arg Pro Asp Tyr Asn Pro Pro Leu Val Glu Thr Trp Lys
                325                 330                 335

Lys Pro Asp Tyr Glu Pro Pro Val Val His Gly Cys Pro Leu Pro Pro
            340                 345                 350

Pro Arg Ser Pro Pro Val Pro Pro Arg Lys Lys Arg Thr Val Val
        355                 360                 365
```

-continued

Leu Thr Glu Ser Thr Leu Ser Thr Ala Leu Ala Glu Leu Ala Thr Lys
370                 375                 380

Ser Phe Gly Ser Ser Ser Thr Ser Gly Ile Thr Gly Asp Asn Thr Thr
385                 390                 395                 400

Thr Ser Ser Glu Pro Ala Pro Ser Gly Cys Pro Pro Asp Ser Asp Val
                405                 410                 415

Glu Ser Tyr Ser Ser Met Pro Pro Leu Glu Gly Pro Gly Asp Pro
            420                 425                 430

Asp Leu Ser Asp Gly Ser Trp Ser Thr Val Ser Ser Gly Ala Asp Thr
            435                 440                 445

Glu Asp Val Val Cys Cys Ser Met Ser Tyr Ser Trp Thr Gly Ala Leu
450                 455                 460

Val Thr Pro Cys Ala Ala Glu Glu Gln Lys Leu Pro Ile Asn Ala Leu
465                 470                 475                 480

Ser Asn Ser Leu Leu Arg His His Asn Leu Val Tyr Ser Thr Thr Ser
                485                 490                 495

Arg Ser Ala Cys Gln Arg Gln Lys Lys Val Thr Phe Asp Arg Leu Gln
                500                 505                 510

Val Leu Asp Ser His Tyr Gln Asp Val Leu Lys Glu Val Lys Ala Ala
            515                 520                 525

Ala Ser Lys Val Lys Ala Asn Leu Leu Ser Val Glu Glu Ala Cys Ser
530                 535                 540

Leu Thr Pro Pro His Ser Ala Lys Ser Lys Phe Gly Tyr Gly Ala Lys
545                 550                 555                 560

Asp Val Arg Cys His Ala Arg Lys Ala Val Ala His Ile Asn Ser Val
                565                 570                 575

Trp Lys Asp Leu Leu Glu Asp Ser Val Thr Pro Ile Asp Thr Thr Ile
            580                 585                 590

Met Ala Lys Asn Glu Val Phe Cys Val Gln Pro Glu Lys Gly Gly Arg
            595                 600                 605

Lys Pro Ala Arg Leu Ile Val Phe Pro Asp Leu Gly Val Arg Val Cys
610                 615                 620

Glu Lys Met Ala Leu Tyr Asp Val Val Ser Lys Leu Pro Leu Ala Val
625                 630                 635                 640

Met Gly Ser Ser Tyr Gly Phe Gln Tyr Ser Pro Gly Gln Arg Val Glu
            645                 650                 655

Phe Leu Val Gln Ala Trp Lys Ser Lys Lys Thr Pro Met Gly Phe Ser
            660                 665                 670

Tyr Asp Thr Arg Cys Phe Asp Ser Thr Val Thr Glu Ser Asp Ile Arg
    675                 680                 685

Thr Glu Glu Ala Ile Tyr Gln Cys Cys Asp Leu Asp Pro Gln Ala Arg
    690                 695                 700

Val Ala Ile Lys Ser Leu Thr Glu Arg Leu Tyr Val Gly Gly Pro Leu
705                 710                 715                 720

Thr Asn Ser Arg Gly Glu Asn Cys Gly Tyr Arg Arg Cys Arg Ala Ser
                725                 730                 735

Gly Val Leu Thr Thr Ser Cys Gly Asn Thr Leu Thr Cys Tyr Ile Lys
            740                 745                 750

Ala Arg Ala Ala Cys Arg Ala Ala Gly Leu Gln Asp Cys Thr Met Leu
            755                 760                 765

Val Cys Gly Asp Asp Leu Val Val Ile Cys Glu Ser Ala Gly Val Gln
770                 775                 780

Glu Asp Ala Ala Ser Leu Arg Ala Phe Thr Glu Ala Met Thr Arg Tyr

```
                785                 790                 795                 800
Ser Ala Pro Pro Gly Asp Pro Pro Gln Pro Glu Tyr Asp Leu Glu Leu
                805                 810                 815

Ile Thr Ser Cys Ser Ser Asn Val Ser Val Ala His Asp Gly Ala Gly
                820                 825                 830

Lys Arg Val Tyr Tyr Leu Thr Arg Asp Pro Thr Thr Pro Leu Ala Arg
                835                 840                 845

Ala Ala Trp Glu Thr Ala Arg His Thr Pro Val Asn Ser Trp Leu Gly
            850                 855                 860

Asn Ile Ile Met Phe Ala Pro Thr Leu Trp Ala Arg Met Ile Leu Met
865                 870                 875                 880

Thr His Phe Phe Ser Val Leu Ile Ala Arg Asp Gln Leu Glu Gln Ala
                885                 890                 895

Leu Asn Cys Glu Ile Tyr Gly Ala Cys Tyr Ser Ile Glu Pro Leu Asp
                900                 905                 910

Leu Pro Pro Ile Ile Gln Arg Leu His Gly Leu Ser Ala Phe Ser Leu
            915                 920                 925

His Ser Tyr Ser Pro Gly Glu Ile Asn Arg Val Ala Ala Cys Leu Arg
        930                 935                 940

Lys Leu Gly Val Pro Pro Leu Arg Ala Trp Arg His Arg Ala Arg Ser
945                 950                 955                 960

Val Arg Ala Arg Leu Leu Ser Arg Gly Gly Arg Ala Ala Ile Cys Gly
                965                 970                 975

Lys Tyr Leu Phe Asn Trp Ala Val Arg Thr Lys Leu Lys Leu Thr Pro
            980                 985                 990

Ile

<210> SEQ ID NO 19
<211> LENGTH: 9599
<212> TYPE: DNA
<213> ORGANISM: Hepatitis C virus

<400> SEQUENCE: 19
gccagccccc tgatgggggc gacactccac catgaatcac tcccctgtga ggaactattg      60
tcttcacgca gaaagcgtct agccatggcg ttagtatgag tgtcgtgcag cctccaggac     120 ccccccctccc gggagagcca tagtggtctg cggaaccggt gagtacaccg gaattgccag     180
gacgaccggg tcctttcttg gataaacccg ctcaatgcct ggagatttgg gcgtgccccc     240
gcaagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaacgt aacaccaacc gtcgcccaca ggacgtcaag ttcccgggtg     420
gcggtcagat cgttggtgga gtttacttgt tgccgcgcag gggccctaga ttgggtgtgc     480
gcgcgacgag gaagacttcc gagcggtcgc aacctcgagg tagacgtcag cctatcccca     540
aggcacgtcg gcccgagggc aggacctggg ctcagcccgg gtaccttgg ccctctatg     600 gcaatgaggg ttgcgggtgg gcgggatggc tcctgtctcc ccgtggctct cggcctagct     660
ggggccccac agaccccgg cgtaggtcgc gcaatttggg taaggtcatc gataccctta     720
cgtgcggctt cgccgacctc atggggtaca taccgctcgt cggcgcccct cttgagggcg     780
ctgccagggc cctggcgcat ggcgtccggg ttctggaaga cggcgtgaac tatgcaacag     840
ggaaccttcc tggttgctct ttctctatct tccttctggc cctgctctct tgcctgactg     900
tgcccgcttc agcctaccaa gtgcgcaatt cctcggggct ttaccatgtc accaatgatt     960
```

```
gccctaactc gagtattgtg tacgaggcgg ccgatgccat cctgcacact ccggggtgtg   1020
tcccttgcgt tcgcgagggt aacgcctcga ggtgttgggt ggcggtgacc cccacggtgg   1080
ccaccaggga cggcaaactc cccacaacgc agcttcgacg tcatatcgat ctgcttgtcg   1140
ggagcgccac cctctgctcg gccctctacg tgggggacct gtgcgggtct gtctttcttg   1200
ttggtcaact gtttaccttc tctcccaggc gccactggac gacgcaagac tgcaattgtt   1260
ctatctatcc cggccatata acgggtcatc gcatggcatg ggatatgatg atgaactggt   1320
cccctacggc agcgttggtg gtagctcagc tgctccggat cccacaagcc atcatggaca   1380
tgatcgctgg tgctcactgg ggagtcctgg cgggcatagc gtatttctcc atggtgggga   1440
actgggcgaa ggtcctggta gtgctgctgc tatttgccgg cgtcgacgcg gaaacccacg   1500
tcaccggggg aaatgccggc cgcaccacgg ctgggcttgt tggtctcctt acaccaggcg   1560
ccaagcagaa catccaactg atcaacacca acggcagttg gcacatcaat agcacggcct   1620
tgaactgcaa tgaaagcctt aacaccggct ggttagcagg gctcttctat cagcacaaat   1680
tcaactcttc aggctgtcct gagaggttga ccagctgccg acgccttacc gattttgccc   1740
agggctgggg tcctatcagt tatgccaacg gaagcggcct cgacgaacgc ccctactgct   1800
ggcactaccc tccaagacct tgtggcattg tgcccgcaaa gagcgtgtgt ggcccggtat   1860
attgcttcac tcccagcccc gtggtggtgg aacgaccga caggtcgggc gcgcctacct   1920
acagctgggg tgcaaatgat acggacgtct tcgtccttaa caacaccagg ccaccgctgg   1980
gcaattggtt cggttgtacc tggatgaact caactggatt caccaaagtg tgcggagcgc   2040
ccccttgtgt catcggaggg gtgggcaaca cacccttgct ctgccccact gattgcttcc   2100
gcaaacatcc ggaagccaca tactctcggt gcggctccgg tccctggatt acacccaggt   2160
gcatggtcga ctacccgtat aggctttggc actatccttg taccatcaat tacaccatat   2220
tcaaagtcag gatgtacgtg ggaggggtcg agcacaggct ggaagcggcc tgcaactgga   2280
cgcggggcga acgctgtgat ctggaagaca gggacaggtc cgagctcagc ccgttgctgc   2340
tgtccaccac acagtggcag gtccttccgt gttctttcac gaccctgcca gccttgtcca   2400
ccggcctcat ccacctccac cagaacattg tggacgtgca gtacttgtac ggggtagggt   2460
caagcatcgc gtcctgggcc attaagtggg agtacgtcgt tctcctgttc cttctgcttg   2520
cagacgcgcg cgtctgctcc tgcttgtgga tgatgttact catatcccaa gcggaggcgg   2580
ctttggagaa cctcgtaata ctcaatgcag catccctggc cggacgcac ggtcttgtgt   2640 ccttcctcgt gttcttctgc tttgcgtggt atctgaaggg taggtgggtg cccggagcgg   2700
cctacgccct ctacgggatg tggcctctcc tcctgctcct gctggcgttg cctcagcggg   2760
catacgcact ggacacggag gtggccgcgt cgtgtggcgg cgttgttctt gtcgggttaa   2820
tggcgctgac tctgtcgcca tattacaagc gctatatcag ctggtgcatg tggtggcttc   2880
agtattttct gaccagagta gaagcgcaac tgcacgtgtg ggttccccc ctcaacgtcc   2940 ggggggggcg cgatgccgtc atcttactca tgtgtagt acacccgacc ctggtatttg   3000
acatcaccaa actactcctg gccatcttcg gacccctttg gattcttcaa gccagtttgc   3060
ttaaagtccc ctacttcgtg cgcgttcaag gccttctccg gatctgcgcg ctagcgcgga   3120
agatagccgg aggtcattac gtgcaaatgg ccatcatcaa gttaggggcg cttactggca   3180
cctatgtgta taaccatctc accctcttc gagactgggc gcacaacggc ctgcgagatc   3240
tggccgtggc tgtggaacca gtcgttttct cccgaatgga gaccaagctc atcacgtggg   3300
```

```
gggcagatac cgccgcgtgc ggtgacatca tcaacggctt gcccgtctct gcccgtaggg    3360
gccaggagat actgcttggg ccagccgacg gaatggtctc caaggggtgg aggttgcagg    3420
cgcccatcac ggcgtacacc cagcagacga gaggcctcct agggtgtata atcaccagcc    3480
tgactggccg ggacaaaaac caagtggagg gtgaggtcca gatcgtgtca actgctaccc    3540
aaaccttcct ggcaacgtgc atcaatgggg tatgctggac tgtctaccac ggggccggaa    3600
cgaggaccat cgcatcaccc aagggtcctg tcatccagat gtataccaat gtggaccaag    3660
accttgtggg ctggcccgct cctcaaggtt cccgctcatt ggcaccctgc acctgcggct    3720
cctcggacct ttacctggtc acgaggcacg ccgatgtcat tcccgtgcgc cggcgaggtg    3780
atagcagggg tagcctgctt tcgccccggc ccatttccta cttgaaaggc tcctcggggg    3840
gtccgctgtt gtgccccgcg ggacacgccg tgggcctatt cagggccgcg gtgtgcaccc    3900
gtggagtggc taaggcggtg gactttatcc ctgtggagaa cctagggaca accatgagat    3960
ccccggtgtt cacggacaac tcctctccac cagcagtgcc ccagagcttc caggtggccc    4020
acctgcatgc tcccaccggc agcggtaaga gcaccaaggt cccggctgcg tacgcagccc    4080
agggctacaa ggtgttggtg ctcaacccct ctgttgctgc aacgctgggc tttggtgctt    4140
acatgtccaa ggcccatggg gttgatccta atatcaggac cggggtgaga acaattacca    4200
ctggcagccc catcacgtac tccacctacg gcaagttcct tgccgacggc gggtgctcag    4260
gaggtgctta tgacataata atttgtgacg agtgccactc cacggatgcc atccatct    4320
tgggcatcgg cactgtcctt gaccaagcag agactgcggg ggcgagactg gttgtgctcg    4380
ccactgctac ccctccgggc tccgtcactg tgtcccatcc taacatcgag gaggttgctc    4440
tgtccaccac cggagagatc cccttttacg gcaaggctat cccctcgag gtgatcaagg    4500
ggggaagaca tctcatcttc tgccattcaa agaagaagtg cgacgagctc gccgcgaagc    4560
tggtcgcatt gggcatcaat gccgtggcct actaccgcgg tcttgacgtg tctgtcatcc    4620
cgaccagcgg cgatgttgtc gtcgtgtcga ccgatgctct catgactggc tttaccggcg    4680
acttcgactc tgtgatagac tgcaacacgt gtgtcactca gacagtcgat ttcagccttg    4740
accctacctt taccattgag acaaccacgc tcccccagga tgctgtctcc aggactcaac    4800
gccggggcag gaccggcagg gggaagccag gcatctatag atttgtggca ccggggagc    4860
gccccctccgg catgttcgac tcgtccgtcc tctgtgagtg ctatgacgcg ggctgtgctt    4920
ggtatgagct cacgcccgcc gagactacag ttaggctacg agcgtacatg aacacccccgg    4980
ggcttcccgt gtgccaggac catcttgaat tttgggaggg cgtctttacg ggcctcactc    5040
atatagatgc ccactttcta tcccagacaa agcagagtgg ggagaacttt ccttacctgg    5100
tagcgtacca agccaccgtg tgcgctaggg ctcaagcccc tccccatcg tgggaccaga    5160
tgtggaagtg tttgatccgc cttaaaccca ccctccatgg gccaacaccc ctgctataca    5220
gactgggcgc tgttcagaat gaagtcaccc tgacgcaccc aatcaccaaa tacatcatga    5280
catgcatgtc ggccgacctg gaggtcgtca cgagcacctg ggtgctcgtt ggcggcgtcc    5340
tggctgctct ggccgcgtat tgcctgtcaa caggctgcgt ggtcatagtg gcaggatcg    5400
tcttgtccgg gaagccggca attatacctg acagggaggt tctctaccag gagttcgatg    5460
agatggaaga gtgctctcag cacttaccgt acatcgagca agggatgatg ctcgctgagc    5520
agttcaagca gaaggcctc ggcctcctgc agaccgcgtc ccgccatgca gaggttatca    5580
cccctgctgt ccagaccaac tggcagaaac tcgaggtctt tgggcgaag cacatgtgga    5640
atttcatcag tgggatacaa tacttggcgg gcctgtcaac gctgcctggt aaccccgcca    5700
```

```
ttgcttcatt gatggctttt acagctgccg tcaccagccc actaaccact ggccaaaccc    5760
tcctcttcaa catattgggg gggtgggtgg ctgcccagct cgccgccccc ggtgccgcta    5820
ctgcctttgt gggcgctggc ctagctgcg ccgccatcgg cagcgttgga ctggggaagg    5880
tcctcgtgga cattcttgca gggtatggcg cgggcgtggc gggagctctt gtagcattca    5940
agatcatgag cggtgaggtc ccctccacga aggacctggt caatctgctg cccgccatcc    6000
tctcgcctgg agcccttgta gtcggtgtgg tctgcgcagc aatactgcgc cggcacgttg    6060
gcccgggcga gggggcagtg caatggatga accggctaat agccttcgcc tcccggggga    6120
accatgtttc ccccacgcac tacgtgccgg agagcgatgc agccgcccgc gtcactgcca    6180
tactcagcag cctcactgta acccagctcc tgaggcgact gcatcagtgg ataagctcgg    6240
agtgtaccac tccatgctcc ggttcctggc taagggacat ctgggactgg atatgcgagg    6300
tgctgagcga ctttaagacc tggctgaaag ccaagctcat gccacaactg cctgggattc    6360
cctttgtgtc ctgccagcgc gggtataggg gggtctggcg aggagacggc attatgcaca    6420
ctcgctgcca ctgtggagct gagatcactg gacatgtcaa aaacgggacg atgaggatcg    6480
tcggtcctag gacttgcagg aacatgtgga gtgggacgtt ccccattaac gcctacacca    6540
cgggcccctg tactcccctt cctgcgccga actataagtt cgcgctgtgg agggtgtctg    6600
cagaggaata cgtggagata aggcgggtgg gggacttcca ctacgtatcg ggtatgacta    6660
ctgacaatct aaatgcccg tgccagatcc catcgcccga attttcaca gaattggacg    6720
gggtgcgcct acacaggttt gcgccccctt gcaagccctt gctgcgggag gaggtatcat    6780
tcagagtagg actccacgag tacccggtgg ggtcgcaatt accttgcgag cccgaaccgg    6840
acgtagccgt gttgacgtcc atgctcactg atccctccca tataacagca gaggcggccg    6900
ggagaaggtt ggcgagaggg tcaccccctt ctatggccag ctcctcggct agccagctgt    6960
ccgctccatc tctcaaggca acttgcaccg ccaaccatga ctcccctgac gccgagctca    7020
tagaggctaa cctcctgtgg aggcaggaga tgggcggcaa catcaccagg gttgagtcag    7080
agaacaaagt ggtgattctg gactccttcg atccgcttgt ggcagaggag gatgagcggg    7140
aggtctccgt acctgcagaa attctgcgga agtctcggag attcgcccgg gccctgcccg    7200
tctgggcgcg gccggactac aacccccgc tagtagagac gtggaaaaag cctgactacg    7260
aaccacctgt ggtccatggc tgcccgctac cacctccacg gtcccctcct gtgcctccgc    7320
ctcggaaaaa gcgtacggtg gtcctcaccg aatcaaccct atctactgcc ttggccgagc    7380
ttgccaccaa aagttttggc agctcctcaa cttccggcat tacggcgac aatacgacaa    7440
catcctctga gcccgcccct tctggctgcc ccccgactc cgacgttgag tcctattctt    7500
ccatgccccc cctggagggg gagcctgggg atccggatct cagcgacggg tcatggtcga    7560
cggtcagtag tggggccgac acggaagatg tcgtgtgctg ctcaatgtct tattcctgga    7620
caggcgcact cgtcacccg tgcgctgcgg aagaacaaaa actgcccatc aacgcactga    7680
gcaactcgtt gctacgccat cacaatctgg tgtattccac cacttcacgc agtgcttgcc    7740
aaaggcagaa gaaagtcaca tttgacagac tgcaagttct ggacagccat taccaggacg    7800
tgctcaagga ggtcaaagca gcggcgtcaa agtgaaggc taacttgcta tccgtagagg    7860
aagcttgcag cctgacgccc ccacattcag ccaaatccaa gtttggctat ggggcaaaag    7920
acgtccgttg ccatgccaga aaggccgtag cccacatcaa ctccgtgtgg aaagaccttc    7980
tggaagacag tgtaacacca atagacacta ccatcatggc caagaacgag gttttctgcg    8040
```

-continued

```
ttcagcctga aaggggggt cgtaagccag ctcgtctcat cgtgttcccc gacctgggcg      8100
tgcgcgtgtg cgagaagatg gccctgtacg acgtggttag caagctcccc ctggccgtga      8160
tgggaagctc ctacggattc caatactcac caggacagcg ggttgaattc ctcgtgcaag      8220
cgtggaagtc caagaagacc ccgatggggt tctcgtatga tacccgctgt tttgactcca      8280
cagtcactga gagcgacatc cgtacggagg aggcaattta ccaatgttgt gacctggacc      8340
cccaagcccg cgtggccatc aagtccctca ctgagaggct ttatgttggg ggccctctta      8400
ccaattcaag gggggaaaac tgcggctacc gcaggtgccg cgcgagcggc gtactgacaa      8460
ctagctgtgg taacaccctc acttgctaca tcaaggcccg gcagcctgt cgagccgcag      8520
ggctccagga ctgcaccatg ctcgtgtgtg gcgacgactt agtcgttatc tgtgaaagtg      8580
cgggggtcca ggaggacgcg gcgaacctga gagccttcac ggaggctatg accaggtact      8640
ccgcccccc cggggacccc ccacaaccag aatacgactt ggagcttata acatcatgct      8700
cctccaacgt gtcagtcgcc cacgacgcg ctggaaagag ggtctactac cttacccgtg      8760
accctacaac ccccctcgcg agagccgcgt gggagacagc aagcacact ccagtcaatt      8820
cctggctagg caacataatc atgtttgccc ccacactgtg ggcgaggatg atactgatga      8880
cccatttctt tagcgtcctc atagccaggg atcagcttga acaggctctt aactgtgaga      8940
tctacggagc ctgctactcc atagaaccac tggatctacc tccaatcatt caaagactcc      9000
atggcctcag cgcattttca ctccacagtt actctccagg tgaaatcaat agggtggccg      9060
catgcctcag aaaacttggg gtcccgcccc tgcgagcttg agacaccgg gcccggagcg      9120
tccgcgctag gcttctgtcc agaggaggca gggctgccat atgtggcaag tacctcttca      9180
actgggcagt aagaacaaag ctcaaactca ccccaataac ggccgctggc cggctggact      9240
tgtccggttg gttcacggct ggctacagcg ggggagacat ttatcacagc gtgtctcatg      9300
cccggccccg ctggttctgg ttttgcctac tcctgctcgc tgcaggggta ggcatctacc      9360
tcctcccaa ccgatgaagg ttggggtaaa cactccggcc tcttaagcca tttcctgttt      9420
tttttttttt ttttttttt ttttttcttt ttttttcttt tcctttcctt cttttttcc       9480
tttctttttc ccttctttaa tggtggctcc atcttagccc tagtcacggc tagctgtgaa      9540
aggtccgtga ccgcatgac tgcagagagt gctgatactg gcctctctgc agatcatgt       9599
```

<210> SEQ ID NO 20
<211> LENGTH: 3011
<212> TYPE: PRT
<213> ORGANISM: Hepatitis C virus

<400> SEQUENCE: 20

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
```

-continued

```
             100                 105                 110
Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
130             135                 140

Gly Gly Ala Ala Arg Ala Leu Ala His Gly Val Arg Val Leu Glu Asp
145             150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Leu Phe Ala Gly Val Asp Ala Glu
    370                 375                 380

Thr His Val Thr Gly Gly Asn Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
            420                 425                 430

Leu Asn Thr Gly Trp Leu Ala Gly Leu Phe Tyr Gln His Lys Phe Asn
        435                 440                 445

Ser Ser Gly Cys Pro Glu Arg Leu Thr Ser Cys Arg Arg Leu Thr Asp
    450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Arg Pro Cys Gly Ile
                485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
        515                 520                 525
```

-continued

```
Trp Gly Ala Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Val Gly Val Asn
                565                 570                 575

Asn Thr Leu Leu Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Met
        595                 600                 605

Val Asp Tyr Pro Tyr Arg Leu Trp His Tyr Pro Cys Thr Ile Asn Tyr
    610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Arg Trp Val Pro
    770                 775                 780

Gly Ala Ala Tyr Ala Phe Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Met Trp Trp Leu Gln Tyr
        835                 840                 845

Phe Leu Thr Arg Val Glu Ala Gln Leu His Val Trp Val Pro Pro Leu
    850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Ile Cys Ala Leu Ala Arg Lys Ile
        915                 920                 925

Ala Gly Gly His Tyr Val Gln Met Ala Ile Ile Lys Leu Gly Ala Leu
    930                 935                 940
```

-continued

```
Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
                980                 985                 990

Cys Gly Asp Ile Ile Asn Gly Leu Pro Val Ser Ala Arg Arg Gly Gln
            995                 1000                1005

Glu Ile Leu Leu Gly Pro Ala Asp Gly Met Val Ser Lys Gly Trp
        1010                1015                1020

Arg Leu Gln Ala Pro Ile Thr Ala Tyr Thr Gln Gln Thr Arg Gly
        1025                1030                1035

Leu Leu Gly Cys Ile Ile Thr Ser Leu Thr Gly Arg Asp Lys Asn
        1040                1045                1050

Gln Val Glu Gly Glu Val Gln Ile Val Ser Thr Ala Thr Gln Thr
        1055                1060                1065

Phe Leu Ala Thr Cys Ile Asn Gly Val Cys Trp Thr Val Tyr His
        1070                1075                1080

Gly Ala Gly Thr Arg Thr Ile Ala Ser Pro Lys Gly Pro Val Ile
        1085                1090                1095

Gln Met Tyr Thr Asn Val Asp Gln Asp Leu Val Gly Trp Pro Ala
        1100                1105                1110

Pro Gln Gly Ser Arg Ser Leu Ala Pro Cys Thr Cys Gly Ser Ser
        1115                1120                1125

Asp Leu Tyr Leu Val Thr Arg His Ala Asp Val Ile Pro Val Arg
        1130                1135                1140

Arg Arg Gly Asp Ser Arg Gly Ser Leu Leu Ser Pro Arg Pro Ile
        1145                1150                1155

Ser Tyr Leu Lys Gly Ser Ser Gly Gly Pro Leu Leu Cys Pro Ala
        1160                1165                1170

Gly His Ala Val Gly Leu Phe Arg Ala Ala Val Cys Thr Arg Gly
        1175                1180                1185

Val Ala Lys Ala Val Asp Phe Ile Pro Val Glu Asn Leu Gly Thr
        1190                1195                1200

Thr Met Arg Ser Pro Val Phe Thr Asp Asn Ser Ser Pro Pro Ala
        1205                1210                1215

Val Pro Gln Ser Phe Gln Val Ala His Leu His Ala Pro Thr Gly
        1220                1225                1230

Ser Gly Lys Ser Thr Lys Val Pro Ala Ala Tyr Ala Ala Gln Gly
        1235                1240                1245

Tyr Lys Val Leu Val Leu Asn Pro Ser Val Ala Ala Thr Leu Gly
        1250                1255                1260

Phe Gly Ala Tyr Met Ser Lys Ala His Gly Val Asp Pro Asn Ile
        1265                1270                1275

Arg Thr Gly Val Arg Thr Ile Thr Thr Gly Ser Pro Ile Thr Tyr
        1280                1285                1290

Ser Thr Tyr Gly Lys Phe Leu Ala Asp Gly Gly Cys Ser Gly Gly
        1295                1300                1305

Ala Tyr Asp Ile Ile Ile Cys Asp Glu Cys His Ser Thr Asp Ala
        1310                1315                1320

Thr Ser Ile Leu Gly Ile Gly Thr Val Leu Asp Gln Ala Glu Thr
        1325                1330                1335

Ala Gly Ala Arg Leu Val Val Leu Ala Thr Ala Thr Pro Pro Gly
```

```
                    1340                1345                1350

Ser Val Thr Val Ser His Pro Asn Ile Glu Glu Val Ala Leu Ser
           1355                1360                1365

Thr Thr Gly Glu Ile Pro Phe Tyr Gly Lys Ala Ile Pro Leu Glu
           1370                1375                1380

Val Ile Lys Gly Gly Arg His Leu Ile Phe Cys His Ser Lys Lys
           1385                1390                1395

Lys Cys Asp Glu Leu Ala Ala Lys Leu Val Ala Leu Gly Ile Asn
           1400                1405                1410

Ala Val Ala Tyr Tyr Arg Gly Leu Asp Val Ser Val Ile Pro Thr
           1415                1420                1425

Ser Gly Asp Val Val Val Ser Thr Asp Ala Leu Met Thr Gly
           1430                1435                1440

Phe Thr Gly Asp Phe Asp Ser Val Ile Asp Cys Asn Thr Cys Val
           1445                1450                1455

Thr Gln Thr Val Asp Phe Ser Leu Asp Pro Thr Phe Thr Ile Glu
           1460                1465                1470

Thr Thr Thr Leu Pro Gln Asp Ala Val Ser Arg Thr Gln Arg Arg
           1475                1480                1485

Gly Arg Thr Gly Arg Gly Lys Pro Gly Ile Tyr Arg Phe Val Ala
           1490                1495                1500

Pro Gly Glu Arg Pro Ser Gly Met Phe Asp Ser Ser Val Leu Cys
           1505                1510                1515

Glu Cys Tyr Asp Ala Gly Cys Ala Trp Tyr Glu Leu Thr Pro Ala
           1520                1525                1530

Glu Thr Thr Val Arg Leu Arg Ala Tyr Met Asn Thr Pro Gly Leu
           1535                1540                1545

Pro Val Cys Gln Asp His Leu Glu Phe Trp Glu Gly Val Phe Thr
           1550                1555                1560

Gly Leu Thr His Ile Asp Ala His Phe Leu Ser Gln Thr Lys Gln
           1565                1570                1575

Ser Gly Glu Asn Phe Pro Tyr Leu Val Ala Tyr Gln Ala Thr Val
           1580                1585                1590

Cys Ala Arg Ala Gln Ala Pro Pro Pro Ser Trp Asp Gln Met Trp
           1595                1600                1605

Lys Cys Leu Ile Arg Leu Lys Pro Thr Leu His Gly Pro Thr Pro
           1610                1615                1620

Leu Leu Tyr Arg Leu Gly Ala Val Gln Asn Glu Val Thr Leu Thr
           1625                1630                1635

His Pro Ile Thr Lys Tyr Ile Met Thr Cys Met Ser Ala Asp Leu
           1640                1645                1650

Glu Val Val Thr Ser Thr Trp Val Leu Val Gly Gly Val Leu Ala
           1655                1660                1665

Ala Leu Ala Ala Tyr Cys Leu Ser Thr Gly Cys Val Val Ile Val
           1670                1675                1680

Gly Arg Ile Val Leu Ser Gly Lys Pro Ala Ile Ile Pro Asp Arg
           1685                1690                1695

Glu Val Leu Tyr Gln Glu Phe Asp Glu Met Glu Glu Cys Ser Gln
           1700                1705                1710

His Leu Pro Tyr Ile Glu Gln Gly Met Met Leu Ala Glu Gln Phe
           1715                1720                1725

Lys Gln Lys Ala Leu Gly Leu Leu Gln Thr Ala Ser Arg His Ala
           1730                1735                1740
```

-continued

```
Glu Val Ile Thr Pro Ala Val Gln Thr Asn Trp Gln Lys Leu Glu
1745                1750                1755

Val Phe Trp Ala Lys His Met Trp Asn Phe Ile Ser Gly Ile Gln
1760                1765                1770

Tyr Leu Ala Gly Leu Ser Thr Leu Pro Gly Asn Pro Ala Ile Ala
1775                1780                1785

Ser Leu Met Ala Phe Thr Ala Ala Val Thr Ser Pro Leu Thr Thr
1790                1795                1800

Gly Gln Thr Leu Leu Phe Asn Ile Leu Gly Gly Trp Val Ala Ala
1805                1810                1815

Gln Leu Ala Ala Pro Gly Ala Ala Thr Ala Phe Val Gly Ala Gly
1820                1825                1830

Leu Ala Gly Ala Ala Ile Gly Ser Val Gly Leu Gly Lys Val Leu
1835                1840                1845

Val Asp Ile Leu Ala Gly Tyr Gly Ala Gly Val Ala Gly Ala Leu
1850                1855                1860

Val Ala Phe Lys Ile Met Ser Gly Glu Val Pro Ser Thr Glu Asp
1865                1870                1875

Leu Val Asn Leu Leu Pro Ala Ile Leu Ser Pro Gly Ala Leu Val
1880                1885                1890

Val Gly Val Val Cys Ala Ala Ile Leu Arg Arg His Val Gly Pro
1895                1900                1905

Gly Glu Gly Ala Val Gln Trp Met Asn Arg Leu Ile Ala Phe Ala
1910                1915                1920

Ser Arg Gly Asn His Val Ser Pro Thr His Tyr Val Pro Glu Ser
1925                1930                1935

Asp Ala Ala Ala Arg Val Thr Ala Ile Leu Ser Ser Leu Thr Val
1940                1945                1950

Thr Gln Leu Leu Arg Arg Leu His Gln Trp Ile Ser Ser Glu Cys
1955                1960                1965

Thr Thr Pro Cys Ser Gly Ser Trp Leu Arg Asp Ile Trp Asp Trp
1970                1975                1980

Ile Cys Glu Val Leu Ser Asp Phe Lys Thr Trp Leu Lys Ala Lys
1985                1990                1995

Leu Met Pro Gln Leu Pro Gly Ile Pro Phe Val Ser Cys Gln Arg
2000                2005                2010

Gly Tyr Arg Gly Val Trp Arg Gly Asp Gly Ile Met His Thr Arg
2015                2020                2025

Cys His Cys Gly Ala Glu Ile Thr Gly His Val Lys Asn Gly Thr
2030                2035                2040

Met Arg Ile Val Gly Pro Arg Thr Cys Arg Asn Met Trp Ser Gly
2045                2050                2055

Thr Phe Pro Ile Asn Ala Tyr Thr Thr Gly Pro Cys Thr Pro Leu
2060                2065                2070

Pro Ala Pro Asn Tyr Lys Phe Ala Leu Trp Arg Val Ser Ala Glu
2075                2080                2085

Glu Tyr Val Glu Ile Arg Arg Val Gly Asp Phe His Tyr Val Ser
2090                2095                2100

Gly Met Thr Thr Asp Asn Leu Lys Cys Pro Cys Gln Ile Pro Ser
2105                2110                2115

Pro Glu Phe Phe Thr Glu Leu Asp Gly Val Arg Leu His Arg Phe
2120                2125                2130
```

-continued

```
Ala Pro Pro Cys Lys Pro Leu Leu Arg Glu Glu Val Ser Phe Arg
2135                2140                    2145

Val Gly Leu His Glu Tyr Pro Val Gly Ser Gln Leu Pro Cys Glu
2150                2155                    2160

Pro Glu Pro Asp Val Ala Val Leu Thr Ser Met Leu Thr Asp Pro
2165                2170                    2175

Ser His Ile Thr Ala Glu Ala Ala Gly Arg Arg Leu Ala Arg Gly
2180                2185                    2190

Ser Pro Pro Ser Met Ala Ser Ser Ser Ala Ser Gln Leu Ser Ala
2195                2200                    2205

Pro Ser Leu Lys Ala Thr Cys Thr Ala Asn His Asp Ser Pro Asp
2210                2215                    2220

Ala Glu Leu Ile Glu Ala Asn Leu Leu Trp Arg Gln Glu Met Gly
2225                2230                    2235

Gly Asn Ile Thr Arg Val Glu Ser Glu Asn Lys Val Val Ile Leu
2240                2245                    2250

Asp Ser Phe Asp Pro Leu Val Ala Glu Asp Glu Arg Glu Val
2255                2260                    2265

Ser Val Pro Ala Glu Ile Leu Arg Lys Ser Arg Arg Phe Ala Arg
2270                2275                    2280

Ala Leu Pro Val Trp Ala Arg Pro Asp Tyr Asn Pro Pro Leu Val
2285                2290                    2295

Glu Thr Trp Lys Lys Pro Asp Tyr Glu Pro Pro Val Val His Gly
2300                2305                    2310

Cys Pro Leu Pro Pro Arg Ser Pro Val Pro Pro Arg
2315                2320                    2325

Lys Lys Arg Thr Val Val Leu Thr Glu Ser Thr Leu Ser Thr Ala
2330                2335                    2340

Leu Ala Glu Leu Ala Thr Lys Ser Phe Gly Ser Ser Ser Thr Ser
2345                2350                    2355

Gly Ile Thr Gly Asp Asn Thr Thr Thr Ser Ser Glu Pro Ala Pro
2360                2365                    2370

Ser Gly Cys Pro Pro Asp Ser Asp Val Glu Ser Tyr Ser Ser Met
2375                2380                    2385

Pro Pro Leu Glu Gly Glu Pro Gly Asp Pro Asp Leu Ser Asp Gly
2390                2395                    2400

Ser Trp Ser Thr Val Ser Ser Gly Ala Asp Thr Glu Asp Val Val
2405                2410                    2415

Cys Cys Ser Met Ser Tyr Ser Trp Thr Gly Ala Leu Val Thr Pro
2420                2425                    2430

Cys Ala Ala Glu Glu Gln Lys Leu Pro Ile Asn Ala Leu Ser Asn
2435                2440                    2445

Ser Leu Leu Arg His His Asn Leu Val Tyr Ser Thr Thr Ser Arg
2450                2455                    2460

Ser Ala Cys Gln Arg Gln Lys Lys Val Thr Phe Asp Arg Leu Gln
2465                2470                    2475

Val Leu Asp Ser His Tyr Gln Asp Val Leu Lys Glu Val Lys Ala
2480                2485                    2490

Ala Ala Ser Lys Val Lys Ala Asn Leu Leu Ser Val Glu Glu Ala
2495                2500                    2505

Cys Ser Leu Thr Pro Pro His Ser Ala Lys Ser Lys Phe Gly Tyr
2510                2515                    2520
```

-continued

```
Gly Ala Lys Asp Val Arg Cys His Ala Arg Lys Ala Val Ala His
2525                2530                2535

Ile Asn Ser Val Trp Lys Asp Leu Leu Glu Asp Ser Val Thr Pro
2540                2545                2550

Ile Asp Thr Thr Ile Met Ala Lys Asn Glu Val Phe Cys Val Gln
2555                2560                2565

Pro Glu Lys Gly Gly Arg Lys Pro Ala Arg Leu Ile Val Phe Pro
2570                2575                2580

Asp Leu Gly Val Arg Val Cys Glu Lys Met Ala Leu Tyr Asp Val
2585                2590                2595

Val Ser Lys Leu Pro Leu Ala Val Met Gly Ser Ser Tyr Gly Phe
2600                2605                2610

Gln Tyr Ser Pro Gly Gln Arg Val Glu Phe Leu Gln Ala Trp
2615                2620                2625

Lys Ser Lys Lys Thr Pro Met Gly Phe Ser Tyr Asp Thr Arg Cys
2630                2635                2640

Phe Asp Ser Thr Val Thr Glu Ser Asp Ile Arg Thr Glu Glu Ala
2645                2650                2655

Ile Tyr Gln Cys Cys Asp Leu Asp Pro Gln Ala Arg Val Ala Ile
2660                2665                2670

Lys Ser Leu Thr Glu Arg Leu Tyr Val Gly Gly Pro Leu Thr Asn
2675                2680                2685

Ser Arg Gly Glu Asn Cys Gly Tyr Arg Arg Cys Arg Ala Ser Gly
2690                2695                2700

Val Leu Thr Thr Ser Cys Gly Asn Thr Leu Thr Cys Tyr Ile Lys
2705                2710                2715

Ala Arg Ala Ala Cys Arg Ala Ala Gly Leu Gln Asp Cys Thr Met
2720                2725                2730

Leu Val Cys Gly Asp Asp Leu Val Val Ile Cys Glu Ser Ala Gly
2735                2740                2745

Val Gln Glu Asp Ala Ala Asn Leu Arg Ala Phe Thr Glu Ala Met
2750                2755                2760

Thr Arg Tyr Ser Ala Pro Pro Gly Asp Pro Pro Gln Pro Glu Tyr
2765                2770                2775

Asp Leu Glu Leu Ile Thr Ser Cys Ser Ser Asn Val Ser Val Ala
2780                2785                2790

His Asp Gly Ala Gly Lys Arg Val Tyr Tyr Leu Thr Arg Asp Pro
2795                2800                2805

Thr Thr Pro Leu Ala Arg Ala Ala Trp Glu Thr Ala Arg His Thr
2810                2815                2820

Pro Val Asn Ser Trp Leu Gly Asn Ile Ile Met Phe Ala Pro Thr
2825                2830                2835

Leu Trp Ala Arg Met Ile Leu Met Thr His Phe Phe Ser Val Leu
2840                2845                2850

Ile Ala Arg Asp Gln Leu Glu Gln Ala Leu Asn Cys Glu Ile Tyr
2855                2860                2865

Gly Ala Cys Tyr Ser Ile Glu Pro Leu Asp Leu Pro Pro Ile Ile
2870                2875                2880

Gln Arg Leu His Gly Leu Ser Ala Phe Ser Leu His Ser Tyr Ser
2885                2890                2895

Pro Gly Glu Ile Asn Arg Val Ala Ala Cys Leu Arg Lys Leu Gly
2900                2905                2910
```

-continued

| | | | | | | | | | | | |
|---|---|---|---|---|---|---|---|---|---|---|---|
| Val | Pro 2915 | Pro | Leu | Arg | Ala | Trp 2920 | Arg | His | Arg | Ala | Arg 2925 | Ser | Val | Arg |
| Ala | Arg 2930 | Leu | Leu | Ser | Arg | Gly 2935 | Gly | Arg | Ala | Ala | Ile 2940 | Cys | Gly | Lys |
| Tyr | Leu 2945 | Phe | Asn | Trp | Ala | Val 2950 | Arg | Thr | Lys | Leu | Lys 2955 | Leu | Thr | Pro |
| Ile | Thr 2960 | Ala | Ala | Gly | Arg | Leu 2965 | Asp | Leu | Ser | Gly | Trp 2970 | Phe | Thr | Ala |
| Gly | Tyr 2975 | Ser | Gly | Gly | Asp | Ile 2980 | Tyr | His | Ser | Val | Ser 2985 | His | Ala | Arg |
| Pro | Arg 2990 | Trp | Phe | Trp | Phe | Cys 2995 | Leu | Leu | Leu | Leu | Ala 3000 | Ala | Gly | Val |
| Gly | Ile 3005 | Tyr | Leu | Leu | Pro | Asn 3010 | Arg |

<210> SEQ ID NO 21
<211> LENGTH: 7
<212> TYPE: DNA
<213> ORGANISM: Artificial
<220> FEATURE:
<223> OTHER INFORMATION: oligonucleotide

<400> SEQUENCE: 21 accatgg                                                              7